(12) United States Patent
Dang

(10) Patent No.: US 6,350,464 B1
(45) Date of Patent: Feb. 26, 2002

(54) METHODS FOR TREATING OVARIAN CANCER, POLY (PHOSPHOESTER) COMPOSITIONS, AND BIODEGRADABLE ARTICLES FOR SAME

(75) Inventor: Wenbin Dang, Ellicott City, MD (US)

(73) Assignee: Guilford Pharmaceuticals, Inc., Baltimore, MD (US)

( * ) Notice: Subject to any disclaimer, the term of this patent is extended or adjusted under 35 U.S.C. 154(b) by 0 days.

(21) Appl. No.: 09/227,852

(22) Filed: Jan. 11, 1999

(51) Int. Cl.[7] .............................. A61F 2/02; A61K 47/30
(52) U.S. Cl. ..................................... 424/426; 514/772.3
(58) Field of Search ........................ 424/426; 514/772.3

(56) References Cited

U.S. PATENT DOCUMENTS

| | | |
|---|---|---|
| 2,891,915 A | 6/1959 | McCormack et al. |
| 3,271,329 A | 9/1966 | Coover et al. |
| 3,442,982 A | 5/1969 | Friedman |
| 3,927,231 A | 12/1975 | Desitter et al. |
| 3,932,566 A | 1/1976 | Reader |
| 4,100,354 A | 7/1978 | Owen |
| 4,259,222 A | 3/1981 | Login et al. |
| 4,328,174 A | 5/1982 | Schmidt et al. |
| 4,474,937 A | 10/1984 | Bales |
| 4,481,353 A | 11/1984 | Nyilas et al. |
| 4,757,128 A | 7/1988 | Domb et al. |
| 4,789,724 A | 12/1988 | Domb et al. |
| 4,978,332 A | 12/1990 | Luck et al. |
| 5,194,581 A | 3/1993 | Leong |
| 5,213,804 A | 5/1993 | Martin et al. |
| 5,256,765 A | 10/1993 | Leong .......................... 528/398 |
| 5,304,377 A | 4/1994 | Yamada et al. |
| 5,429,634 A | 7/1995 | Narciso et al. |
| 5,530,093 A | 6/1996 | Engelhardt et al. |
| 5,626,862 A | 5/1997 | Brem et al. ................. 424/426 |
| 5,637,085 A | 6/1997 | Cardinale |
| 5,651,986 A | 7/1997 | Brem et al. ................. 424/484 |
| 5,846,565 A | 12/1998 | Brem et al. ................. 424/486 |
| 5,912,225 A | 6/1999 | Mao et al. ....................... 514/2 |
| 5,952,451 A | 9/1999 | Zhao |
| 5,993,856 A | 11/1999 | Ragavan et al. |
| 6,008,318 A | 12/1999 | Zhao et al. ................. 528/398 |

FOREIGN PATENT DOCUMENTS

| | | |
|---|---|---|
| CA | 597473 | 5/1960 |
| CA | 2250981 | 10/1997 |
| EP | 0 057 116 | 8/1982 |
| EP | 0 193 019 | 9/1986 |
| EP | 0 386 757 B1 | 9/1990 |
| WO | WO 95/17901 | 7/1995 |
| WO | WO9622786 | 1/1996 |
| WO | WO 97/40085 | 10/1997 |
| WO | WO 9848859 | 5/1998 |
| WO | WO 9844020 | 8/1998 |
| WO | WO 9844021 | 8/1998 |
| WO | WO 98/42330 | 10/1998 |
| WO | WO 98/48859 | * 11/1998 |
| WO | WO 98/58012 | 12/1998 |

OTHER PUBLICATIONS

Williams, Jeffery A., et al., Implantable Biodegradable Polymers for IUdR Radiosensitization of Experimental Human Malignant Glioma, *Journal of Neuro–Oncology* 32; 181–192, 1997.

(List continued on next page.)

*Primary Examiner*—Carlos A. Azpuru
(74) *Attorney, Agent, or Firm*—Foley, Hoag & Eliot LLP

(57) ABSTRACT

Biodegradable polymer compositions suitable for intraperitoneal administration to treat a mammalian subject having ovarian cancer are described, wherein the polymer compositions provide extended release of the antineoplastic agent into the peritoneum of the subject. The subject compositions can increase the median survival rate from the cancer by at least about 10%, as compared with the median survival rate obtained by administration of a composition comprising the same dosage of the antineoplastic agent without the biodegradable polymer. Solid articles and methods for treating ovarian cancer are also described.

113 Claims, 49 Drawing Sheets

OTHER PUBLICATIONS

Demetrick, Jeffrey S., et al., The Development of a Novel Intraperitoneal Tumor–Seeding Prophylactic, *The American Journal of Surgery®*, vol. 173, May 1997.

Francis, Prudence, et al., Phase I Feasibility and Pharmacologic Study of Weekly Intraperitoneal Paclitaxel: A Gynecologic Oncology Group Pilot Study, *Journal of Clinical Oncology*, vol. 13, No. 12 (Dec.), 1995: pp. 2961–2967.

Hagiwara, Akeo, M.D., et al., Pharmacologic Effects of Cisplatin Microspheres on Peritoneal Carcinomatosis in Rodents, *Cancer*, Feb. 1, 1993, vol. 71, No. 3, pp. 844–850.

Hagiwara, Akeo, et al., Clinical trials with intraperitoneal cisplatin microspheres for malignant ascites—a pilot study, *Anti–Cancer Drug Design* (1993), 8, 463–470.

Höckel, M. et al., Prevention of Peritoneal Adhesions in the Rat with Sustained Intraperitoneal Dexamethasone Delivered by a Novel Therapeutic System, *Annales Chirurgiae et Gynaecologiae* 76: 306–313, 1987.

Jameela, S.R., Antitumour Activity of Mitoxantrone–loaded Chitosan Microspheres Against Ehrlich Ascites Carcinoma, *J. Pharm. Pharmacol.* 1986, 48: 685–688.

Kumagai, Seisuke, et al., Improvement of Intraperitoneal Chemotherapy for Rat Ovarian Cancer Using Cisplatin–containing Microspheres, *Jpn. J. Cancer Res.* 87, 412–417, Apr. 1996.

Liggins, R.T., et al., Taxol Loaded Microspheres for the Treatment of Intraperitoneally Seeded Tumours, *University of British Columbia*, Vancouver, B.C. Canada V6T 1Z.

Owusu–Ababio, G., et al., Efficacy of sustained release ciprofloxacin microspheres against device–associated *Pseudomonas aeruginosa* biofilm infection in a rabbit peritoneal model, J. Med. Microbiol., vol. 43 (1995), 368–376.

Pec, E.A., et al., Biological Activity of Urease Formulated in Poloxamer 407 after Intraperitoneal Injection in the Rat, *Journal of Pharmaceutical Sciences*, vol. 81, No. 7, Jul. 1992.

Sharma, Amarnath, et al., Antitumor Efficacy of Taxane Liposomes on a Human Ovarian Tumor Xenograft in Nude Athymic Mice, *Journal of Pharmaceutical Sciences*, vol. 84, No. 12, Dec. 1995.

Kaetsu, Isao, et al., Biodegradable Implant Composites for Local Therapy, *Journal of Controlled Release*, 6 (1987) 249–263.

Zhang, Xichen, et al., Development of Biodegradable Polymeric Paste Formulations for Taxol: An In Vitro and In Vivo Study, *International Journal of Pharmaceutics* 137 (1996) 199–208.

Auerbach, Robert, et al., Site–Specific Drug Delivery to the Lung, *Polymers for Advanced Technologies*, vol. 3, pp. 323–329.

Walter, Kevin A., et al., Intratumoral Chemotherapy, *Neurosurgery*, vol. 37, No. 6, Dec. 1995.

Burt, Helen M., et al., Controlled Delivery of Taxol from Microspheres Composed of a Blend of Ethylene–Vinyl Acetate Copolymer and Poly (d,l–lactic acid), *Cancer Letters*, 88 (1995) 73–79.

Zhang, X., et al., Biodegradable Polymeric Pastes for Taxol: An In Vitro and In Vivo Study, *Angiogenesis Technologies, Inc.*, V6E 3X1.

Langer, Robert, New Methods of Drug Delivery, *Articles*, Sep. 28, 1990.

Leong, K.W., et al., Polymeric Controlled Drug Delivery, *Advanced Drug Delivery Reviews*, 1 (1987) 199–233.

Penczek, Stanislaw, et al., Phosphorous–Controlled Polymers, *Handbook of Polymer Synthesis*, Part b, Chapter 17, pp. 1077–1132.

Bruin, P., et al., Biodegradable Lysine Diisocyanate–Based Poly(glycolide–co–ϵ–caprolactone)–Urethane Network in Artificial Skin.

Pulapura, Satish, et al., Trends in the Development of Bioresorbable Polymers for Medical Applications, *Journal of Biomaterials Applications*, vol. 6, Jan. 1992.

Mao, Hai–Quan, et al., Synthesis and Biological Properties of Polymer Immunoadjuvants, *Polymer Journal*, vol. 25, No. 5, pp. 499–505 (1993).

Winternitz, Charles I., et al., Development of a Polymeric Surgical Paste Formulation for Taxol, *Pharmaceutical Research*, vol. 13, No. 3, 1996.

Wang, Ya Min, et al., Prepartation and Characterization of Poly(lactic–co–glycolic acid) Microspheres for Targeted Delivery of a Novel Anticancer Agent, Taxol, *Chem. Pharm. Bull.* 44 (10) 1935–1940 (1996).

Sharma, Dayanand, Novel Taxol® Formulation: Polyvinylpyrrolidone Nanoparticle–Encapsulated Taxol® for Drug Delivery in Cancer Therapy, *Oncology Research*, vol. 8, Nos. 7/8, pp. 281–286, 1996.

Alkan–Onyuksel, Hayat, et al., A Mixed Micellar Formulation Suitable for the Parenteral Administration of Taxol, *Pharmaceutical Research*, vol. 11, No. 2, 1994.

Dordunoo, S.K., et al., Release of Taxol from Poly (ϵ–caprolactone) Pastes: Effect of Water–Soluble Additives, *Journal of Controlled Release*, 44 (1997) 87–94.

Suh, Hearan, et al., Regulation of Smooth Muscle Cell Proliferation Using Paclitaxel–Loaded Poly(ethylene oxide)–poly(lactide/glycolide) Nanospheres.

Lo, Hungnan, Synthesis of Biodegradable Polymers and Porous Grafts for Orthopedic Applications, *Thesis*, Johns Hopkins University, Jan. 27, 1995.

Chemical Abstracts, vol. 99, No. 22, abstract No. 176481 Akutin et al. Polyarylates (1983).

Kadiyala, Sudha, et al., Poly(phosphoesters): Synthesis, Physico–Chemical Characterization and Biological Response in *Biomedical Applications of Synthetic Biodegradable Polymers*, Chapter 3 (Jeffrey O. Hollinger, ed. 1995).

Pretula, Julia, et al., High–Molecular–Weight Poly(alkylene Phosphonate)s by Consideration of Dialkylphosphonates wth Diols, *Makromol. Chem.* 191, 671–680 (1990).

Wang, Ya Min, et al., In vitro and in vivo evaluation of taxol release from poly(lactic–co–glycolic acid) microspheres containing isopropyl myristate and degradation of the microspheres, *Journal of Controlled Release*, 49 (1997) 157–166.

Alkan–Onyuksel et al.; "A Mixed Micellar Formulation Suitable for the Parenteral Administration of Taxol ", Pharmaceutical Research 11(2): 206–212 (Feb. 1994).

Burt et al.; "Controlled Delivery of Taxol From Microspheres Composed of a Blend of Ethyllene–Vinyl Acetate Copolymer and Poly (d,/–lactic acid)", Cancer Letters 88(1) : 73–79 (1995).

Demetrick et al.; "The Development of a Novel Intraperitoneal Tumor–Seeding Prophylactic", The American Journal of Surgery 173:403–406 (May 1997).

Dordunoo, et al.; "Release of Taxol from Poly(ϵ–Caprolactone) Pastes: effect of Water–soluble additives", Journal of Controlled Release 44: 87–94 (1997).

Francis et al.; "Phase I Feasibility and Pharmacologic Study of Weekly Intraperitoneal Paclitaxel: A Gynecologic Oncology Group Pilot Study", Journal of Clinical Oncology 13 (12): 2961–2967 (Dec. 1995).

Hagiwara et al.; "Pharmacologic Effects of Cisplatin Microspheres on Peritoneal Carcinomatosis in Rodents", Cancer 71(3):844–850 (Feb. 1, 1993).

Jameela et al.; "Antitumour Activity of Mitoxantroneloaded Chitosan Microspheres Against Ehrlich Ascites Carcinoma", J. Pharm. Pharmacol. 48: 685–688 (1996).

Kumagai, et al.; "Improvement of Intraperitoneal Chemotherapy for Rat Ovarian Cancer Using Cisplatin–Containing Microspheres", Jpn. J. Cancer Res. 87: 412–417 (Apr. 1996).

Mao et al.; "Synthesis and Biological Properties of Polymer Immunoadjuvants", Polymer Journal 25(5): 499–505 (1993).

Owusu–Ababio et al.; "Efficacy of Sustained Release Ciprofloacin Microspheres Against Device–associated *Pseudomonas Aeruginasa* Biofilm Infection in a Rabbit Peritoneal Model", J. Med. Microbiol. 43:368–376 (1995).

Pec et al.; "Biological Activity–Urease Formulated in Poloxamer 407 After Intraperitoneal Injection in the Rat"; Journal of Pharmaceutical Sciences, 81; 626–630 (Jul. 1992).

Sharma et al.; "Antitumor Efficacy of Taxane Liposomes on a Human Ovarian Tumor Xenograft in Nude Athymic Mice", Journal of Pharmaceutical Sciences 84(12): 1400–1404 (Dec. 1995).

Sharma et al.; "Novel Taxol Formulation: Polyvinylpyrrolidone Nanoparticle–Encapsulated Taxol for Drug Delivery in Cancer Therapy", Oncology Reseach 8(7/8): 281–286 (1996).

Wang et al.; "Preparation and Characterization of Poly(lactic–co–glycolic acid) Microspheres for Targeted Delivery of a Novel Anticancer Agent, Taxol", Chem. Pharm. Bull. 44 (10): 19351940 (1996).

Wang et al.; "In Vitro and in Vivo Evaluation of Taxol Release from Poly (lactic–coglycolic acid) Microspheres Containing Isopropyl Myristate and Degradation of the Microspheres", Journal of Controlled Release 49: 157–166 (1997).

Winternitz, et al.; "Development of a Polymeric Surgical Paste Formulation for Taxol", PHREEB 13(3): 368–375 (1996).

Zhang et al.; "Development of Biodegradable Polymeric Paste Formulations for Taxol: an In Vitro and In Vivo Study", International Journal of Pharmaceutics 137: 199–208( 1996).

* cited by examiner

80/20-B, DMSO
OBSERVE H1
 FREQUENCY 399.952 MHz
 SPECTRAL WIDTH 5000.0 Hz
 ACQUISITION TIME 3.744 sec
 RELAXATION DELAY 0.000 sec
 PULSE WIDTH 7.0μsec
 AMBIENT TEMPERATURE
 NO. REPETITIONS 12
DOUBLE PRECISION ACQUISITION
DATA PROCESSING
 FT SIZE 65536
TOTAL ACQUISITION TIME 1 minute

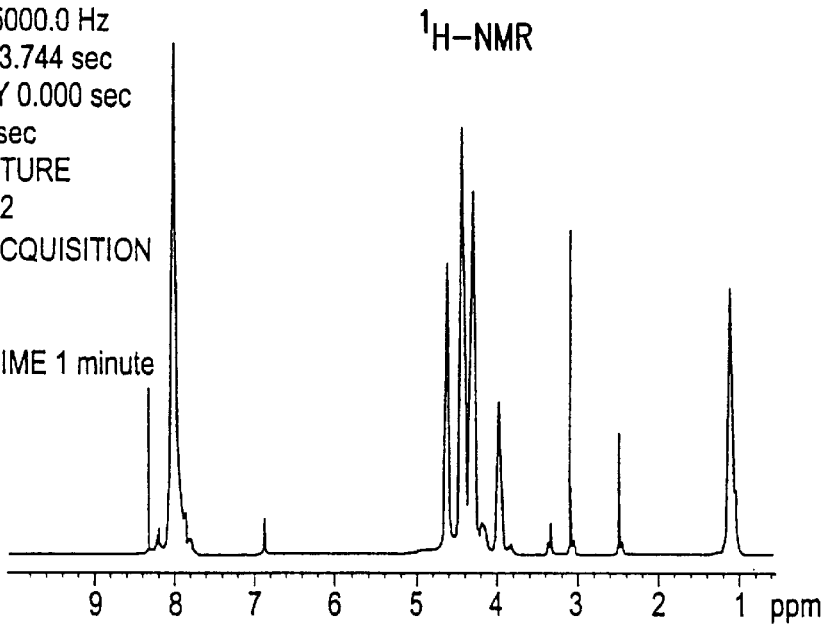

FIG.1A

80/20-B,BB, DMSO
OBSERVE P31
 FREQUENCY 161.903 MHz
 SPECTRAL WIDTH 16000.0 Hz
 ACQUISITION TIME 0.800 sec
 RELAXATION DELAY 0.000 sec
 PULSE WIDTH 10.0μsec
 TEMPERATURE 37.0°C
 NO. REPETITIONS 77
DECOUPLE H1
 HIGH POWER 33
 DECOUPLER CONTINUOUSLY ON
 WALTZ16 MODULATED
DOUBLE PRECISION ACQUISITION
DATA PROCESSING
 LINE BROADENING 15.0Hz
 FT SIZE 32768
TOTAL ACQUISITION TIME 1 minute

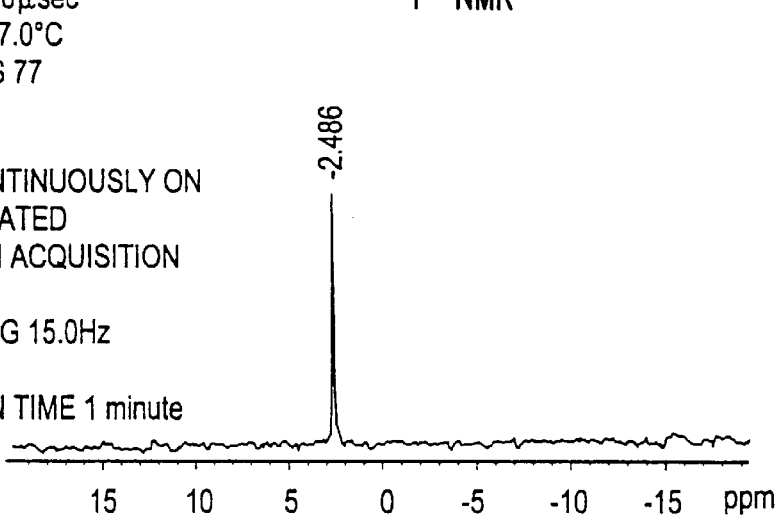

FIG.1B

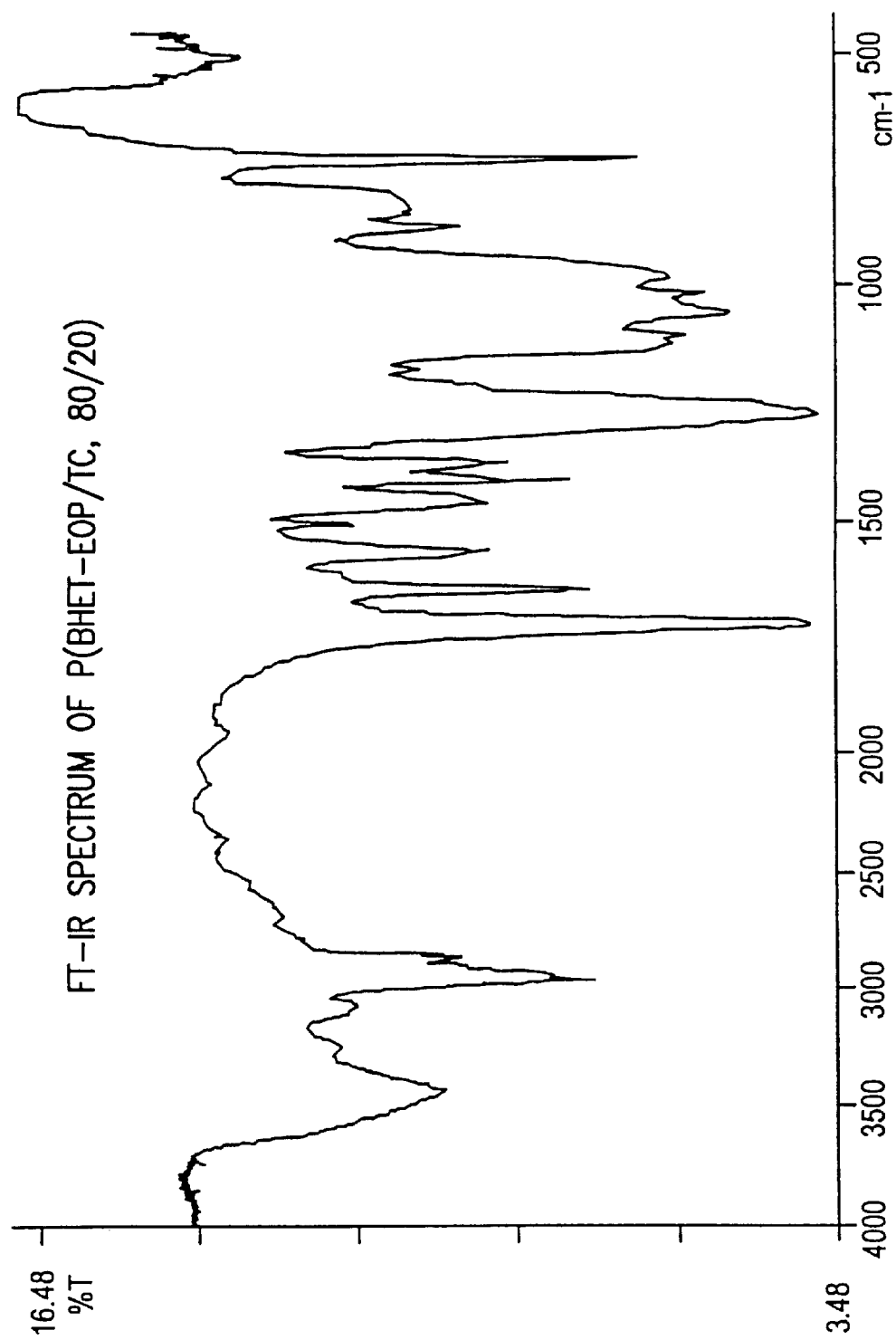

MOLECULAR WEIGHT AND ELEMENTAL ANALYSIS

| Polymer | Mn (VPO) | Mw/Mn (GPC) | Elemental Analysis; Found (Theory) | | |
|---|---|---|---|---|---|
| | | | C (%) | H (%) | P (%) |
| P(BHET-EOP/TC, 80/20) | 7918 | 6119 /2219 | 49.61 (51.82) | 4.95 (4.81) | 6.24 (7.03) |
| P(BHET-HOP/TC, 90/10) | 6364 | 4201 /1587 | 51.67 (53.11) | 5.99 (5.90) | 6.26 (6.77) |

P(BHET-EOP/TC 80/20): CONTROLLED DELIVERY OF HYDROPHOBIC SMALL MOLECULES

BIOCOMPATIBILITY: HISTOPATHOLOGICAL ANALYSIS

| | Inflammatory Response at the Site of Implantation (i.m.) | | | | | |
|---|---|---|---|---|---|---|
| Polymer | 3 D | 7 D | 14 D | 1 M | 2 M | 4 M |
| P(LAEG-EOP) | SI (130) | SI (123) | SI (180) | SI (198) | SI (106) | SI (99) |
| PLGA(RG755) | SI (148) | SI (98) | SI (137) | SI (105) | SI (94) | SI (43) |
| Score: | No Irritation (0) | Slight Irritation (0-200) | Mild Irritation (200-400) | Moderate Irritation (400-600) | Severe Irritation (>600) | |

METHODS FOR TREATING OVARIAN CANCER, POLY (PHOSPHOESTER) COMPOSITIONS, AND BIODEGRADABLE ARTICLES FOR SAME

BACKGROUND OF THE INVENTION

1. Field of the Invention

The present invention relates to methods for treating ovarian cancer, in particular those pertaining to the extended release of an antineoplastic agent from biodegradable poly (phosphoester) compositions.

2. Description of the Prior Art

Antineoplastic agents, such as paclitaxel, have sometimes been used to treat ovarian cancer. For example, those in the art have attempted to administer paclitaxel in normal saline by infusion into the peritoneal cavity of women having ovarian cancer as a prolonged series of weekly treatments. Francis et al., "Phase I Feasibility and Pharmacologic Study of Weekly Intraperitoneal Paclitaxel: A Gynecologic Oncology Group Pilot Study", *J. of Clinical Oncology*, 13:12, 2961–67 (1995). However, problems with multiple toxicities, such as abdominal pain, nausea, vomiting, leukopenia, and fatigue, are often encountered with the high fluid volumes and drug dosages required for efficacy with this approach. Further, the repeated dosing and attendant discomfort is often inconvenient and, sometimes, even unacceptable for patients.

Thus, there exists a need for a method of effecting the in vivo, controlled release of a variety of different antineoplastic agents into the peritoneum, whether they are small hydrophobic drugs, such as paclitaxel, or large and bulky bio-macromolecules, such as therapeutically useful proteins. Preferably, effective release of the antineoplastic agent should occur without requiring the presence of significant amounts of a physiologically acceptable fluid vehicle, such as normal saline or an organic solvent. There is also a continuing need for biodegradable polymer compositions that may provide extended release in such a way that trauma to the surrounding soft tissues can be minimized.

Biocompatible polymeric materials have been used in various therapeutic drug delivery and medical implant applications. If a medical implant is intended for use as a drug delivery or other controlled-release system, using a biodegradable polymeric carrier is one effective means to deliver the therapeutic agent locally and in a controlled fashion, see Langer et al., "Chemical and Physical Structures of Polymers as Carriers for Controlled Release of Bioactive Agents", *J. Macro. Science, Rev. Macro. Chem. Phys.*, C23(1), 61–126 (1983). In this way, less total drug is required, and toxic side effects can be minimized.

Polymers have been used for some time as carriers of therapeutic agents to effect a localized and sustained release. See Leong et al., "Polymeric Controlled Drug Delivery", *Advanced Drug Delivery Rev.*, 1:199–233 (1987); Langer, "New Methods of Drug Delivery", *Science*, 249:1527–33 (1990) and Chien et al., *Novel Drug Delivery Systems* (1982). Such delivery systems offer the potential of enhanced therapeutic efficacy and reduced overall toxicity. Examples of classes of synthetic polymers that have been studied as possible solid biodegradable materials include polyesters (Pitt et al., "Biodegradable Drug Delivery Systems Based on Aliphatic Polyesters: Applications to Contraceptives and Narcotic Antagonists", *Controlled Release of Bioactive Materials*, 19–44 (Richard Baker ed., 1980); poly(amino acids) and pseudo-poly(amino acids) (Pulapura et al. "Trends in the Development of Bioresorbable Polymers for Medical Applications", *J. Biomaterials Appl.*, 6:1, 216–50 (1992); polyurethanes (Bruin et al., "Biodegradable Lysine Diisocyanate-based Poly(Glycolide-co-ε Caprolactone)-Urethane Network in Artificial Skin", *Biomaterials*, 11:4, 291–95 (1990); polyorthoesters (Heller et al., "Release of Norethindrone from Poly(Ortho Esters)", *Polymer Engineering Sci.*, 21:11, 727–31 (1981); and polyanhydrides (Leong et al., "Polyanhydrides for Controlled Release of Bioactive Agents", *Biomaterials* 7:5, 364–71 (1986).

Polymers having phosphate linkages, called poly (phosphates), poly(phosphonates) and poly(phosphites), are known. See Penczek et al., *Handbook of Polymer Synthesis*, Chapter 17: "Phosphorus-Containing Polymers", (Hans R. Kricheldorf ed., 1992). The respective structures of these three classes of compounds, each having a different side chain connected to the phosphorus atom, are as follows:

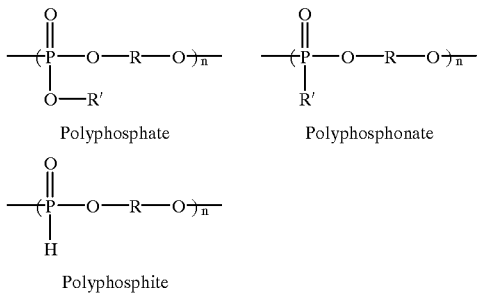

The versatility of these polymers comes from the versatility of the phosphorus atom, which is known for a multiplicity of reactions. Its bonding can involve the 3p orbitals or various 3s-3p hybrids; spd hybrids are also possible because of the accessible d orbitals. Thus, the physicochemical properties of the poly(phosphoesters) can be readily changed by varying either the R or R' group. The biodegradability of the polymer is due primarily to the physiologically labile phosphoester bond in the backbone of the polymer. By manipulating the backbone or the side chain, a wide range of biodegradation rates are attainable.

An additional feature of poly(phosphoesters) is the availability of functional side groups. Because phosphorus can be pentavalent, drug molecules or other biologically active substances can be chemically linked to the polymer. For example, drugs with —O—carboxy groups may be coupled to the phosphorus via a phosphoester bond, which is hydrolyzable. See, Leong, U.S. Pat. Nos. 5,194,581 and 5,256, 765. The P—O—C group in the backbone also lowers the glass transition temperature of the polymer and, importantly, confers solubility in common organic solvents, which is desirable for easy characterization and processing.

Copending U.S. application Ser. No. 09/053,648 and WO 98/44021 disclose biodegradable terephthalate polyester-poly(phosphate) compositions; U.S. application Ser. No. 09/053,649 and WO 98/44020 disclose biodegradable compositions containing polymers chain-extended by phosphoesters; and U.S. application Ser. No. 09/070,204 and International Application No. PCT/US98/09185 disclose biodegradable compositions comprising poly(cycloaliphatic phosphoester) compounds. However, none of these disclosures suggests the specific use of biodegradable poly (phosphoester) compositions for treating ovarian cancer specifically.

Thus, there remains a need for new methods and materials for the difficult problem of successfully treating ovarian cancer with a minimum of discomfort, toxicities and prolonged, periodic re-dosing.

SUMMARY OF THE INVENTION

It has now been discovered that biodegradable polymer compositions comprising:

(a) at least one antineoplastic agent and
(b) a biodegradable polymer comprising the recurring monomeric units shown in formula I:

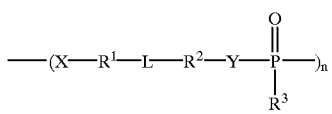

wherein X is —O— or —$NR^4$—, where $R^4$ is H or alkyl;
Y is —O—, —S— or —$NR^4$—; each of $R^1$ and $R^2$ is a divalent organic moiety;
L is a divalent, branched or straight chain aliphatic group having 1–20 carbon atom, a cycloaliphatic group, or a group having the formula:

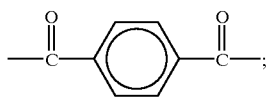

$R^3$ is selected from the group consisting of H, alkyl, alkoxy, aryl, aryloxy, heterocyclic or heterocycloxy; and
n is about 5–5,000;

are suitable for intraperitoneal administration to treat a mammalian subject having ovarian cancer. These polymer compositions provide extended release of the antineoplastic agent within the peritoneum of the subject. Moreover, the polymer composition of the invention increases the median survival rate from the cancer by at least about 10%, as compared with the median survival rate obtained by administration of a composition comprising the same dosage of the antineoplastic agent without the biodegradable polymer of the invention.

The invention also comprises a solid article suitable for insertion into the peritoneum to treat a mammalian subject having ovarian cancer, the article comprising a biodegradable polymer composition comprising:

(a) at least one antineoplastic agent and
(b) a biodegradable polymer comprising the recurring monomeric units shown above in formula I.

In yet another embodiment of the invention, a method is provided for treating a mammalian subject having ovarian cancer by the extended release of an antineoplastic agent, the method comprising the steps of:

(a) combining the antineoplastic agent with a biodegradable polymer having the recurring monomeric units shown above in formula I to form a composition; and
(b) inserting the composition in vivo into the peritoneum of the subject, such that the inserted composition is in at least partial contact with an ovarian cancer tumor, wherein the median survival rate from the cancer is increased by at least about 10%, as compared with the median survival rate obtained by administration of a composition comprising the same dosage of the antineoplastic agent without the biodegradable polymer.

The compositions of the invention can be used to deliver a wide variety of antineoplastic agents, for example, from hydrophobic drugs, such as paclitaxel, to large water-soluble macromolecules, such as proteins, over an extended period of time without necessitating significant volumes of a delivery fluid. The methods of the invention can thus be used to significantly increase the time period over which an effective dose of the antineoplastic agent is released and increases the survival time of subjects treated by the method to an unexpected degree. Further, the serious disease of ovarian cancer can be therapeutically managed with a minimum of side effects and without the unpleasantness and discomfort of a periodic series of parenteral treatments introducing significant amounts of fluid into the peritoneum.

BRIEF DESCRIPTION OF THE DRAWINGS

FIG. 1A shows the $^1$H-NMR spectrum,
and
FIG. 1B shows the $^{31}$P-NMR spectrum for P(BHET-EOP/TC, 80/20).
FIG. 2 shows the FT-IR spectrum for P(BHET-EOP/TC, 80/20).

FIG. 22 shows biocompatibility data for polymers of the invention.

DETAILED DESCRIPTION OF THE INVENTION

Polymeric Compositions of the Invention

Figures 3A, 3B:
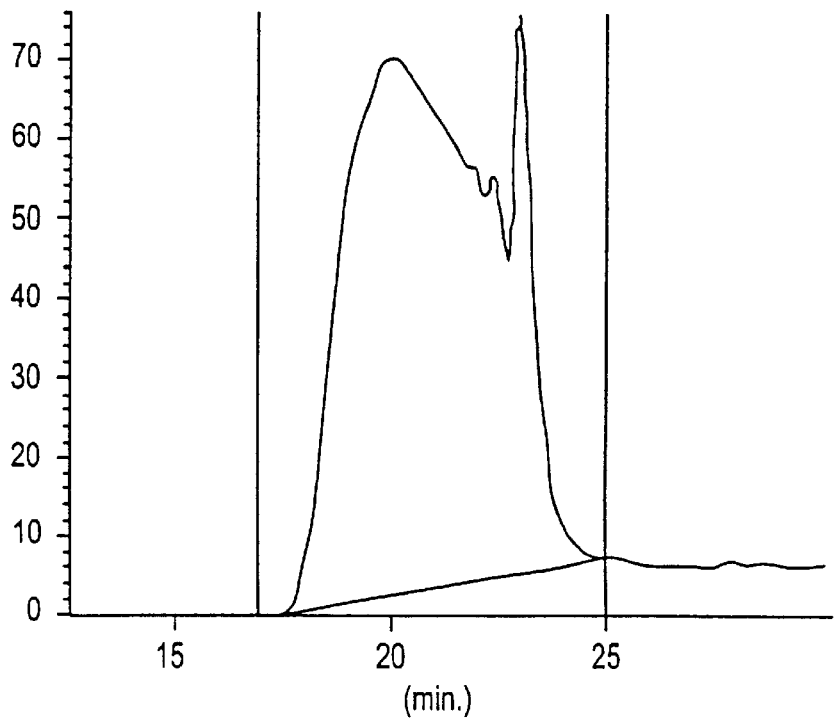
FIG. 3A shows the molecular weights and elemental analyses for P(BHET-EOP/TC, 80/20) and P(BHET-HOP/TC, 90/10)
FIG. 3B shows the GPC chromatogram for P(BHET-EOP/TC, 80/20).

As used herein, the expression "a mammalian subject" refers to any mammalian subject, such as mice, rats, guinea pigs, cats, dogs, human beings, cows, horses, sheep, or other livestock. The expression "a mammalian subject having ovarian cancer" includes, but is not limited to, subjects suffering from current symptoms of this disease; subjects who are recovering from other modes of treatment for the disease, such as surgery, chemotherapy, or other treatment; and subjects simply believed to be at greater than average risk for ovarian cancer, such as those who have at least partially recovered from the disease in the past or those subjects having a significant number of female relatives diagnosed as having or having had the disease.

As used herein, the term "treating" includes:

(i) preventing a disease, disorder or condition from occurring in an animal which may be predisposed to the disease, disorder and/or condition but has not yet been diagnosed as having it;

(ii) inhibiting the disease, disorder or condition, i.e., arresting its development; and (iii) relieving the disease, disorder or condition, i.e., causing regression of the disease, disorder and/or condition.

The term "aliphatic" refers to a linear, branched or cyclic alkane, alkene, or alkyne. Preferred linear or branched aliphatic groups in the poly(cycloaliphatic phosphoester) composition of the invention have from about 1 to 20 carbon atoms. Preferred cycloaliphatic groups may have one or more sites of unsaturation, i.e., double or triple bonds, but are not aromatic in nature.

As used herein, the term "aryl" refers to an unsaturated cyclic carbon compound with 4n+2 π electrons. As used herein, the term "heterocyclic" refers to a saturated or unsaturated ring compound having one or more atoms other than carbon in the ring, for example, nitrogen, oxygen or sulfur. "Heteroaryl" refers to a heterocyclic compound with 4n+2 electrons.

As used herein, the term "non-interfering substituent" means a substituent that does react with the monomers; does not catalyze, terminate or otherwise interfere with the polymerization reaction; and does not react with the resulting polymer chain through intra- or inter-molecular reactions.

The biodegradable and injectable polymer composition of the invention comprises a polymer having the recurring monomeric units shown in formula I:

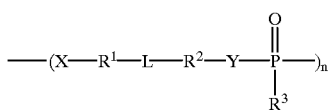

I wherein X is —O— or —NR⁴—, where R⁴ is H or alkyl, such as methyl, ethyl, 1,2-dimethylethyl, n-propyl, isopropyl, 2-methylpropyl, 2,2-dimethylpropyl or tert-butyl, n-pentyl, tert-pentyl, n-hexyl, n-heptyl and the like.

The group Y in formula I is —O—, —S— or —NR⁴-, where R⁴ is as defined above.

Each of $R^1$ and $R^2$ can be any divalent organic moiety, which may be either unsubstituted or substituted with one or more non-interfering substituents, so long as the moiety and its substituents do not interfere undesirably with the polymerization, copolymerization, or biodegradation reactions of the polymer. Specifically, each of $R^1$ and $R^2$ can be a branched or straight chain aliphatic group, preferably having about 1–20 carbon atoms. For example, $R^1$ and $R^2$ can be alkylene, such as methylene, ethylene, 1-methylethylene, 1,2-dimethylethylene, n-propylene, isopropylene, 2-methylpropylene, 2,2'-dimethylpropylene or tert-butylene, n-pentylene, tert-pentylene, n-hexylene, n-heptylene, n-octylene, n-nonylene, n-decylene, n-undecylene, n-dodecylene, and the like.

$R^1$ and $R^2$ can also be alkenylene, such as ethenylene, propenylene, 2-vinylpropenylene, n-butenylene, 3-ethenylbutylene, n-pentenylene, 4-(3-propenyl)hexylene, n-octenylene, 1-(4-butenyl)-3-methyldecylene, dodecenylene, 2-(3-propenyl)dodecylene, hexadecenylene, and the like. $R^1$ and $R^2$ can also be alkynylene, such as ethynylene, propynylene, 3-(2-ethynyl)pentylene, n-hexynylene, octadecenynylene, 2-(2-propynyl)decylene, and the like.

$R^1$ and $R^2$ can also be an aliphatic group, such as an alkylene, alkenylene or alkynylene group, substituted with a non-interfering substituent, for example, a hydroxy, halogen or nitrogen group. Examples of such groups include, but are not limited to, 2-chloro-n-decylene, 1-hydroxy-3-ethenylbutylene, 2-propyl-6-nitro-10-dodecynylene and the like.

Further, $R^1$ and $R^2$ can be a cycloaliphatic group, such as cyclopentylene, 2-methylcyclopentylene, cyclohexylene, cyclohexenylene and the like. Each of $R^1$ and $R^2$ can also be a divalent aromatic group, such as phenylene, benzylene, naphthalene, phenanthrenylene, and the like, or a divalent aromatic group substituted with a non-interfering substituent. Further each of $R^1$ and $R^2$ can be a divalent heterocyclic group, such as pyrrolylene, furanylene, thiophenylene, alkylene-pyrrolylene-alkylene, pyridylene, pyridinylene, pyrimidinylene and the like, or may be any of these substituted with a non-interfering substituent.

Preferably, $R^1$ and $R^2$ have from about 1–20 carbon atoms and are an alkylene group, a cycloaliphatic group, a phenylene group, or a divalent group having the formula:

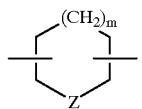

wherein Z is oxygen, nitrogen, or sulfur, and m is 1 to 3. More preferably, each of $R^1$ and $R^2$ is a branched or straight chain alkylene group having from 1 to 7 carbon atoms. Most preferably, each of $R^1$ and $R^2$ is a methylene, ethylene group, n-propylene, 2-methyl-propylene, or a 2,2'-dimethylpropylene group.

In one embodiment of the invention, either $R^1$, $R^2$ or both $R^1$ and $R^2$, can be an antineoplastic agent in a form capable of being released in a physiological environment. When the antineoplastic agent part of the poly(phosphoester) backbone in this way, it is released as the polymeric matrix formed by the composition of the invention degrades.

L in the polymer composition of the invention can be any divalent, branched or straight chain aliphatic group having 1–20 carbon atom, a cycloaliphatic group, or a group having the formula:

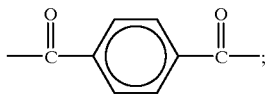

When L is a branched or straight chain alkylene group, it is preferably an alkylene group having from 1 to 7 carbon atoms, such as 2-methylmethylene or ethylene. When L is a cycloaliphatic group, it may be any divalent cycloaliphatic group so long as it does not interfere with the polymerization or biodegradation reactions of the polymer of the composition. Specific examples of useful unsubstituted and substituted cycloaliphatic L groups, include cycloalkylene groups such as cyclopentylene, 2-methylcyclopentylene, cyclohexylene, 2-chlorocyclohexylene, and the like; cycloalkenylene groups, such as cyclohexenylene; and cycloalkylene groups having fused or bridged additional ring structures on one or more sides, such as tetralinylene, decalinylene, and norpinanylene; or the like.

$R^3$ in the polymer composition of the invention is selected from the group consisting of H, alkyl, alkoxy, aryl, aryloxy, heterocyclic and heterocycloxy residues.

When $R^3$ is alkyl or alkoxy, it preferably contains about 1 to about 20 carbon atoms, even more preferably about 1 to about 15 carbon atoms and, most preferably about 1–7 carbon atoms. Examples of such groups include methyl, methoxy, ethyl, ethoxy, n-propyl, isopropoxy, n-butoxy, t-butyl, —$C_8H_{17}$; alkyl substituted with a non-interfering substituent, such as halogen, alkoxy or nitro; alkyl conjugated to a biologically active substance to form a pendant drug delivery system; and the like.

When $R^3$ is aryl or the corresponding aryloxy group, it typically contains from about 5 to about 14 carbon atoms, preferably about 5 to 12 carbon atoms and, optionally, can contain one or more rings that are fused to each other. Examples of particularly suitable aromatic groups include phenyl, phenoxy, naphthyl, anthracenyl, phenanthrenyl and the like.

When $R^3$ is heterocyclic or heterocycloxy, it typically contains from about 5 to 14 ring atoms, preferably from about 5 to 12 ring atoms, and one or more heteroatoms. Examples of suitable heterocyclic groups include furan, thiophene, pyrrole, isopyrrole, 3-isopyrrole, pyrazole, 2-isoimidazole, 1,2,3-triazole, 1,2,4-triazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2, 3,5-oxatriazole, 1,2,3-dioxazole, 1,2,4-dioxazole, 1,3,2-dioxazole, 1,3,4-dioxazole, 1,2,5-oxatriazole, 1,3-oxathiole, 1,2-pyran, 1,4-pyran, 1,2-pyrone, 1,4-pyrone, 1,2-dioxin, 1,3-dioxin, pyridine, N-alkyl pyridinium, pyridazine, pyrimidine, pyrazine, 1,3,5-triazine, 1,2,4-triazine, 1,2,3-triazine, 1,2,4-oxazine, 1,3,2-oxazine, 1,3,5-oxazine, 1,4-oxazine, o-isoxazine, p-isoxazine, 1,2,5-oxathiazine, 1,2,6- oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando[3,4-b]-pyrrole, isoindazole, indoxazine, benzoxazole, anthranil, 1,2-benzopyran, 1,2-benzopyrone, 1,4-benzopyrone, 2,1-benzopyrone, 2,3-benzopyrone, quinoline, isoquinoline, 12,-benzodiazine, 1,3-benzodiazine, naphthpyridine, pyrido[3,4-b]-pyridine, pyrido[3,2-b]-pyridine, pyrido[4,3-b]pyridine, 1,3,2-benzoxazine, 1,4,2-benzoxazine, 2,3,1-benzoxazine, 3,1,4-benzoxazine, 1,2-benzisoxazine, 1,4-benzisoxazine, carbazole, xanthrene, acridine, purine, and the like. Preferably, when $R^3$ is heterocyclic or heterocycloxy, it is selected from the group consisting of furan, pyridine, N-alkylpyridine, 1,2,3- and 1,2,4-triazoles, indene, anthracene and purine rings.

a period greater than about three weeks and, most preferably, is for a period greater than four weeks, for example, from four weeks to a year.

Further, use of the composition in accordance with the method of the invention increases the median survival rate from the cancer by at least about 10%, as compared with the median survival rate obtained by administration of a composition comprising the same dosage of antineoplastic agent without the biodegradable polymer of the invention. Preferably, the median survival rate is increased by at least about 20%, more preferably by at least 30% and, most preferably, by a factor of at least about 40%.

The polymer used in the composition of the invention is preferably selected from the group consisting of:

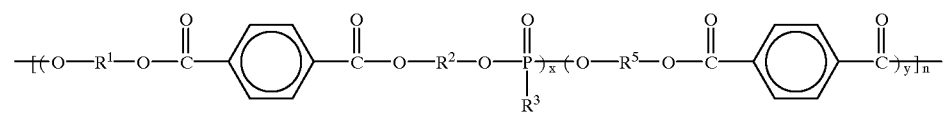

II

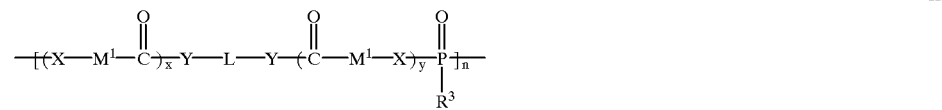

III

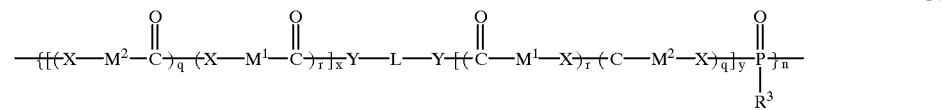

IV and

V

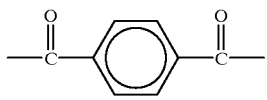

wherein $R^1$, $R^2$, $R^3$ and n are as defined above.

In polymers of formula II, $R^5$ is selected from the same groups as for $R^1$ and $R^2$, and L is preferably a group having the formula:

In a particularly preferred embodiment, $R^3$ is an alkyl group, an alkoxy group, a phenyl group, a phenoxy group, or a heterocycloxy group and, even more preferably, an alkoxy group having from 1 to 10 carbon atoms. Most preferably, $R^3$ is an ethoxy or hexyloxy group.

Alternatively, the side chain $R^3$ can be the antineoplastic agent or some other biologically active substance pendently attached to the polymer backbone, for example by ionic or covalent bonding. In this pendant system, the antineoplastic agent or other biologically active substance is released as the bond connecting $R^3$ with the phosphorous atom is cleaved under physiological conditions.

The number "n" can vary greatly depending on the biodegradability and the release characteristics desired in the polymer, but typically varies between about 5 and 1,000. Preferably, n is from about 5 to about 500 and, most preferably, is from about 5 to about 200.

When used in accordance with the method of the invention, the polymer composition provides extended release of the antineoplastic agent into the peritoneum of a subject having ovarian cancer, preferably for a period greater than one week, more preferably for a period greater than two weeks. Even more preferably, this time extends for The molar ratio of x:y in formula II can vary greatly depending on the desired solubility of the polymer, the desired glass transition temperature (Tg), the desired stability of the polymer, the desired stiffness of the final polymers, and the biodegradability and the release characteristics desired in the polymer. However, the molar ratio of x:y typically varies between about 20:0 and 1:20. When y is 0, the polymer formed is a homopolymer. Preferably, however, the ratio x:y is from about 1:15 to about 15:1, more preferably, from about 10:1 to about 1:1.

The most common way of controlling the molar ratio of x:y is to vary the feed ratio of the "x" portion to the "y" portion when synthesizing the polymer. Feed ratios can easily vary from 99: to 1:99, for example, 95:5, 90:10, 85:15, 80:20, 75:25, 70:30, 65:35, 60:40, 55:45, 50:50, 45:55, 20:80, 15:85, and the like. Preferably, the monomer feed ratio varies from about 90:10 to about 50:50, even more preferably from about 80:20 to about 50:50 and, most preferably, from about 80:20 to about 50:50.

Preferably, when the biodegradable polymer has formula II, $R^3$ is alkoxy, aryloxy or heterocycloxy; x is about 0.1 to 30, more preferably about 0.2 to 20, most preferably $\geq 1$ (for example, about 2–20); and y is 2.

In preferred polymers of formula III and IV:

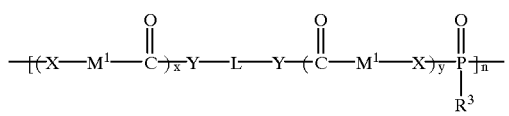

III

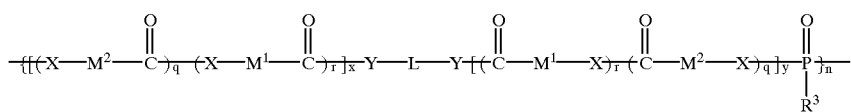

IV $M^1$ and $M^2$ are each independently (1) a branched or straight chain aliphatic group having from about 1–20 carbon atoms, even more preferably from about 1–7 carbon atoms; or (2) a branched or straight chain, oxy-, carboxy- or amino-aliphatic group having from about 1–20 carbon atoms, such as ethoxylene, 2-methylethoxylene, propoxylene, butoxylene, pentoxylene, dodecyloxylene, hexadecyloxylene, and the like;

each of x and y is about 1 to 1,000;

the molar ratio of x:y can vary greatly depending on the biodegradability and the release characteristics desired in the polymer but, typically, is about 1;

the molar ratio n: (x or y) can vary greatly depending on the biodegradability and the release characteristics desired in the polymer, but typically varies between about 200:1 and 1:200, preferably 100:1 and 1:100, more preferably from about 50:1 to about 1:50; and the molar ratio q:r can also vary greatly depending on the biodegradability and the release characteristics desired in the polymer, but typically varies between about 1:200 and 200:1, preferably between about 1:150 to about 150:1 and, most preferably, between about 1:99 and 99:1.

In formula III, each of $M^1$ and L preferably h from 1 to 7 carbon atoms. More preferably, $M^1$ is an ethylene group or a methyl-substituted methylene group, and L is an ethylene group.

In formula IV, each of $M^1$ and $M^2$ is preferably a branched or straight chain alkylene or alkoxylene group, more preferably having from 1–20 carbon atoms. Even more preferably, at least one of $M^1$ and $M^2$ is an alkylene or alkoxylene group having a formula selected from the group consisting of $-(CH_2)_a-$, $-(CH_2)_a-O-$, and $-(CH_2)_a-O-(CH_2)_b-$, wherein each of a and b is 1–7.

When either $M^1$ and $M^2$ is a branched or straight chain, oxy-aliphatic group having from 1–20 carbon atoms it can also be, for example, a dioxyalkylene group such as such as dioxymethylene, dioxyethylene, 1,3-dioxypropylene, 2-methoxy-1,3-dioxypropylene, 1,3-dioxy-2-methylpropylene, dioxy-n-pentylene, dioxy-n-octadecylene, methoxylene-methoxylene, ethoxylene-methoxylene, ethoxylene-ethoxylene, ethoxylene-1-propoxylene, butoxylene-n-propoxylene, pentadecyloxylene-methoxylene, and the like. When $M^1$ and $M^2$ is a branched or straight chain, dioxo-aliphatic group, preferably it has the formula $-O-(CH_2)_a-O-$ or $-O-(CH_2)_a-O-(CH_2)_b-$, wherein each of a and b is from 1–7.

When either $M^1$ or $M^2$ is a branched or straight chain, carboxy-aliphatic group having from 1–20 carbon atoms, it can also be, for example, a divalent carboxylic acid ester such as the divalent radical corresponding to methyl formate, methyl acetate, ethyl acetate, n-propyl acetate, isopropyl acetate, n-butyl acetate, ethyl propionate, allyl propionate, t-butyl acrylate, n-butyl butyrate, vinyl chloroacetate, 2-methoxycarbonyl cyclohexanone, 2-acetoxycyclohexanone, and the like. When $M^1$ or $M^2$ is a branched or straight chain, carboxy-aliphatic group, it preferably has the formula $-CHR'-CO-O-CHR''-$, wherein R' and R" are each independently H, alkyl, alkoxy, aryl, aryloxy, heterocyclic or heterocycloxy.

When either $M^1$ or $M^2$ is a branched or straight chain, amino-aliphatic group having from 1–20 carbon atoms, it can be a divalent amine such as $-CH_2NH-$, $-(CH_2)_2N-$, $-CH_2(C_2H_5)N-$, $-n-C_4H_9-NH-$, $-t-C_4H_9-NH-$, $-CH_2(C_3H_6)N-$, $-C_2H_5(C_3H_6)N-$, $-CH_2(C_8H_{17})N-$, and the like. When $M^1$ or $M^2$ is a branched or straight chain, amino-aliphatic group, it preferably has the formula $-(CH_2)_a-NR'$ where R' is H or lower alkyl, and "a" is from 1 to 7.

Preferably, $M^1$ and/or $M^2$ is an alkylene group having the formula $-O-(CH_2)_a-$ where a is 1 to 7 and, most preferably, is a divalent ethylene group. In another particularly preferred embodiment, $M^1$ and $M^2$ are n-pentylene and the divalent radical corresponding to methyl acetate respectively.

In a preferred embodiment, L in formulas III and IV is a branched or straight chain aliphatic group having from 1–20 carbon atoms, more preferably an alkylene group having from 1 to 7 carbon atoms, such as ethylene or methyl-substituted methylene.

In another particularly preferred polymer of formula IV, $M^1$ and $M^2$ are each an alkylene or alkoxylene group; L is an alkylene group; X is $-O-$; and $R^3$ is an alkoxy group. Most preferably, the biodegradable polymer used in the invention comprises the recurring monomeric units shown in formula VI:

VI

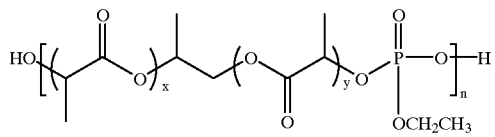

wherein the molar ratio of x:y is about 1;
the molar ratio n:(x or y) is between about 200:1 and 1:200; and
n is about 5–5,000.

When the polymer used has formula V:

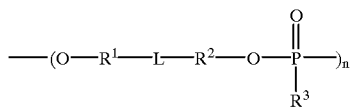

preferably, each of $R^1$ and $R^2$ is independently straight or branched aliphatic, such as a branched or straight chain alkylene group having from 1 to 7 carbon atoms, for example methylene or ethylene, either unsubstituted or substituted with one or more non-interfering substituents;

L is a divalent cycloaliphatic group, such as cyclohexylene, either unsubstituted or substituted with a non-interfering substituent;

$R^3$ is selected from the group consisting of H, alkyl, alkoxy, aryl, aryloxy, heterocyclic or heterocycloxy (preferably alkoxy such as ethoxy or hexyloxy); and n is about 5–5,000, even more preferably 5 to 500.

The molecular weight of the polymer used in the composition of the invention can vary widely, depending on whether a rigid solid state (higher molecular weights) desirable, or whether a flowable or flexible state (lower molecular weights) is desired. Generally, however, weight-average molecular weights (Mw) typically vary from about 2,000 to about 400,000 daltons, preferably from about 2,000 to about 200,000 daltons and, even more preferably, from about 2,000 to 60,000 daltons. Most preferably, the Mw varies between about 10,0000 to 55,000. Number-average molecular weight (Mn) can also vary widely, but generally fall in the range of about 1,000 to about 200,000 daltons, preferably from about 1,000 to about 100,000 daltons and, even more preferably, from about 1,000 to about 50,000 daltons. Most preferably, Mn varies between about 8,000 and 45,000 daltons.

A preferred method to determine molecular weight is by gel permeation chromatography ("GPC"), e.g., mixed bed columns, $CH_2Cl_2$ solvent, light scattering detector, and off-line dn/dc.

The glass transition temperature (Tg) of the polymer used in the invention can vary widely depending upon the degree of branching in $R^1$ and $R^2$, the relative proportion of phosphorous-containing monomer used to make the polymer, and the like. When the article of the invention is a rigid solid, the Tg is preferably within the range of from about −100° C. to about 80° C., even more preferably between about 0 and 50° C. and, most preferably between about 25° C. to about 35° C.

In other embodiments, the Tg is preferably low enough to keep the composition of the invention flowable at body temperature. Then, the glass transition temperature of the polymer used in the invention is preferably about 0 to about 37° C., more preferably from about 0 to about 25° C.

The biodegradable polymer used in the invention is preferably sufficiently pure to be biocompatible itself and remains biocompatible upon biodegradation. By "biocompatible", it is meant that the biodegradation products or the polymer itself are non-toxic and result in only minimal tissue irritation when injected or placed into intimate contact with vasculated tissues. The requirement for biocompatibility is more easily accomplished because the presence of an organic solvent is not required in the polymer composition of the invention.

However, the polymer used in the invention is preferably soluble in one or more common organic solvents for ease of synthesis, purification and handling. Common organic solvents include such solvents as ethanol, chloroform, dichloromethane (dimethylene chloride), acetone, ethyl acetate, DMAC, N-methyl pyrrolidone, dimethylformamide, and dimethylsulfoxide. The polymer is preferably soluble in at least one of the above solvents.

The polymer of the invention can also comprise additional biocompatible monomeric units so long as they do not interfere with the biodegradable characteristics and the desirable flow characteristics of the invention. Such additional monomeric units may offer even greater flexibility in designing the precise release profile desired for targeted drug delivery or the precise rate of biodegradability desired for other applications. When such additional monomeric units are used, however, they should be used in small enough amounts to insure the production of a biodegradable copolymer having the desired physical characteristics, such as rigidity, viscosity, flowability, flexibility or a particular morphology.

Examples of such additional biocompatible monomers include the recurring units found in other poly (phosphoesters), poly(lactides), poly(glycolides), poly (caprolactones), poly(anhydrides), poly(amides), poly (urethanes), poly(esteramides), poly(orthoesters), poly (dioxanones), poly(acetals), poly(ketals), poly(carbonates), poly(orthocarbonates), poly(phos-phazenes), poly (hydroxybutyrates), poly(hydroxy-valerates), poly(alkylene oxalates), poly(alkylene succinates), poly(malic acids), poly (amino acids), poly(vinylpyrrolidone), poly(ethylene glycol), poly-(hydroxycellulose), chitin, chitosan, and copolymers, terpolymers, or combinations or mixtures of the above materials.

When additional monomeric units are used, those which have a lower degree of crystallization and are more hydrophobic are preferred. Especially preferred recurring units with the desired physical characteristics are those derived from poly(lactides), poly(caprolactones), and copolymers of these with glycolide, in which there are more amorphous regions.

General Synthesis of Phosphoester Polymers

The most common general reaction in preparing poly-(phosphates) is a dehydrochlorination between a phosphorodichloridate and a diol according to the following equation:

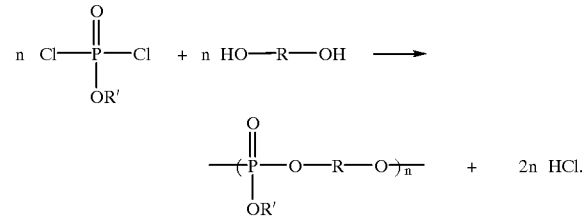

Most poly(phosphonates) are also obtained by condensation between appropriately substituted dichlorides and diols.

Poly(phosphites) have been prepared from glycols in a two-step condensation reaction. A 20% molar excess of a dimethylphosphite is used to react with the glycol, followed by the removal of the methoxyphosphonyl end groups in the oligomers by high temperature.

An advantage of melt polycondensation is that it avoids the use of solvents and large amounts of other additives, thus making purification more straightforward. It can also provide polymers of reasonably high molecular weight. Somewhat rigorous conditions, however, are often required and can lead to chain acidolysis (or hydrolysis if water is present). Unwanted, thermally-induced side reactions, such as crosslinking reactions, can also occur if the polymer backbone is susceptible to hydrogen atom abstraction or oxidation with subsequent macroradical recombination.

To minimize these side reactions, the polymerization can also be carried out in solution. Solution polycondensation requires that both the prepolymer and the phosphorus component be soluble in a common solvent. Typically, a chlorinated organic solvent is used, such as chloroform, dichloromethane, or dichloroethane.

A solution polymerization is preferably run in the presence of equimolar amounts of the reactants and a stoichiometric amount of an acid acceptor, usually a tertiary amine such as pyridine or triethylamine. Reaction times tend to be longer with solution polymerization than with melt polymerization. However, because overall milder reaction conditions can be used, side reactions are minimized, and more sensitive functional groups can be incorporated into the polymer. Moreover, attainment of high molecular weights is less likely with solution polymerization.

Interfacial polycondensation can be used when high reaction rates are desired. The mild conditions used minimize side reactions, and there is no need for stoichiometric equivalence between the diol and dichloridate starting materials as in solution methods. However, hydrolysis of the acid chloride may occur in the alkaline aqueous phase. Sensitive dichloridates that have some solubility in water are generally subject to hydrolysis rather than polymerization. Phase transfer catalysts, such as crown ethers or tertiary ammonium chloride, can be used to bring the ionized diol to the interface to facilitate the polycondensation reaction. The yield and molecular weight of the resulting polymer after interfacial polycondensation are affected by reaction time, molar ratio of the monomers, volume ratio of the immiscible solvents, the type of acid acceptor, and the type and concentration of the phase transfer catalyst.

The purpose of the polymerization reaction is to form a polymer comprising (i) divalent organic recurring units and (ii) phosphoester recurring units. The result can be a homopolymer, a relatively homogeneous copolymer, or a block copolymer that has a somewhat heterogeneous microcrystalline structure. Any one of these three embodiments is well-suited for use as a controlled release medium.

While the process may be in bulk, in solution, by interfacial polycondensation, or any other convenient method of polymerization, preferably, the process takes place under solution conditions. Particularly useful solvents include methylene chloride, chloroform, tetrahydrofuran, dimethyl formamide, dimethyl sulfoxide, toluene, or any of a wide variety of other inert organic solvents.

Particularly when solution polymerization reaction is used, an acid acceptor is advantageously present during the polymerization reaction. A particularly suitable class of acid acceptor comprises tertiary amines, such as pyridine, trimethylamine, triethylamine, substituted anilines and substituted aminopyridines. The most preferred acid acceptor is the substituted aminopyridine 4-dimethylaminopyridine ("DMAP").

In a particularly preferred embodiment of the invention, for example, the biodegradable polymer of formula III or IV is made by a process comprising the steps of:

(a) reacting at least one heterocyclic ring compound having formula VII, VIII or IX:

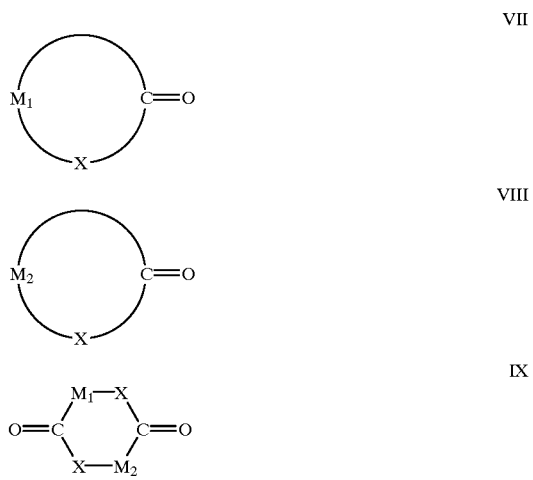

wherein $M^1$, $M^2$ and X are as defined above, with an initiator having the formula:

H—Y—L—Y—H, wherein Y and L are as defined as above, to form a prepolymer of formula X or XI, shown below:

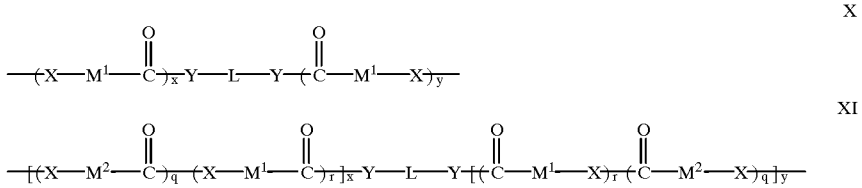

wherein X, $M^1$, $M^2$, Y, L, R, x, y, q and r are as defined above; and (b) further reacting the prepolymer with a phosphorodihalidate of formula XII:

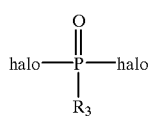

where "halo" is Br, Cl or I; and $R^3$ is as defined above, to form a polymer of formula III or IV.

The function of the first reaction step (a) is to use the initiator to open the ring of the heterocyclic ring compound of formula VII, VIII or IX. Examples of useful heterocyclic compounds of formula VII, VIII or IX include caprolactones, caprolactams, amino acid anhydrides such as glycine anhydride, cycloalkylene carbonates, dioxanones, glycolids, lactides and the like.

When the compound of the invention has formula III, only one heterocyclic ring compound of formula VII, which contains $M^1$, may be used to prepare the prepolymer in step (a). When the compound of the invention has formula IV, then a combination of a heterocyclic compound of formula VII, which contains $M^1$, and a heterocyclic compound of formula VIII, which contains $M^2$ may be used in step (a). Alternatively, when the compound of the invention has formula IV, a single heterocyclic compound of formula IX, which contains both $M^1$ and $M^2$ can be used in step (a).

Examples of suitable initiators include a wide variety of compounds having at least two active hydrogens (H—Y—L—Y—H) where L is a linking group and is defined above, and Y can be —O—, —S— or —NR$^4$, where R$^4$ is as defined above. The linking group L is can be a straight chain group, e.g., alkylene, but it may also be substituted with one or more additional active-hydrogen-containing groups. For example, L may be a straight chain alkylene group substituted with one or more additional alkyl groups, each bearing a activated hydrogen moiety, such as —OH, —SH, or NH$_2$. In this way, various branched polymers can be prepared using the branched active hydrogen initiators to design the resulting polymer such that it has the desired properties. However, when branched polymers are reacted with acid chlorides, cross-linked polymers will result.

The reaction step (a) can take place at widely varying temperatures, depending upon the solvent used, the molecular weight desired, the susceptibility of the reactants to form side reactions, and the presence of a catalyst. Preferably, however, the reaction step (a) takes place at a temperature from about 0 to about +235° C. for melt conditions. Somewhat lower temperatures may be possible with the use of either a cationic or anionic catalyst.

While the reaction step (a) may be in bulk, in solution, by interfacial polycondensation, or any other convenient method of polymerization, preferably, the reaction step (a) takes place under melt conditions.

Examples of particularly useful prepolymers of formula X include:

(i) OH-terminated prepolymer derived from polycaprolactone H—[—O(CH$_2$)$_5$—CO—]$_x$—O—CH$_2$—CH$_2$—O—[—CO—(CH$_2$)$_5$—O—]$_y$—H;

(ii) NH-terminated prepolymer derived from polycaprolactam (Nylon 6)H—[—NH—(CH$_2$)$_5$—CO—]$_x$—NH—CH$_2$—CH$_2$—NH—[—CO—(CH$_2$)$_5$—NH—]$_y$—H;

(iii) OH-terminated prepolymer derived from polylactide H—[—OCH(CH$_3$)—CO—]$_x$—O—CH$_2$—CH$_2$—O—[—CO—CH(CH$_3$)—O—]$_y$—H; and (iv) OH-terminated prepolymer derived from polytrimethylene carbonate H—[—O(CH$_2$)$_3$—O—CO—]$_x$—O—CH$_2$—CH$_2$—O—[—CO—O—(CH$_2$)$_3$—O—]$_y$—H.

Examples of particularly useful prepolymers of formula XI include:

(i) OH-terminated copolymer derived from lactide and glycolide:

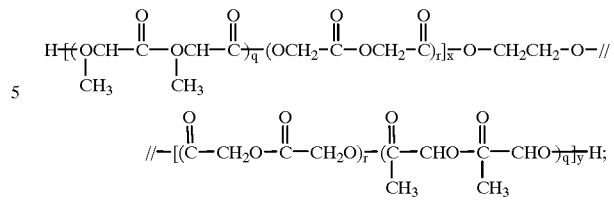

(ii) OH-terminated copolymer derived from lactide and caprolactone:

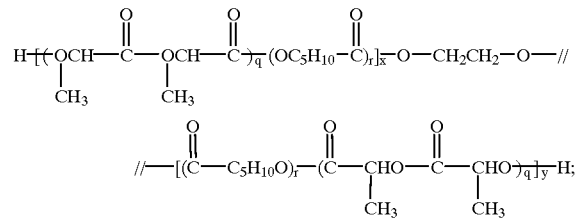

and (iii) OH-terminated copolymer derived from glycolide and caprolactone:

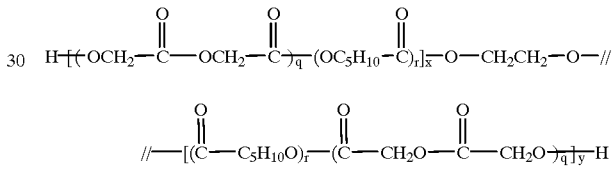

The purpose of the polymerization of step (b) is to form a polymer comprising (i) the prepolymer produced as a result of step (a) and (ii) interconnecting phosphorylated units. The result can be a block copolymer having a microcrystalline structure that is particularly well-suited to use as a controlled release medium.

The polymerization step (b) of the invention usually takes place at a slightly lower temperature than the temperature of step (a), but also may vary widely, depending upon the type of polymerization reaction used, the presence of one or more catalysts, the molecular weight desired, and the susceptibility of the reactants to undesirable side reaction. When melt conditions are used, the temperature may vary from about 0–150° C. However, when the polymerization step (b) is carried out in a solution polymerization reaction, it typically takes place at a temperature between about −40 and 100° C.

Antineoplastic Agent

Generally speaking, the antineoplastic agent of the invention can vary widely depending upon the pharmacological strategy selected for inhibiting, destroying, or preventing the ovarian cancer. The antineoplastic agent may be described as a single entity or a combination of entities. The compositions, articles and methods are designed to be used with antineoplastic agents having high water-solubility, as well as those having low water-solubility, to produce a delivery system that has controlled release rates.

The term antineoplastic agent includes, without limitation, alkylating agents, such as carboplatin and cisplatin; nitrogen mustard alkylating agents; nitrosourea alkylating agents, such as carmustine (BCNU); antimetabolites, such as methotrexate; purine analog antimetabolites; pyrimidine analog antimetabolites, such as fluorouracil (5-FU)

and gemcitabine; hormonal antineoplastics, such as goserelin, leuprolide, and tamoxifen; natural antineoplastics, such as aldesleukin, interleukin-2, docetaxel, etoposide (VP-16), interferon alfa, paclitaxel, and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine. Preferably, the antineoplastic agent is selected from the group consisting of paclitaxel, BCNU, carboplatin and cisplatin. Most preferably, the antineoplastic agent is paclitaxel.

Further, the following additional drugs may also be used in combination with the antineoplastic agent, even if not considered antineoplastic agents themselves: dactinomycin; daunorubicin HCl; docetaxel; doxorubicin HCl; epoetin alfa; etoposide (VP-16); ganciclovir sodium; gentamicin sulfate; interferon alfa; leuprolide acetate; meperidine HCl; methadone HCl; ranitidine HCl; vinblastin sulfate; and zidovudine (AZT). For example, fluorouracil has recently been formulated in conjunction with epinephrine and bovine collagen to form a particularly effective combination.

Still further, the following listing of amino acids, peptides, polypeptides, proteins, polysaccharides, and other large molecules may also be used: interleukins 1 through 18, including mutants and analogues; interferons or cytokines, such as interferons $\alpha$, $\beta$, and $\gamma$; hormones, such as luteinizing hormone releasing hormone (LHRH) and analogues and, gonadotropin releasing hormone (GnRH); growth factors, such as transforming growth factor-$\beta$ (TGF-$\beta$), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-$\alpha$ & $\beta$ (TNF-$\alpha$ & $\beta$); invasion inhibiting factor-2 (IIF-2); bone morphogenetic proteins 1-7 (BMP 1-7); somatostatin; thymosin-$\alpha$-1; $\gamma$-globulin; superoxide dismutase (SOD); complement factors; anti-angiogenesis factors; antigenic materials; and pro-drugs.

In particularly preferred embodiment, the composition of the invention may comprise other biologically active substances, preferably a therapeutic drug or pro-drug, for example, other chemotherapeutic agents, antibiotics, anti-virals, anti-fungals, anti-inflammatories, and anticoagulants, antigens useful for cancer vaccine applications or corresponding pro-drugs.

Various forms of the antineoplastic agents and/or other biologically active agents may be used. These include, without limitation, such forms as uncharged molecules, molecular complexes, salts, ethers, esters, amides, and the like, which are biologically activated when implanted, injected or otherwise placed into the body.

In a particularly preferred embodiment, a biodegradable polymer composition suitable for intraperitoneal administration to treat a mammalian subject having ovarian cancer comprises:

(a) paclitaxel and (b) a biodegradable polymer comprising the recurring monomeric units shown in formula VI:

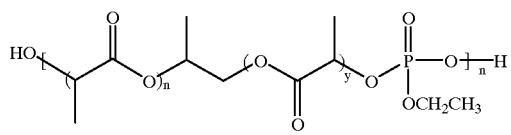

wherein the molar ratio of x:y is about 1;
the molar ratio n:(x or y) is between about 200:1 and 1:200; and
n is about 5–5,000.

Biodegradation and Release Characteristics

Biodegradable polymers differ from non-biodegradable polymers in that they can be degraded during in vivo therapy. This generally involves breaking down the polymer into its monomeric subunits. In principle, the ultimate hydrolytic breakdown products of the polymer used in the invention are a cycloaliphatic diol, an aliphatic alcohol and phosphate. All of these degradation products are potentially non-toxic. However, the intermediate oligomeric products of the hydrolysis may have different properties. Thus, the toxicology of a biodegradable polymer intended for insertion into the body, even one synthesized from apparently innocuous monomeric structures, is typically determined after one or more toxicity analyses.

There are many different ways of testing for toxicity and/or biocompatibility known to those of ordinary skill in the art. A typical in vitro toxicity assay, however, would be performed with live carcinoma cells, such as GT3TKB tumor cells, in the following manner:

Two hundred microliters of various concentrations of the degraded polymer products are placed in 96-well tissue culture plates seeded with human gastric carcinoma cells (GT3TKB) at $10^4$/well density. The degraded polymer products are incubated with the GT3TKB cells for 48 hours. The results of the assay can be plotted as % relative growth vs. concentration of degraded polymer in the tissue-culture well.

Polymers can also be evaluated by well-known in vivo biocompatibility tests, such as by subcutaneous implantation or injection in rats to confirm that the systems hydrolyze without significant levels of irritation or inflammation at the insertion site.

The polymer of formula I is usually characterized by a biodegradation rate that is controlled at least in part as a function of hydrolysis of the phosphoester bond of the polymer. Other factors are also important. For example, the lifetime of a biodegradable polymer in vivo also depends upon its molecular weight, crystallinity, biostability, and the degree of crosslinking. In general, the greater the molecular weight, the higher the degree of crystallinity, and the greater the biostability, the slower biodegradation will be. In addition, the rate of degradation of the polymer can be further controlled by choosing a side chain of differing lengths. Accordingly, degradation times can very widely, preferably from less than a day to several months.

Accordingly, the structure of the side chain can influence the release behavior of compositions comprising a biologically active substance. For example, it is expected that conversion of the phosphate side chain to a more lipophilic, more hydrophobic or bulky group would slow down the degradation process. Thus, release is usually faster from polymer compositions with a small aliphatic group side chain than with a bulky aromatic side chain.

The expression "extended release", as used herein, includes, without limitation various forms of release, such as controlled release, timed release, sustained release, delayed release, long acing, and pulsatile delivery, immediate release that occurs with various rates. The ability to obtain extended release, controlled release, timed release, sustained release, delayed release, long acting, pulsatile delivery or immediate release is performed using well-known procedures and techniques available to the ordinarily skilled artisan. None of these specific techniques or procedures constitute an inventive aspect of this invention.

Polymer Compositions

The antineoplastic agents are used in amounts that are therapeutically effective, which varies widely depending largely on the particular antineoplastic agent being used. The amount of antineoplastic agent incorporated into the composition also depends upon the desired release profile, the concentration of the agent required for a biological effect, and the length of time that the biologically active substance has to be released for treatment. Preferably, the biologically active substance is blended with the polymer matrix of the invention at different loading levels, preferably at room temperature and without the need for an organic solvent.

There is no critical upper limit on the amount of antineoplastic agent incorporated except for that of an acceptable solution or dispersion viscosity to maintain the physical characteristics desired for the composition. The lower limit of the antineoplastic agent incorporated into the delivery system is dependent upon the activity of the drug and the length of time needed for treatment. Thus, the amount of the antineoplastic agent should not be so small that it fails to produce the desired physiological effect, nor so large that the antineoplastic agent is released in an uncontrollable manner.

Typically, within these limits, amounts of the antineoplastic agent from about 1% up to about 65% can be incorporated into the present delivery systems. However, lesser amounts may be used to achieve efficacious levels of treatment for antineoplastic agent that are particularly potent.

In addition, the polymer composition of the invention can also comprise blends of the polymer of the invention with other biocompatible polymers or copolymers, so long as the additional polymers or copolymers do not interfere undesirably with the biodegradable or mechanical characteristics of the composition. Blends of the polymer of the invention with such other polymers may offer even greater flexibility in designing the precise release profile desired for targeted drug delivery or the precise rate of biodegradability desired. Examples of such additional biocompatible polymers include other poly(phosphoesters), poly(carbonates), poly(esters), poly(orthoesters), poly(amides), poly(urethanes), poly(imino-carbonates), and poly(anhydrides).

Pharmaceutically acceptable polymeric carriers may also comprise a wide range of additional materials. Without being limited thereto, such materials may include diluents, binders and adhesives, lubricants, disintegrants, colorants, bulking agents, flavorings, sweeteners, and miscellaneous materials such as buffers and adsorbents, in order to prepare a particular medicated composition, with the condition that none of these additional materials will interfere with the biocompatibility, biodegradability and physical state desired of the polymer compositions of the invention.

For delivery of an antineoplastic agent or some other biologically active substance, the agent or substance is added to the polymer composition. The agent or substance is either dissolved to form a homogeneous solution of reasonably constant concentration in the polymer composition, or dispersed to form a suspension or dispersion within the polymer composition at a desired level of "loading" (grams of biologically active substance per grams of total composition including the biologically active substance, usually expressed as a percentage).

While it is possible that the biodegradable polymer or the biologically active agent may be dissolved in a small quantity of a solvent that is non-toxic to more efficiently produce an amorphous, monolithic distribution or a fine dispersion of the biologically active agent in the flexible or flowable composition, it is an advantage of the invention that, in a preferred embodiment, no solvent is needed to form a flowable composition. Moreover, the use of solvents is preferably avoided because, once a polymer composition containing solvent is placed totally or partially within the body, the solvent dissipates or diffuses away from the polymer and must be processed and eliminated by the body, placing an extra burden on the body's clearance ability at a time when the illness (and/or other treatments for the illness) may have already deleteriously affected it.

However, when a solvent is used to facilitate mixing or to maintain the flowability of the polymer composition of the invention, it should be non-toxic, otherwise biocompatible, and should be used in minimal amounts. Solvents that are toxic clearly should not be used in any material to be placed even partially within a living body. Such a solvent also must not cause tissue irritation or necrosis at the site of administration.

Examples of suitable biocompatible solvents, when used, include N-methyl-2-pyrrolidone, 2-pyrrolidone, ethanol, propylene glycol, acetone, methyl acetate, ethyl acetate, methyl ethyl ketone, dimethylformamide, dimethyl sulfoxide, tetrahydrofuran, caprolactam, dimethylsulfoxide, oleic acid, or 1-dodecylazacycloheptan-2-one. Preferred solvents include N-methyl-2-pyrrolidone, 2-pyrrolidone, dimethyl sulfoxide, and acetone because of their solvating ability and their biocompatibility.

The polymer composition of the invention may be a flexible or flowable material. By "flowable" is meant the ability to assume, over time, the shape of the space containing it at body temperature. This includes, for example, liquid compositions that are capable of being sprayed into a site; injected with a manually operated syringe fitted with, for example, a 23-gauge needle; or delivered through a catheter.

Also included by the term "flowable", however, are highly viscous, "gel-like" materials at room temperature that may be delivered to the desired site by pouring, squeezing from a tube, or being injected with any one of the commercially available power injection devices that provide injection pressures greater than would be exerted by manual means alone for highly viscous, but still flowable, materials. When the polymer used is itself flowable, the polymer composition of the invention, even when viscous, need not include a biocompatible solvent to be flowable, although trace or residual amounts of biocompatible solvents may still be present. The degree of viscosity of the polymer can be adjusted by the molecular weight of the polymer, as well as by mixing the cis- and trans-isomers of the cyclohexane dimethanol in the backbone of the polymer.

The polymer composition of the invention can be administered by a variety of routes. For example, if flowable, it can be injected to form, after injection, a temporary biomechanical barrier to coat or encapsulate internal organs or tissues. The polymer composition of the invention can also be used to produce coatings for solid implantable devices.

However, most importantly, the polymer composition of the invention provides controllable and effective release of the antineoplastic agent over time, even in the case of large bio-macromolecules.

Implants and Delivery Systems

In its simplest form, a biodegradable polymer delivery system consists of a solution or dispersion of an antineoplastic agent in a polymer matrix having an unstable (biodegradable) bond incorporated into the polymer backbone. In a particularly preferred embodiment, a solid article comprising the composition of the invention is inserted within the peritoneum by implantation, injection, laparoscopy or otherwise being placed within the peritoneum of the subject being treated, for example, during or after the surgical removal of visibly cancerous tissue.

The antineoplastic agent of the composition and the polymer may form a homogeneous matrix, or the biologically active substance may be encapsulated in some way within the polymer. For example, the biologically active substance may be first encapsulated in a microsphere and then combined with the polymer in such a way that at least a portion of the microsphere structure is maintained. Alternatively, the biologically active substance may be sufficiently immiscible in the polymer of the invention that it is dispersed as small droplets, rather than being dissolved, in the polymer.

As a structural medical device, the polymer compositions of the inventions provide a wide variety of physical forms having specific chemical, physical and mechanical properties suitable for insertion into the peritoneum, in addition to being a composition that degrades in vivo into non-toxic residues.

Biodegradable drug delivery articles can be prepared in several ways. The polymer can be melt processed using conventional extrusion or injection molding techniques, or these products can be prepared by dissolving in an appropriate solvent, followed by formation of the device, and subsequent removal of the solvent by evaporation or extraction, e.g., by spray drying. By these methods, the polymers may be formed into articles of almost any size or shape desired, for example, implantable solid discs or wafers or injectable rods, microspheres, or other microparticles. Typical medical articles also include such as implants as laminates for degradable fabric or coatings to be placed on other implant devices.

The antineoplastic agent is typically released from the polymeric matrix at least as quickly as the matrix biodegrades in vivo. With some antineoplastic agents, the agent will be released only after the polymer has been degraded to a point where a non-diffusing substance has been exposed to bodily fluids. As the polymer begins to degrade, the biologically active substance that was completely surrounded by the polymer matrix begins to be liberated.

However, with this mechanism, a long peptide chain that is physically entangled in a rigid solid implant structure may tend to degrade along with the matrix and break off from the remainder of the peptide chain, thereby releasing incomplete fragments of molecules. When the polymer compositions of the invention are designed to be flexible, however, the polymer will typically degrade after the peptide or protein has been released in part. In a particularly preferred mechanism, when a peptide chain is being released from the composition of the invention, the composition remains flexible and allows a large-molecule protein to, at least partially, diffuse through the polymeric matrix prior to its own or the polymer's biodegradation.

The initial release rate of proteins from the compositions is therefore generally diffusion-controlled through channels in the matrix structure, the rate of which is inversely proportional to the molecular weight of the protein. Once polymer degradation begins, however, the protein remaining in the matrix may also be released by the forces of erosion.

The biodegradable amorphous matrices of the invention typically contain polymer chains that are associated with other chains. These associations can be created by a simple entanglement of polymer chains within the matrix, as opposed to hydrogen bonding or Van der Vaals interactions or between crystalline regions of the polymer or interactions that are ionic in nature. Alternatively, the synthesis of block copolymers or the blending of two different polymers can be used to create viscous, "putty-like" materials with a wide variation in physical and mechanical properties.

In a particularly preferred embodiment, the composition of the invention is sufficiently flowable to be injected into the body. It is particularly important that the injected composition result in minimal tissue irritation after injection or otherwise being inserted into the peritoneal cavity.

In one embodiment, the polymer composition of the invention is used to form a soft, drug-delivery "depot" that can be administered as a liquid, for example, by injection, but which remains sufficiently viscous to maintain the drug within the localized area around the injection site. The degradation time of the depot so formed can be varied from several days to a year or more, depending upon the polymer selected and its molecular weight. By using a polymer composition in flowable form, even the need to make an incision can be eliminated. In any event, the flexible or flowable delivery "depot" will adjust to the shape of the space it occupies within the body with a minimum of trauma to surrounding tissues.

When the polymer composition of the invention is flexible or flowable, it can be placed anywhere within the body, including a cavity such as the peritoneum, sprayed onto or poured into open wounds, or used as a site delivery system during surgery. When flowable, the composition of the invention can also be used to act as a temporary barrier in preventing the direct adhesion of different types of tissue to each other, for example, after abdominal surgery, due to its ability to encapsulate tissues, organs and prosthetic devices.

Once inserted, the polymer composition of the invention should remain in at least partial contact with a biological fluid, such as blood, internal organ secretions, mucous membranes, and the like. The implanted or injected composition will release the antineoplastic agent contained within its matrix at a controlled rate until the substance is depleted, following the general rules for diffusion or dissolution from a rigid, flexible or flowable biodegradable polymeric matrix.

The following examples are illustrative of preferred embodiments of the invention and are not to be construed as limiting the invention thereto. All polymer molecular weights are average molecular weights. All percentages are based on the percent by weight of the final delivery system or formulation being prepared, unless otherwise indicated, and all totals equal 100% by weight.

EXAMPLES

Example 1

Synthesis of Copolymer P(BHET-EOP/TC, 80/20)

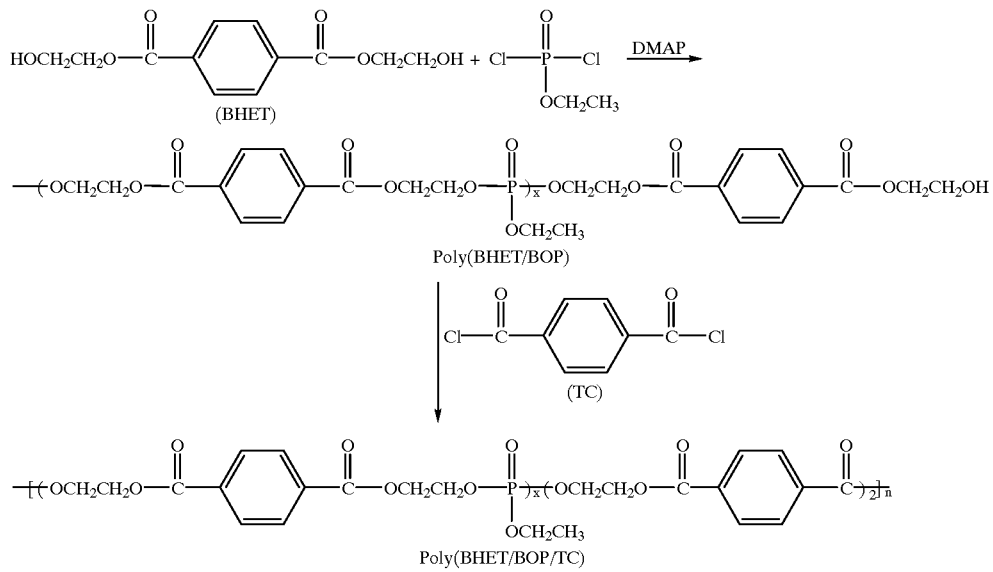

Under an argon stream, 10 g of 1,4-bis(hydroxyethyl) terephthalate (BHET), 9.61 g of 4-dimethylaminopyridine (DMAP), and 70 mL of methylene chloride were placed in a 250 mL flask equipped with a funnel. The solution in the flask was cooled down to −40° C. with stirring, and a solution of 5.13 g of ethyl phosphorodichloridate (EOP) (distilled before use) in 20 mL of methylene chloride was added dropwise through the funnel. After addition was complete, the mixture was stirred at room temperature for four hours to form the homopolymer BHET-EOP.

A solution of 1.60 g of terephthaloyl chloride (TC) (obtained from Aldrich Chemical Company and recrystallized with hexane before use) in 20 mL of methylene chloride was then added drop by drop. The temperature was brought up to about 45–50° C. gradually, and the reaction mixture was kept refluxing overnight to complete the copolymerization of the homopolymer P(BHET-EOP) with the additional monomer TC to form the copolymer P(BHET-EOP/TC).

The solvent was then evaporated, and the residue was redissolved in about 100–200 mL of chloroform. The chloroform solution was washed with a saturated NaCl solution three times, dried over anhydrous $Na_2SO_4$, and quenched into ether. The resulting precipitate was redissolved in chloroform and quenched again into ether. The resulting tough, off-white solid precipitate was filtered off and dried under vacuum. Yield 82%.

The structure of P(BHET-EOP/TC, 80/20) was ascertained by $^1$H-NMR, $^{31}$P-NMR and FT-IR spectra, as shown in FIGS. 1 and 2. The structure was also confirmed by elemental analysis, which correlated closely with theoretical ratios. The results of the elemental analysis are shown in FIG. 3.

Figure 4A:
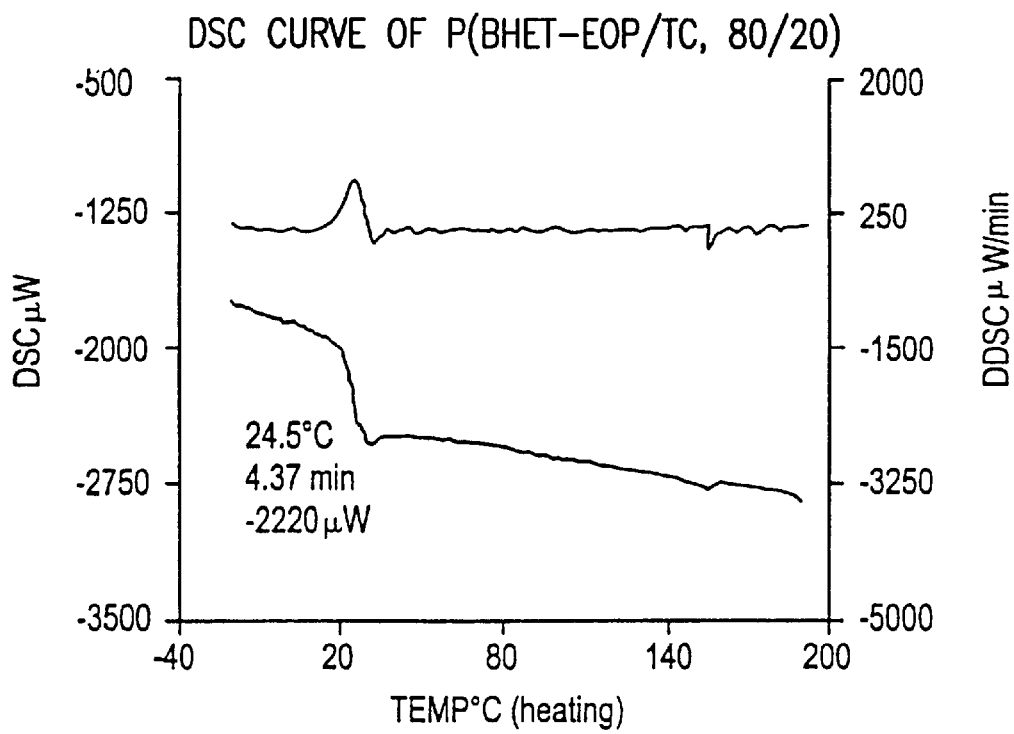
FIG. 4A shows the DSC curve of P(BHET-EOP/TC, 80/20)
Figure 4B:
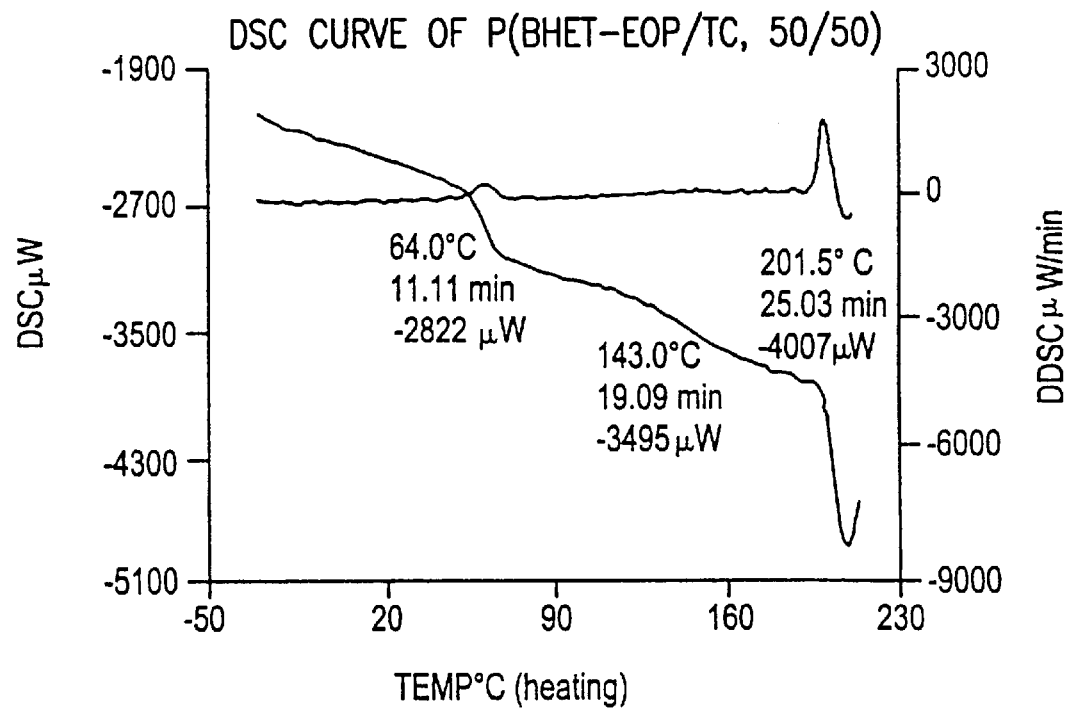
FIG. 4B shows the DSC curve of P(BHET-EOP /TC, 50/50).
Figure 5A:
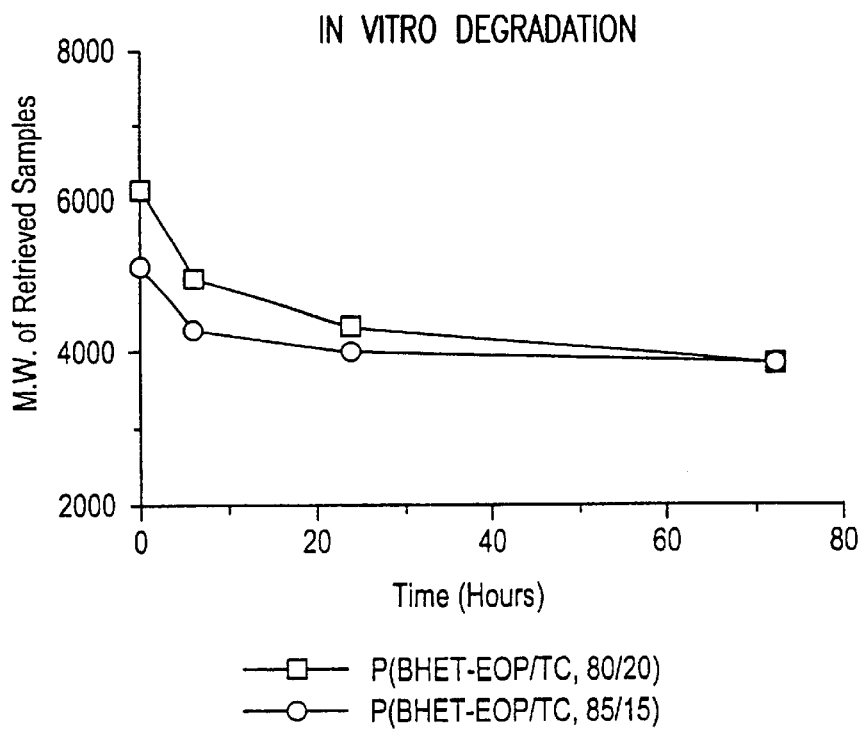
FIGS. 5A and 5B show the in vitro degradation data for P(BHET-EOP/TC, 80/20) and P(BHET-EOP/TC, 85/15).
Figure 5B:
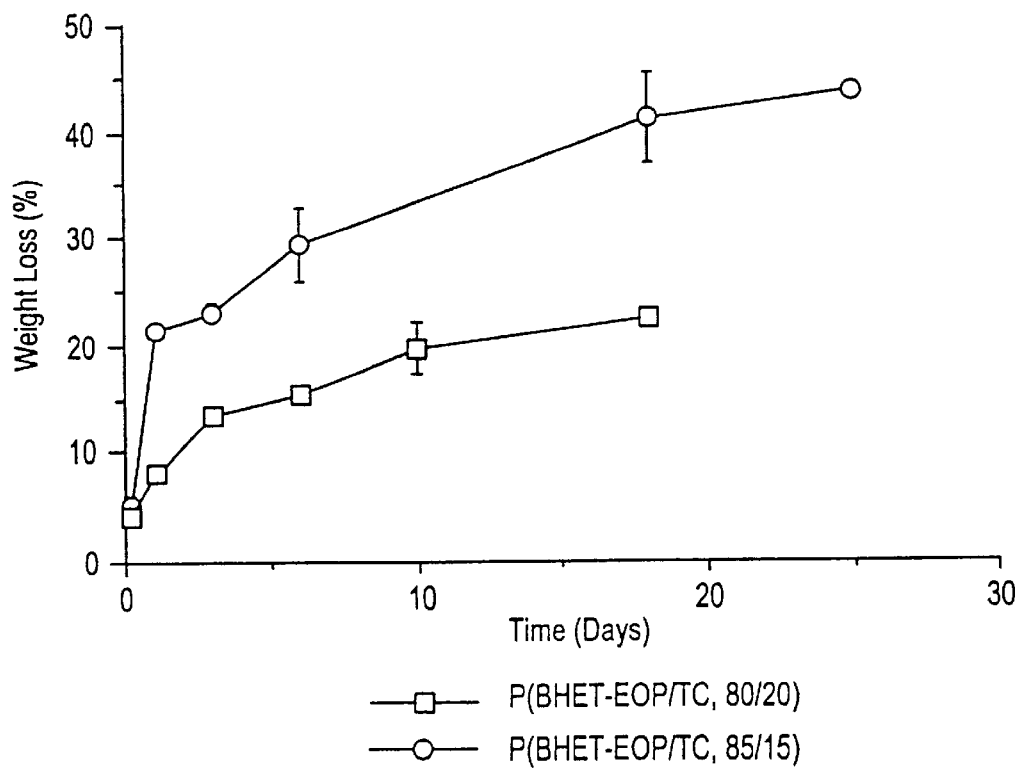

The molecular weight of P(BHET-EOP/TC, 80/20) was first measured by gel permeation chromatography (GPC) with polystyrene as the calibration standard. The resulting graph established a weight average molecular weight (Mw) of about 6100 and a number average molecular weight (Mn) of about 2200, as shown in FIG. 4. Vapor pressure osmometry ("VPO") for this copolymer gave an Mn value of about 7900. The results of these molecular weight studies are also shown in FIG. 3.

Example 2

Feed Ratio Variations of P(BHET-EOP/TC)

A series of other P(BHET-EOP/TC) copolymers of the invention were prepared by following the procedure described above in Example 1 except that the feed ratio of the EOP to TC used during the initial polymerization step and copolymerization step respectively was varied. The results are shown below in Table 1. From the feed ratio of EOP/TC, the value of "x" from the formula shown below can be calculated. For example, in P(BHET-EOP/TC, 80/20) prepared above in Example 1, x is 8.

TABLE 1

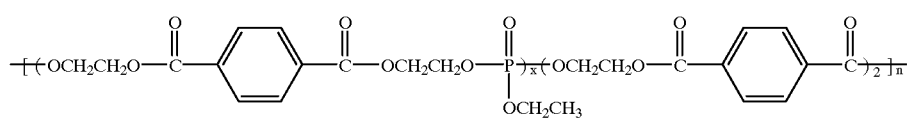

TABLE 1-continued

Variation of Feed Ratio of EOP to TC in P(BHET-EOP/TC)

| Feed Ratio of EOP/TC* | 100/0 | 95/5 | 90/10 | 85/15 | 80/20 | 50:50 |
|---|---|---|---|---|---|---|
| "x" | — | 38 | 18 | 11.4 | 8 | 2 |

*Feed ratio of ethyl phosphorodichloridate to terephthaloyl chloride.

Example 3

Synthesis and Isolation of the Homopolymer P (BHDPT-EOP)

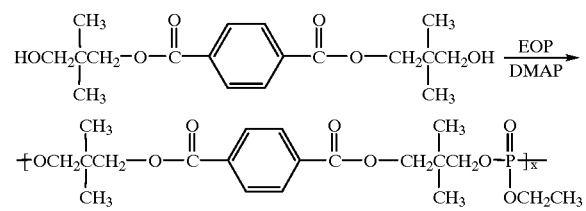

The BHDPT monomer prepared in Example 5 above and the acid acceptor 4-dimethylaminopyridine (DMAP) were dissolved in methylene chloride. The resulting solution was chilled to −70° C. using a dry ice/acetone bath, and an equal molar amount of ethyl phosphorodichloridate (EOP) was slowly added. The reaction mixture was then heated and refluxed overnight. The salt formed in the polymerization was removed by filtration. The remaining polymer solution (filtrate) was washed with a saturated NaCl solution three times, and the homopolymer was precipitated in diethyl ether.

Example 4

Synthesis of Copolymer P(BHDPT-EOP/TC)

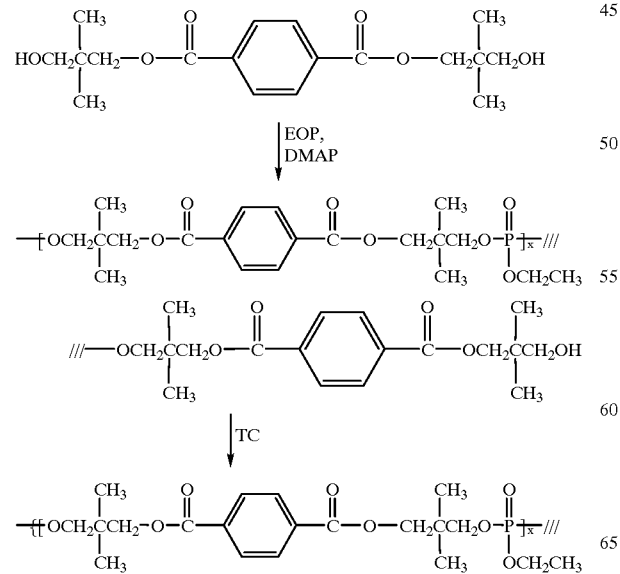

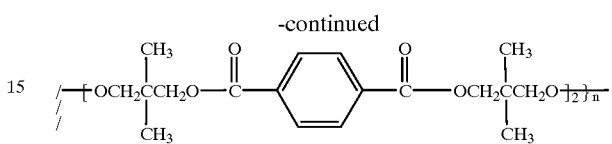

Copolymers of P(BHDPT-EOP) with TC were synthesized by the two-step solution copolymerization shown above. After the reaction between BHDPT and EOP had proceeded at room temperature for one hour, the reaction flask was cooled in a dry ice/acetone bath. An appropriate amount of TC (the number of moles of TC and EOP combined equaled the number of moles of BHDPT) was slowly added to the flask. The reaction mixture was then heated and refluxed overnight. The salt formed in the polymerization was removed by filtration. The remaining copolymer solution (filtrate) was washed with a saturated NaCl solution three times, and the copolymer was precipitated out in diethyl ether.

Example 5

Synthesis of Poly(phosphoester) P(BHDPT-HOP/TC)

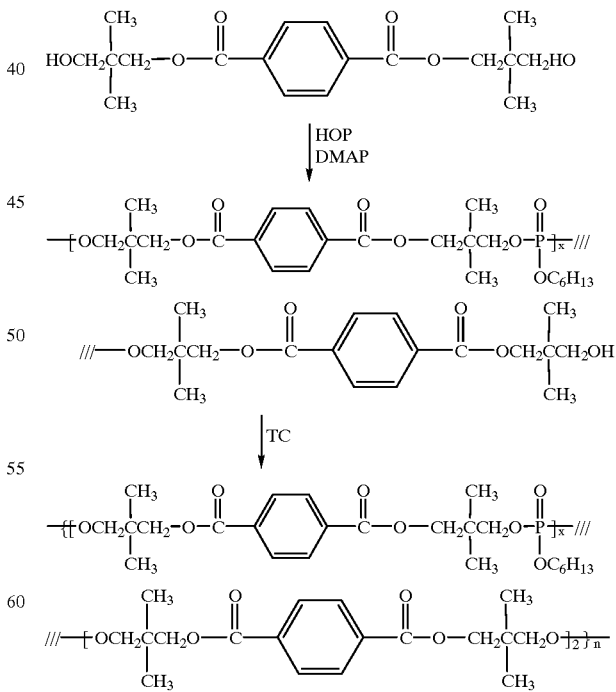

Copolymers of P(BHDPT-HOP) with TC were synthesized by a two-step solution polymerization. After the reaction between BHDPT and HOP had proceeded at room temperature for one hour, the reaction flask was cooled in a dry ice/acetone bath. An appropriate amount of TC (the number of moles of TC and HOP combined equaled the number of moles of BHDPT) was slowly added to the flask. The reaction mixture was then heated and refluxed overnight. The salt formed during the copolymerization was removed by filtration. The remaining copolymer solution (filtrate) was washed with a saturated NaCl solution three times, and the copolymer was precipitated out in diethyl ether.

Example 6

Other Diol Variations

Diol terephthalates that are structurally related to that of BHET and BHDPT were synthesized by reacting TC with either n-propylenediol or 2-methylpropylenediol, the structures of which are shown below, to form the corresponding diol terephthalate.

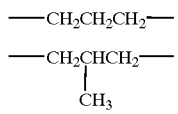

These diol terephthalates were then reacted with EOP to form the corresponding homopolymers. The homopolymers so formed were then used to produce the copolymers of the invention in a second reaction with TC, as described above in Example 4.

Example 7

Glass Transition Temperatures for P(BHET-EOP/TC) Copolymers

By differential scanning calorimetry (DSC), the glass transition temperatures (Tg's) of P(BHET-EOP/TC, 80/20) and P(BHET-EOP/TC, 50/50) were determined to be 24.5° C. and 62.2° C. respectively. FIG. 4 shows the DSC curves for these two polymers. The Tg's of four additional P(BHET-EOP/TC) copolymers of differing EOP/TC feed ratios were determined, and the results were tabulated, as shown below in Table 2:

TABLE 2

| | Glass Transition Temperatures (Tg's) of (BHET-EOP/TC) Polymers | | | | | |
|---|---|---|---|---|---|---|
| Ratio of EOP/TC* | 100/0 | 95/5 | 90/10 | 85/15 | 80/20 | 50:50 |
| Tg (° C.) | 19.1 | 20.7 | 21.2 | 29.8 | 24.5 | 62.2 |

*Feed ratio of ethyl phosphorodichloridate to terephthaloyl chloride

The Tg increased as the proportion of EOP decreased and the proportion of TC increased.

Example 8

Glass Transition Temperatures for P(BHDPT-EOP/TC) Copolymers

A study of the influence of an increasing proportion of terephthaloyl chloride (TC) on the Tg's of P(BHDPT-EOP/TC)polymers was also conducted. The results are shown below in Table 3.

TABLE 3

Influence of EOP/TC Ratio on the Tg of P (BHDPT-EOP/TC)

| Molar ratio (BHDPT/EOP/TC)* | Tg (° C.) |
|---|---|
| 100:100:0 | 14 |
| 100:100:0 | 19 |
| 100:90:10 | 16 |
| 100:85:15 | 24 |
| 100:80:20 | 23 |
| 100:75:25 | 33 |
| 100:75:25 | 49 |
| 100:50:50 | 43 |

*The total molar amount of TC and EOP equaled the molar amount of BHDPT.

Example 9

Glass Transition Temperatures for Various R Groups

A study was also conducted showing the effect on glass transition temperature (Tg) for copolymers made from the following series of diols having varying R groups:

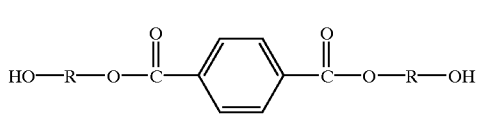

II where R is —CH₂CH₂—; —CH₂CH₂CH₂—; —CH₂CH(CH₃)CH₂—; and —CH₂CH(CH₃)₂CH₂—. The results are shown below in Table 4:

TABLE 4

Influence of the Changing "R" Group on Tg of Polymer

| "R" Group | Structure | Tg (° C.) |
|---|---|---|
| ethylene | —CH₂CH₂— | 14–19 |
| n-propylene | —CH₂CH₂CH₂— | −15 |
| 2-methyl-propylene | —CH₂CHCH₂—<br>\|<br>CH₃ | 11 |
| 2,2'-dimethyl-propylene | CH₃<br>\|<br>—CH₂CCH₂—<br>\|<br>CH₃ | 19 |

As shown in Table 4, the Tg increased as the size and the degree of branching of the R group increased. In addition, the polymers changed in physical state as the Tg changed. Specifically, as Tg increased, the polymers changed from rubbery to fine powders.

Example 10

Solubilities of the Polymers of the Invention

The solubility in organic solvents was determined for the homopolymer P(BHET-EOP, 100/0) and for the following block copolymers:

P(BHET-EOP/TC, 95/5),
P(BHET-EOP/TC, 90/10),

P(BHET-EOP/TC, 85/15 is),
P(BHET-EOP/TC, 80/20), and
P(BHET-EOP/TC, 50/50).

The organic solvents used for the test were chloroform, methylene chloride, N-methylpyrrolidone (NMP), dimethylformamide (DMF) and dimethylsulfoxide (DMSO). The results of these solubility tests are summarized below in Table 5.

TABLE 5

| Polymer | CHCl$_3$ | CH$_2$Cl$_2$ | NMP | DMF | DMSO |
|---|---|---|---|---|---|
| P (BHET-EOP, 100/0) | Easily soluble | Easily soluble | Good solubility | Good solubility | Good solubility |
| P (BHET-EOP/TC, 95/5) | Easily soluble | Easily soluble | Good solubility | Good solubility | Good solubility |
| P (BHET-EOP/TC, 90/10) | Easily soluble | Easily soluble | Good solubility | Good solubility | Good solubility |
| P (BHET-EOP/TC, 85/15) | Relatively soluble | Relatively soluble | Good solubility | Good solubility | Good solubility |
| P (BHET-EOP/TC, 80/20) | Relatively soluble | Relatively soluble | Good solubility | Good solubility | Good solubility |
| P (BHET-EOP/TC, 50/50) | Not soluble | Not soluble | Soluble with heating | Soluble with heating | Soluble with heating |

The results showed that the solubility of these polymers in organic solvents increased as the EOP/TC ratio increased.

Example 11

Viscosities of the Polymers

The intrinsic viscosities of a series of P(BHET-EOP/TC) polymers of varying feed ratios were measured in chloroform (CH$_3$Cl) at 40° C. in a Ubbelohde viscometer. The results are shown below in Table 6.

TABLE 6

Intrinsic Viscosities of P (BHET-EOP/TC) Polymers

| Ratio of EOP/TC* | 100/0 | 95/5 | 90/10 | 85/15 | 80/20 | 50:50 |
|---|---|---|---|---|---|---|
| [η] (dL/g) | .081 | .089 | .148 | .146 | 0.180 | N.D† |

*Feed ratio of ethyl phosphorodichloridate to terephthaloyl chloride.
†The intrinsic viscosity of P (BHET-EOP/TC, 50/50) was not determined because it was not soluble in chloroform.

Example 12

In vitro Degradation

Films of P(BHET-EOP/TC, 80/20) and P(BHET-EOP/TC, 85/15) were made by solution casting methods and were dried under vacuum for two days. Discs 1 mm in thickness and 6 mm in diameter were cut from these film sheets. Three discs of each copolymer were placed in 4 mL of phosphate buffer saline (PBS) (0.1M, pH 7.4) at 37° C. The discs were taken out of the PBS at different points in time, washed with distilled water, and dried overnight.

Figure 7A:
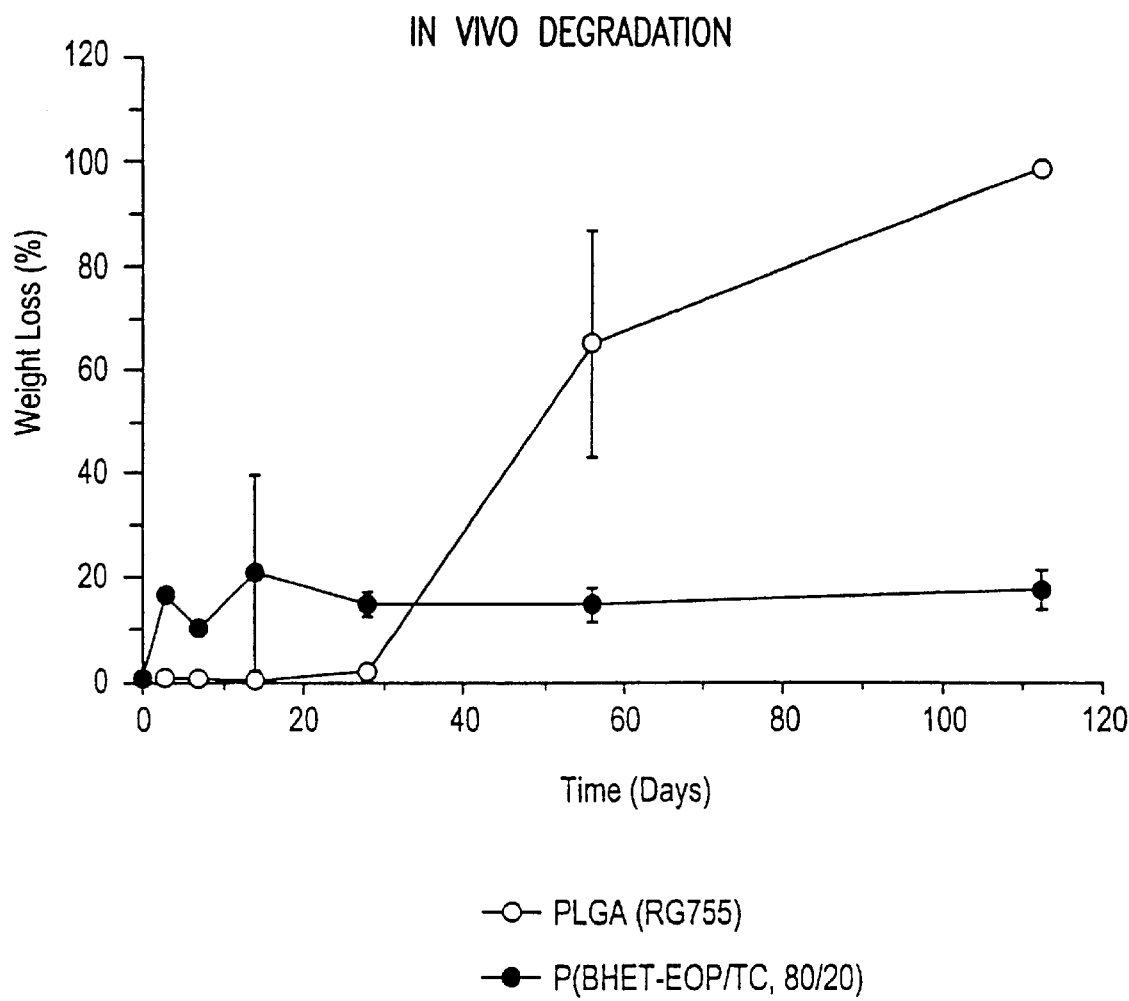
FIGS. 7A and 7B show the in vivo degradation of P(BHET-EOP/TC) in terms of weight or mass loss.
Figure 7B:
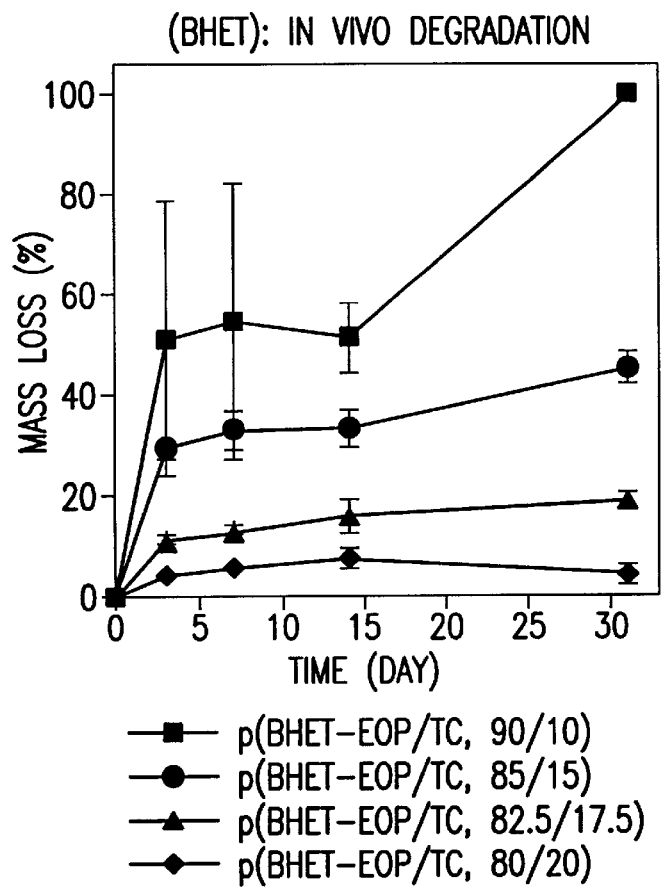

The samples were analyzed for change in molecular weight and weight loss over time, as shown in FIGS. 7A and 7B. The weight average molecular weight of P(BHET-EOP/TC, 80/20) decreased about 20% in three days. After 18 days, the P(BHET-EOP/TC, 85/15) and P(BHET-EOP/TC, 80/20) discs had lost about 40% and 20% in mass respectively.

This data demonstrated the feasibility of fine-tuning the degradation rate of the copolymers and confirmed that the copolymers became more hydrolytically labile as the phosphate component (EOP) was increased.

Figure 6:
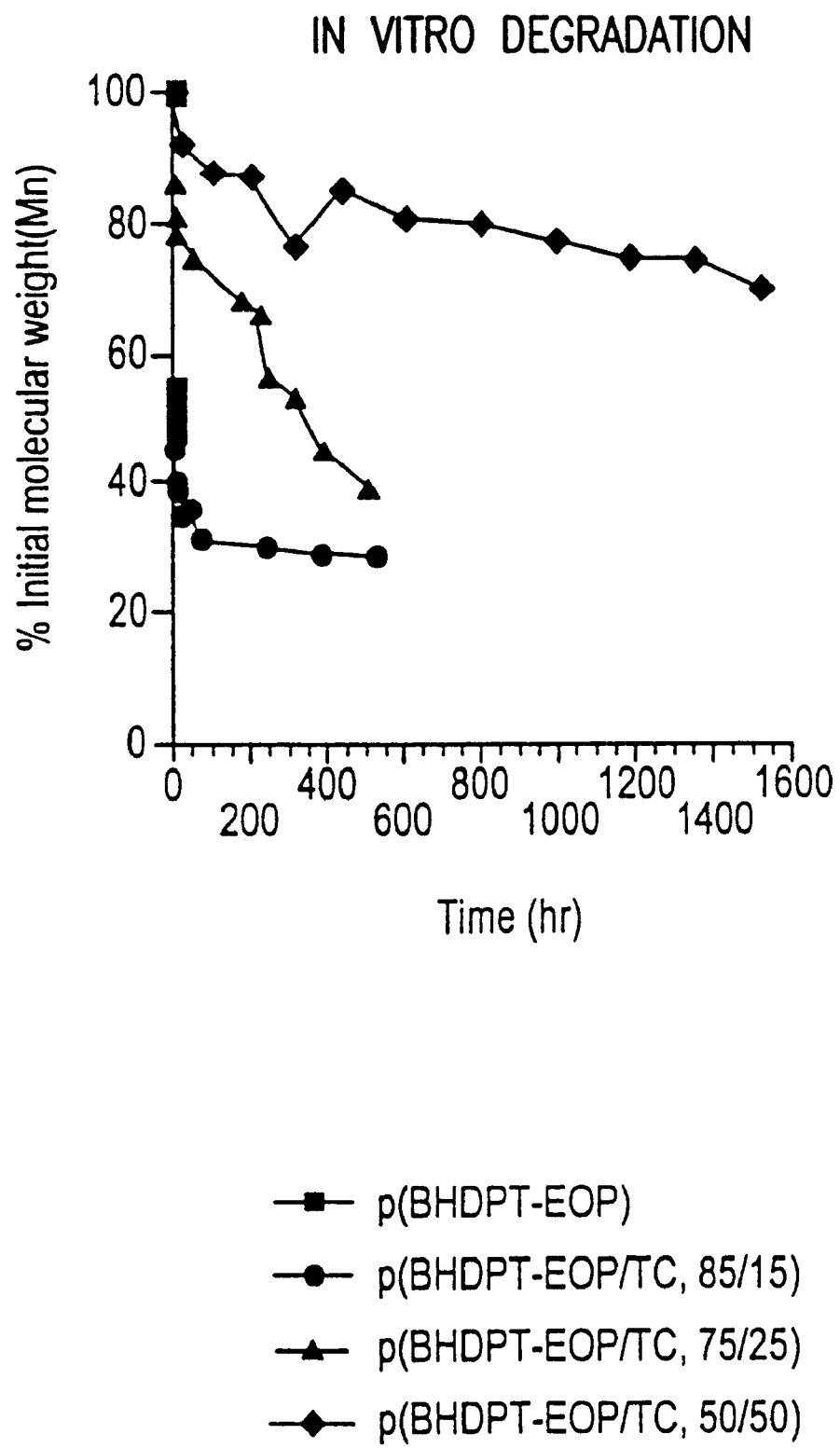
FIG. 6 shows the change in molecular weight of P(BHDPT-EOP) and P(BHDPT-EOP/TC) poly (phosphoesters) during in vitro degradation.

The same process was repeated for the P(BHDPT-EOP) copolymers having different feed ratios of EOP to TC. FIG. 6 is a graphic representation of the degree of degradation, as measured by change in molecular weight, over time for the homopolymer P(BHDPT-EOP) and the following block copolymers:

P(BHDPT-EOP/TC, 85/15),
P(BHDPT-EOP/TC, 75/25), and
P(BHDPT-EOP/TC, 50/50).

Example 13

In vivo Degradation of P(BHET-EOP/TC) Copolymer and Paclitaxel Release in vitro

Figure 7C:
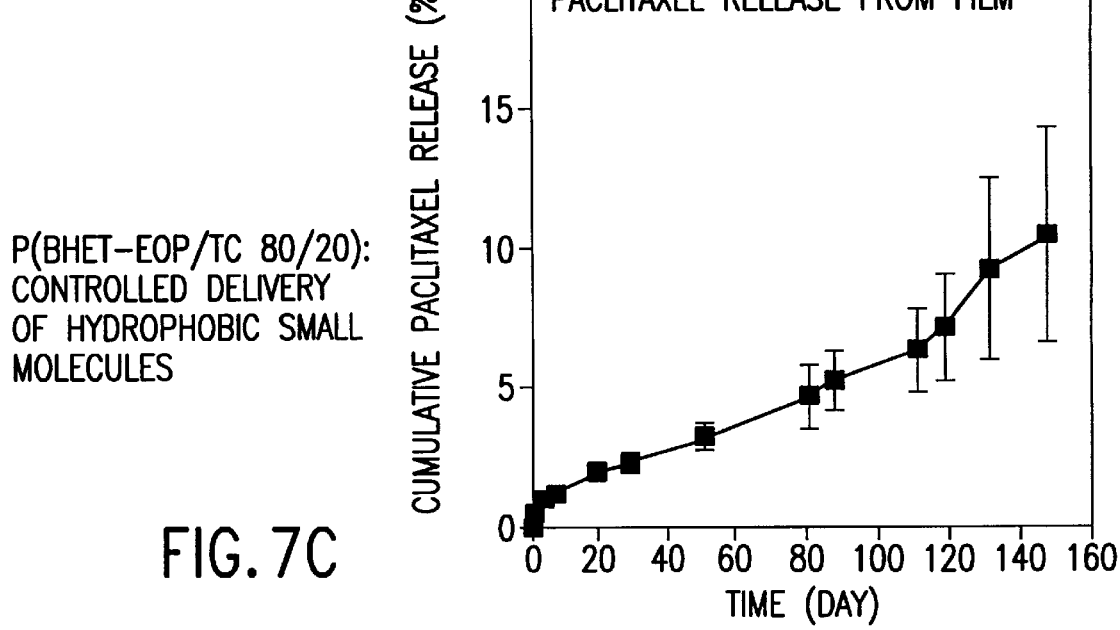
FIG. 7C shows the controlled delivery of hydrophobic small molecules, such as paclitaxel, from a p(BHET-EOP/TC, 80/20) film.

FIGS. 7A and 7B shows the in vivo degradation of P(BHET-EOP/TC, 80/20), as measured by weight loss. FIG. 7C shows paclitaxel release from film in vitro.

Example 14

In vitro Biocompatability/ Cytotoxicity of P(BHET-EOP/TC, 80/20)

The cytotoxicity of P(BHET-EOP/TC, 80/20) copolymer was assessed by culturing human embryonic kidney (HEK) cells on a cover slip that had been coated with the copolymer P(BHET-EOP/TC, 80/20). As a control, HEK cells were also cultured on a coverslip coated with TCPS. The cells cultured on the copolymer-coated cover slip exhibited normal morphology at all times and proliferated significantly in 72 days, as compared to a considerably lower amount when identical HEK cells were cultured on TCPS.

Example 15

In vivo Biocompatibility of P(BHET-EOP/TC, 80/20)

A 100 mg polymer wafer was formed from P(BHET-EOP/TC, 80/20) and, as a reference, a copolymer of lactic and glycolic acid (75/25, "PLGA") known to be biocompatible. These wafers were inserted between muscle layers of the right limb of adult SPF Sprague-Dawley rats under anesthesia. The wafers were retrieved at specific times, and the surrounding tissues were prepared for histopathological analysis by a certified pathologist using the following scoring:

| Score | Level of Irritation |
|---|---|
| 0 | No Irritation |
| 0–200 | Slight Irritation |
| 200–400 | Mild Irritation |
| 400–600 | Moderate Irritation |
| More than 600 | Severe Irritation |

The results of the histopathological analysis are shown below in Table 7.

TABLE 7

Inflammatory Response at Site of Implantation (i.m.)

| Polymer | 3 Days | 7 Days | 14 Days | 1 Mo. | 2 Mos. | 3 Mos. |
|---|---|---|---|---|---|---|
| P (BHET-EOP/TC, 80/20) | 151 | 116 | 163 | 98 | 60 | 35 |
| PLGA (75/25) | 148 | 98 | 137 | 105 | 94 | 43 |

The phosphoester copolymer P(BHET-EOP/TC, 80/20) was shown to have an acceptable biocompatability similar to that exhibited by the PLGA reference wafer.

Example 16

Preparation of P(BHET-EOP/TC, 80/20) Microspheres Encapsulating FITC-BSA

Microspheres were prepared via a double-emulsion/solvent-extraction method using FITC-labeled bovine serum albumin (FITC-BSA) as a model protein drug. One hundred $\mu$L of an FITC-BSA solution (10 mg/mL) were added to a solution of 100 mg of P(BHET-EOP/TC, 80/20) in 1 mL of methylene chloride, and emulsified via sonication for 15 seconds on ice. The resulting emulsion was immediately poured into 5 mL of a vortexing aqueous solution of 1% polyvinyl alcohol (PVA) and 5% NaCl. The vortexing was maintained for one minute. The resulting emulsion was poured into 20 mL of an aqueous solution of 0.3% PVA and 5% NaCl, which was being stirred vigorously. Twenty-five mL of a 2% isopropanol solution was added, and the mixture was kept stirring for one hour to ensure complete extraction. The resulting microspheres were collected via centrifugation at 3000×g, washed three times with water, and lyophilized. Empty microspheres were prepared in the same way except that water was used as the inner aqueous phase.

Figure 8:
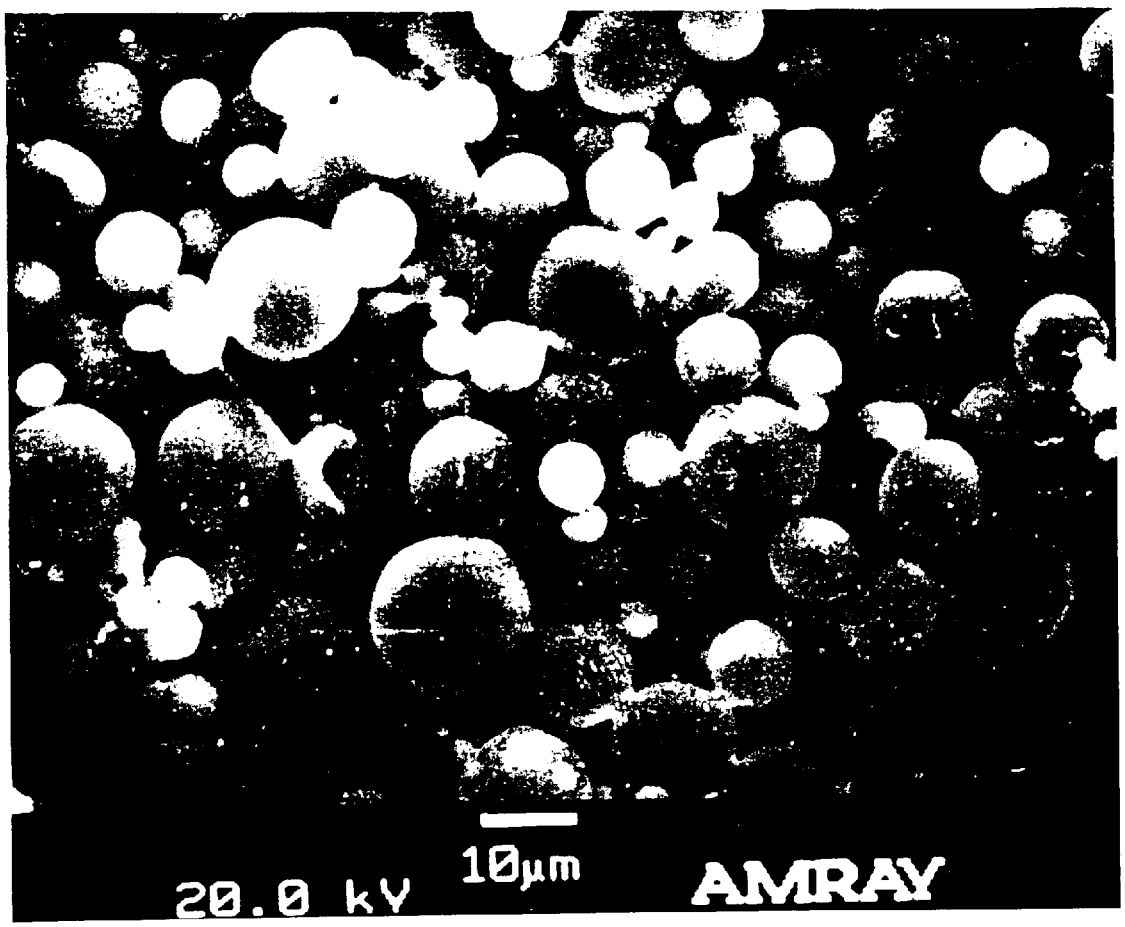
FIG. 8 shows an electron microscopic photograph of P(BHET-EOP/TC, 80/20) microspheres containing FITC-BSA.

These preparation conditions had been optimized for increased encapsulation efficiency, improved microsphere morphology, and minimal burst release. The resulting microspheres were mostly between 5 and 20 $\mu$m in diameter and exhibited a smooth surface morphology. FIG. 8 shows the size and smoothness of the microspheres, as demonstrated by electron microscopy.

The loading level of FITC-BSA was determined by assaying for FITC after hydrolyzing the microspheres in a 0.5 N NaOH solution overnight. Loading levels were determined by comparison with a standard curve, which had been generated by making a series of FITC-BSA solutions in 0.5 N NaOH. Protein loading levels of 1.5, 14.1 and 22.8 wt. % were readily obtained.

The encapsulation efficiency of FITC-BSA by the microspheres was determined at different loading levels by comparing the quantity of FITC-BSA entrapped with the initial amount in solution via fluorometry. As shown below in Table 8, encapsulation efficiencies of 84.6 and 99.6% were obtained. These results showed that encapsulation efficiencies of 70–90% would be readily obtainable.

TABLE 8

Encapsulation Efficiency and Loading Level of FITC-BSA in P (BHET-EOP/TC, 80/20)

| | High Loading (22.8%) | Low Loading (1.5%) |
|---|---|---|
| Loading (%) | | |
| Encapsulation Efficiency (%) | 99.6 | 84.6 |

In addition, it was determined by observation with confocal fluorescence microscopy that the encapsulated FITC-BSA was distributed uniformly within the microspheres.

Example 17

Preparation of P(BHDPT-EOP/TC, 50/50) Microspheres Containing Lidocaine

An aqueous solution of 0.5% w/v polyvinyl alcohol (PVA) was prepared in a 600 mL beaker by combining 1.35 g of PVA with 270 mL of deionized water. The solution was stirred for one hour and filtered. A copolymer/drug solution was prepared by combining 900 mg of P(BHDPT-EOP/TC, 50/50) copolymer and 100 mg of lidocaine in 9 mL of methylene chloride and vortex-mixing.

While the PVA solution was being stirred at 800 rpm with an overhead mixer, the polymer/drug mixture was added dropwise. The combination was stirred for one and a half hours. The microspheres thus formed were then filtered, washed with deionized water, and lyophilized overnight. The experiment yielded 625 mg of microspheres loaded with 3.7% w/w lidocaine.

Lidocaine-containing microspheres were also prepared from P(BHDPT-HOP/TC, 50/50) by the same process. This experiment yielded 676 mg of microspheres loaded with 5.3% w/w lidocaine.

Example 18

In vitro Release Kinetics of Microspheres Prepared from P(BHET-EOP/TC, 80/20) Copolymers Five mg of P(BHET-EOP/TC, 80/20) microspheres containing FITC-BSA were suspended in one mL of phosphate buffer saline (PBS) at pH 7.4 and placed into a shaker heated to a temperature of 37° C. At various points in time, the suspension was spun at 3000×g for 10 minutes, and 500 $\mu$l samples of the supernatant fluid were withdrawn and replaced with fresh PBS. The release of FITC-BSA from the microspheres was followed by measuring the fluorescence intensity of the withdrawn samples at 519 nm.

Scaling up, 50 mg of P(BHET-EOP/TC, 80/20) microspheres were suspended in vials containing 10 mL of phosphate buffer saline (PBS). The vials were heated in an incubator to a temperature of 37° C. and shaken at 220 rpm. Samples of the supernatant were withdrawn and replaced at various points in time, and the amount of FITC-BSA released into the samples was analyzed by spectrophotometry at 492 nm.

Figure 11:
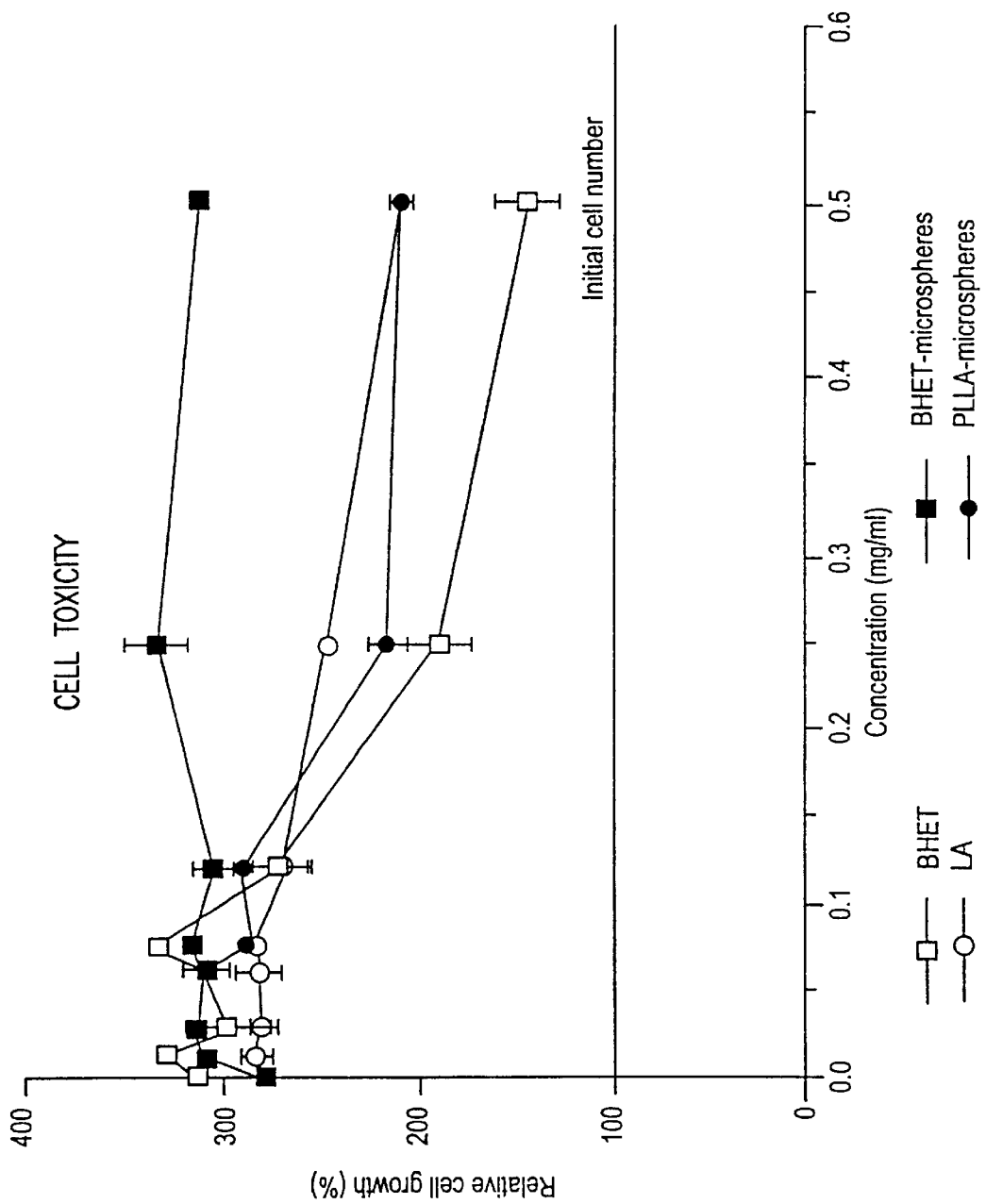
FIG. 11 shows the cytotoxicity of P(BHET-EOP/TC, 80/20) microspheres.
Figure 12:
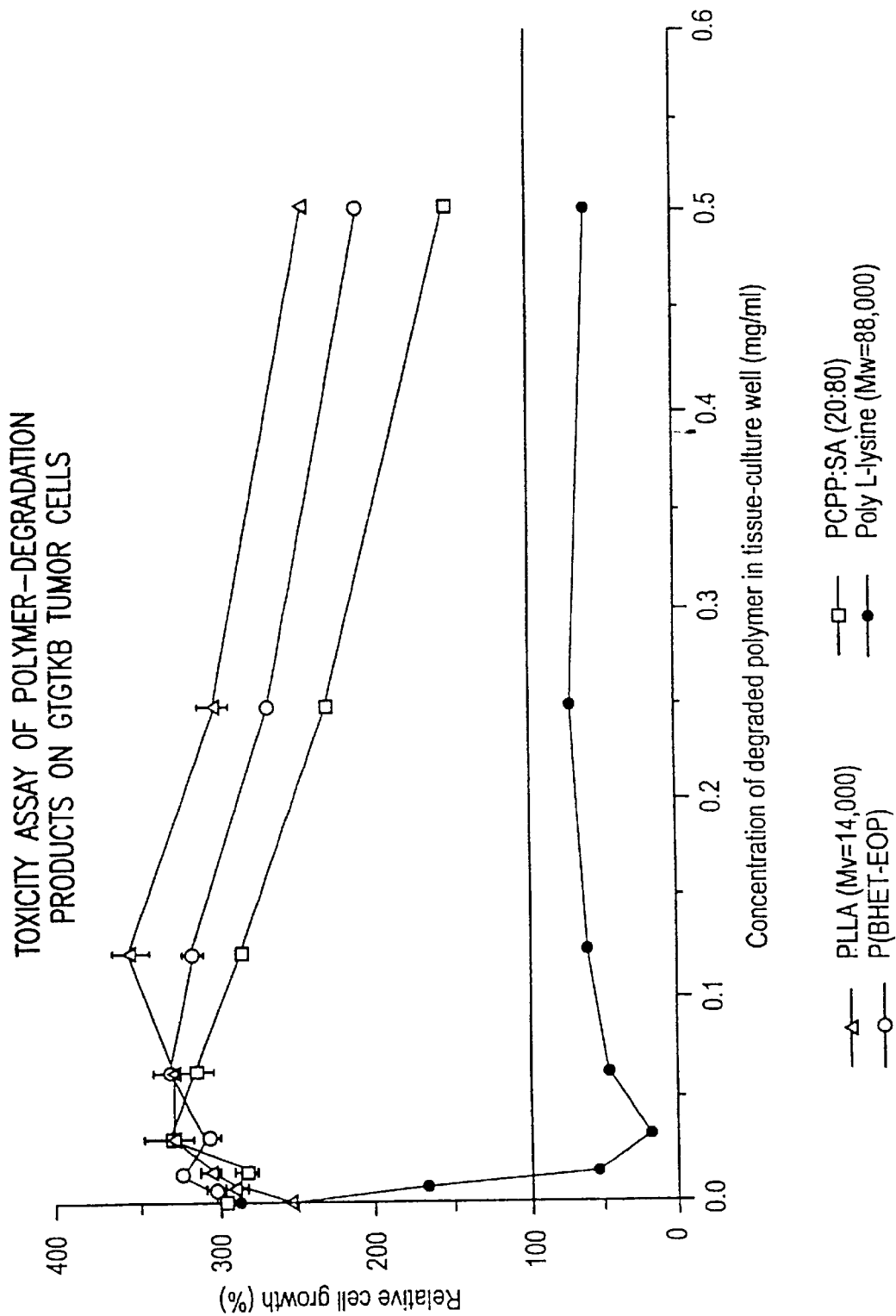
FIG. 12 shows a toxicity assay plot of relative cell growth (%) vs. concentration of degraded polymer in a tissue-culture well (mg/ml) for four separate polymers.

The results indicated that over 80% of the encapsulated FITC-BSA was released within the first two days, with an additional amount of about 5% being released after 10 days in PBS at 37° C. The release kinetics of FITC-BSA from P(BHET-EOP/TC, 80/20) microspheres at different loading levels are shown in FIG. 11.

Example 19

In vitro Release Kinetics of Microspheres Prepared from P(BHDPT-EOP/TC, 50/50) Copolymers

Figure 10:
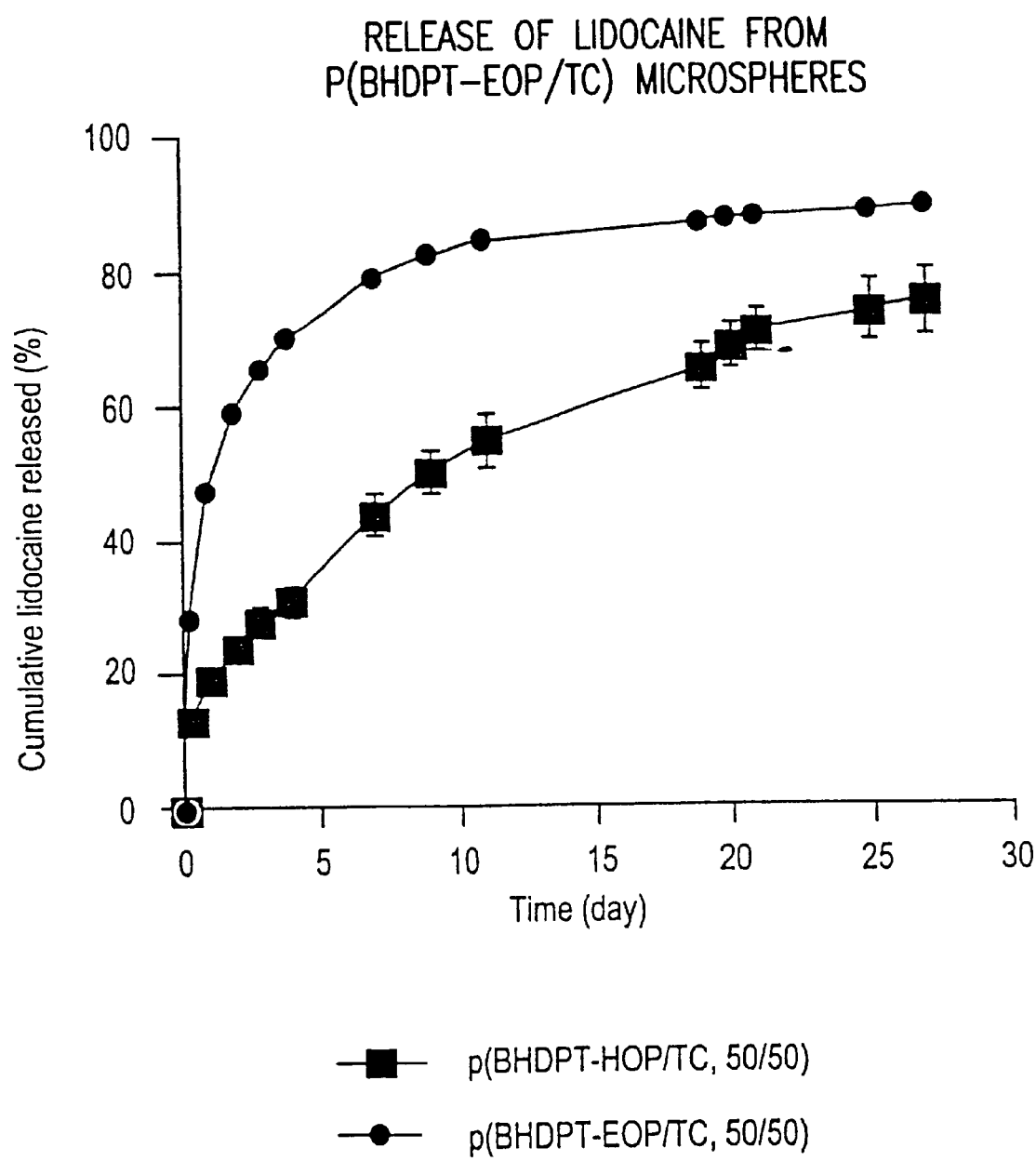
FIG. 10 shows the release of lidocaine from copolymer P(BHDPT-EOP/TC) microspheres.

Approximately 10 mg of P(BHDPT-EOP/TC, 50/50) microspheres loaded with lidocaine were placed in PBS (0.1 M, pH 7.4) at 37° C. on a shaker. Samples of the incubation solution were withdrawn periodically, and the amount of lidocaine released into the samples was assayed by HPLC. FIGS. 10 and 11 show the resulting release kinetics.

The same process was followed for microspheres prepared from P(BHDPT-HOP/TC, 50/50). FIGS. 10 and 11 also show the release kinetics of lidocaine from these microspheres.

Example 20

In vitro Cytotoxicity Assay of Copolymer on Cells

Figure 14:
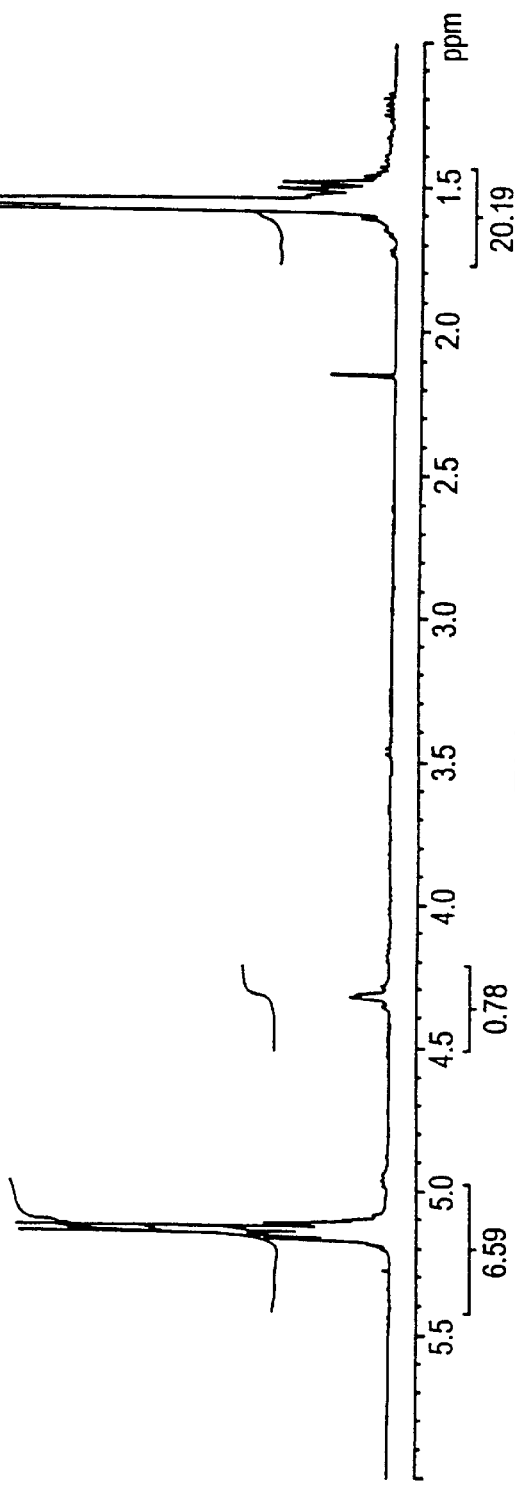
FIG. 14 shows the $^1$H-NMR spectrum of a polymer of the invention, P(LAEG-EOP).

P(BHET-EOP/TC, 80/20) microspheres were added to 96-well tissue culture plates at different concentrations. The wells were then seeded with human gastric carcinoma cells (GT3TKB) at a density of $10^4$ cells/well. The cells were incubated with the microspheres for 48 hours at 37° C. The resulting cell proliferation rate was analyzed by MTT assay and plotted as % relative growth vs. concentration of copolymer microspheres in the tissue culture well. The results are shown in FIG. 14.

Example 21

Toxicity Assay of Polymer-Degradation Products on GT3TKB Tumor Cells

About 100–150 mg of each of the following polymers were degraded separately in 20 mL of 1M NaOH at 37° C. for 1–2 days:

PLLA (Mw=14,000)

P(BHET-EOP)

PCPP:SA (20:80)

Poly(L-lysine) (Mw=88,000)

Complete degradation was observed for all of the polymers. The solution was then neutralized with 20 mL of 1M HCl.

Figure 13:
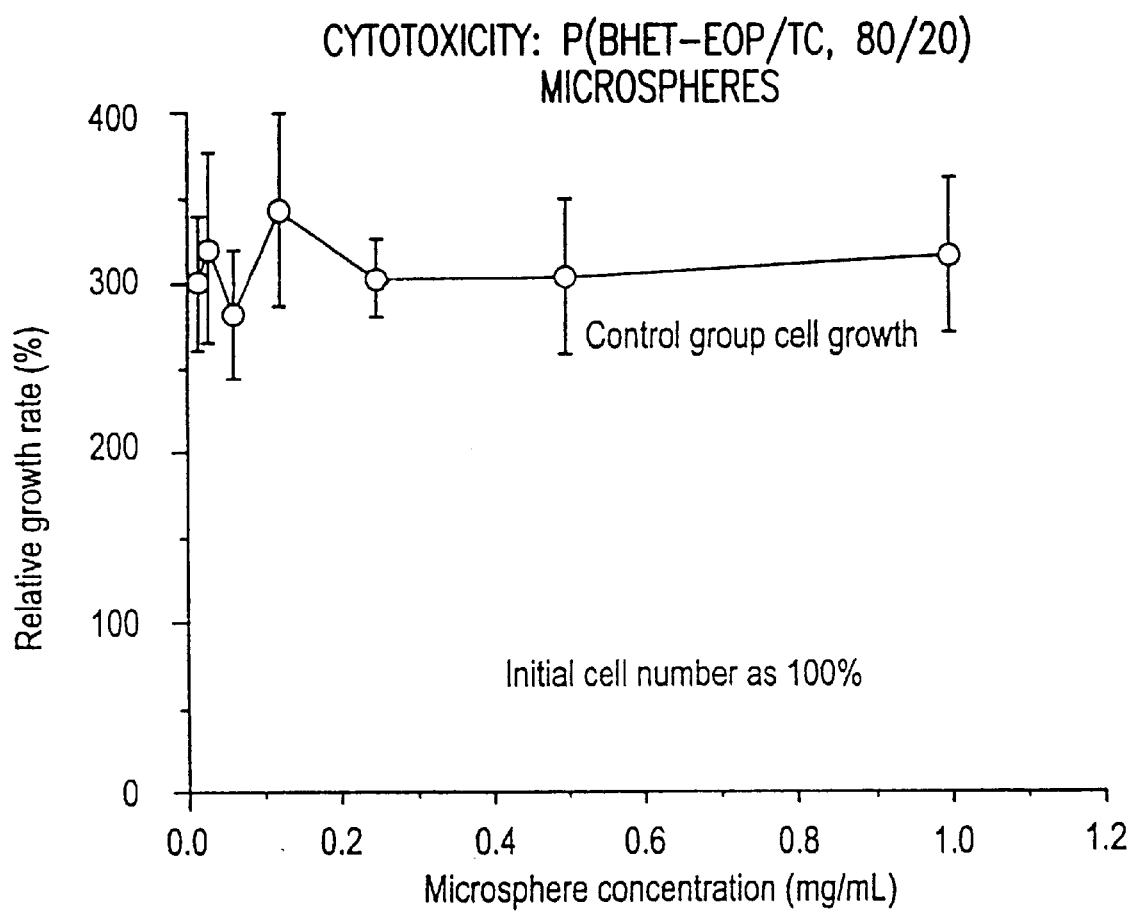
FIG. 13 shows the cytotoxicity of P(BHET-EOP/TC, 80/20) microspheres.

About 200 µL of various concentrations of the degraded polymer products were placed in 96-well tissue culture plates and seeded with human gastric carcinoma cells (GT3TKB) at a density of $10^4$/well. The degraded polymer products were incubated with the GT3TKB cells for 48 hours. The results of the assay were plotted as % relative growth vs. concentration of degraded polymer in the tissue-culture well and are shown in FIG. 13.

An additional toxicity assay was conducted with microspheres prepared from the monomer BHET and from the homopolymer BHET-EOP, and compared with microspheres prepared from LA and PLLA. The results of the assay were plotted as % relative growth vs. concentration of the polymers or microspheres in a tissue-culture cell and are shown in FIG. 14.

Example 22

Synthesis of Poly(L-lactide-co-ethyl-phosphate) [Poly(LAEG-EOP)]

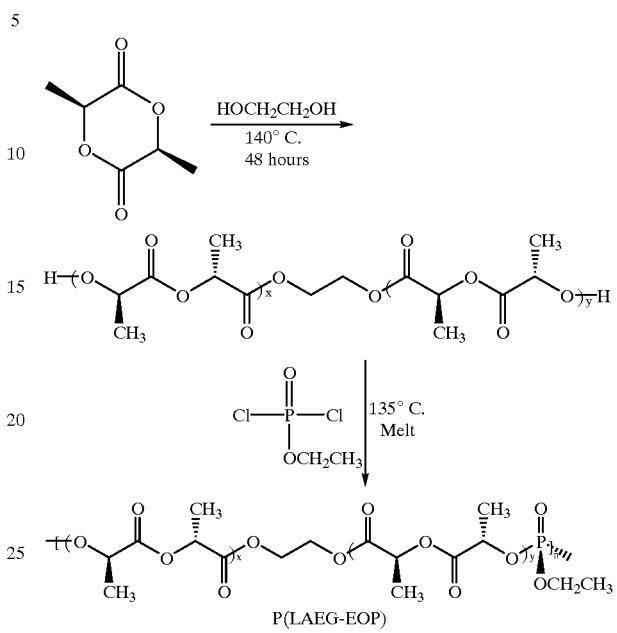

20 g (0.139 mole of (3S)-cis-3,6-dimethyl-1,4-dioxane-2,5-dione (L-lactide) (obtained from Aldrich Chemical Company, recrystallized with ethyl acetate, sublimed, and recrystallized with ethyl acetate again) and 0.432 g (6.94 mmole) of ethylene glycol (99.8%, anhydrous, from Aldrich) were placed in a 250 mL round-bottomed flask flushed with dried argon. The flask was closed under vacuum and placed in an oven heated to 140° C. The flask was kept at this temperature for about 48 hours with occasional shaking.

The flask was then filled with dried argon and placed in oil bath heated to 135° C. Under an argon stream, 1.13 g of ethyl phosphorodichloridate was added with stirring. After one hour of stirring, a low vacuum (about 20 mm Hg) was applied to the system, and it was allowed to stand overnight. One hour before work-up, a high vacuum was applied. After cooling, the polymer was dissolved in 200 mL of chloroform and quenched into one liter of ether twice to an off-white precipitate, which was dried under vacuum.

It was confirmed by NMR spectroscopy that the polymer obtained was the desired product, poly(L-lactide-co-ethyl-phosphate) [P(LAEG-EOP)], as shown in FIGS. 6 and 7.

Example 23

Properties of P(LAEG-EOP)

Figure 16A:
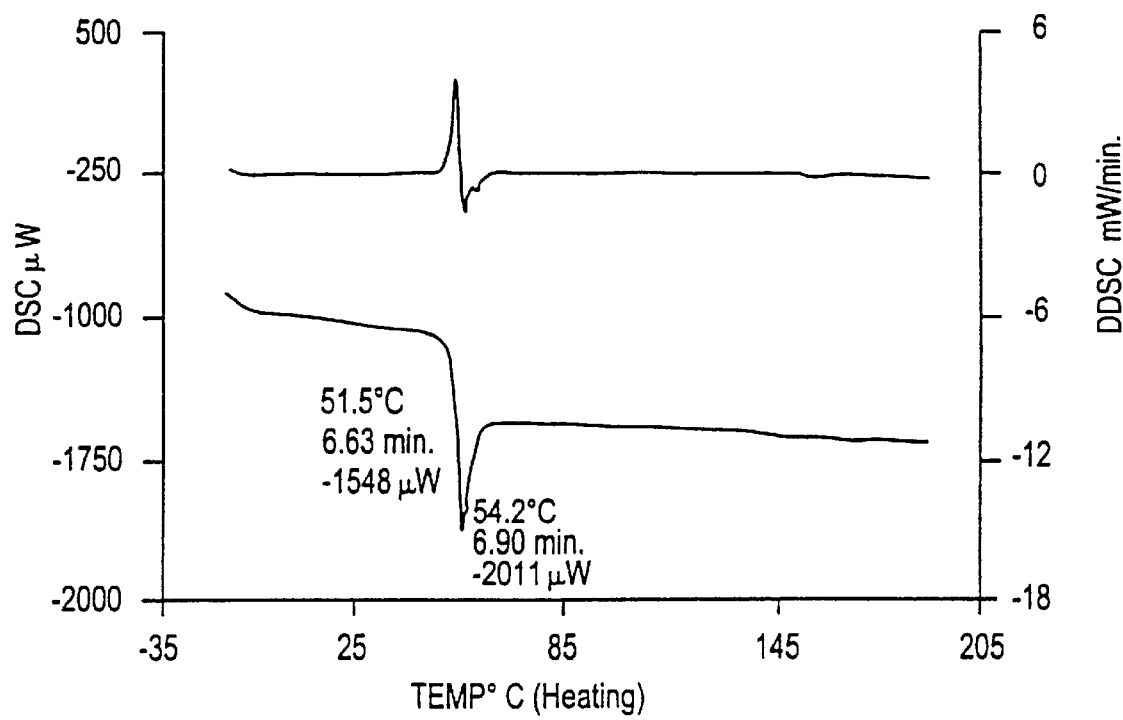
FIGS. 16A and 16B show differential scanning calorimetry data for two polymers of the invention.
Figure 16B:
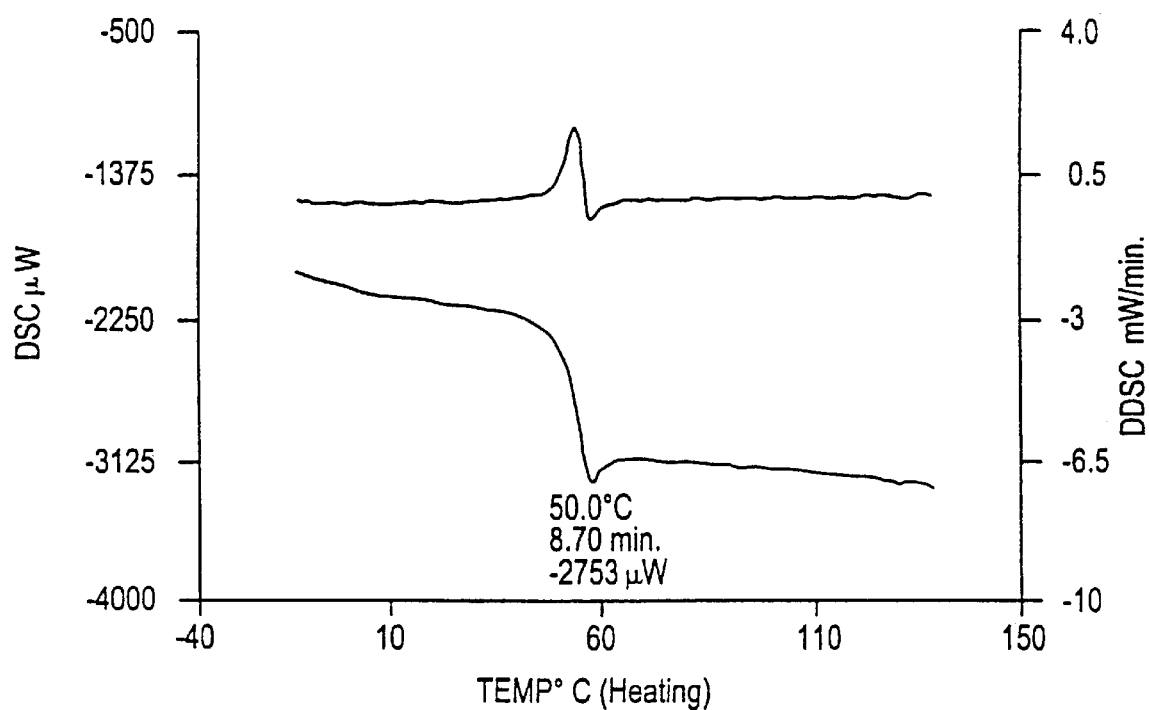

A P(LAEG-EOP) polymer where (x or y)/n 10:1 was prepared as described above in Example 22. The resulting poly(phosphoester-co-ester) polymer was analyzed by GPC using polystyrene as a standard, and the resulting graph established an Mw of 33,000 and an Mn of 4800, as shown in FIG. 16.

Figure 17:
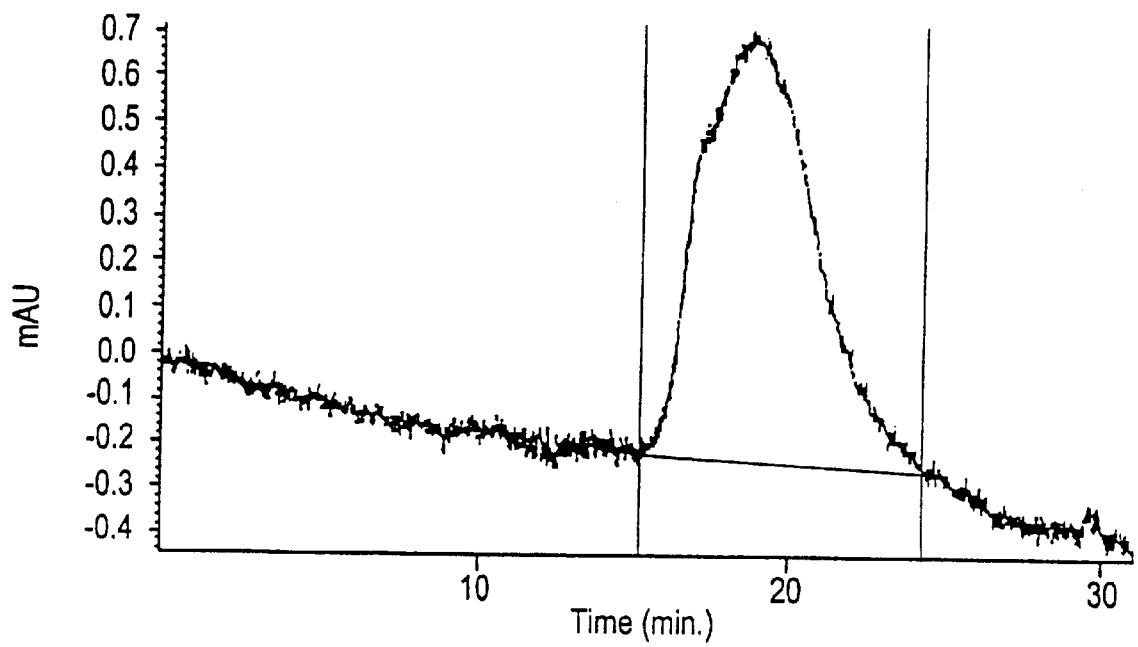
FIG. 17 shows the results of a GPC analysis of a polymer of the invention in graphic form.

The viscosity was measured in chloroform ($CH_3Cl$) at 40° C. and determined to be 0.315 dL/g. The polymer was soluble in ethyl acetate, acetone, acetonitrile, chloroform, dichloromethane, tetrahydrofuran, N-methylpyrrolidone, dimethylformamide, and dimethyl sulfoxide. The polymer formed a brittle film, and the Tg was determined by DSC to be 51.5° C., as shown in FIGS. 17A and 17B.

Example 24

Synthesis of Poly(L-lactide-co-hexyl-phosphate) [Poly(LAEG-HOP)]

A second poly(L-lactide-phosphate) having the following structure:

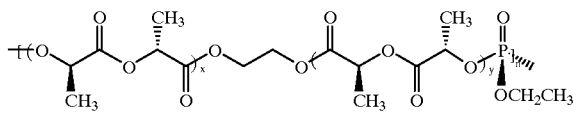

was also prepared by the method described in Example 22, except that hexyl phosphorodichloridate ("HOP") was substituted for EOP (ethyl phosphorodichloridate).

Example 25

Properties of P(LAEG-EOP) and P(LAEG-HOP)

Figure 18:
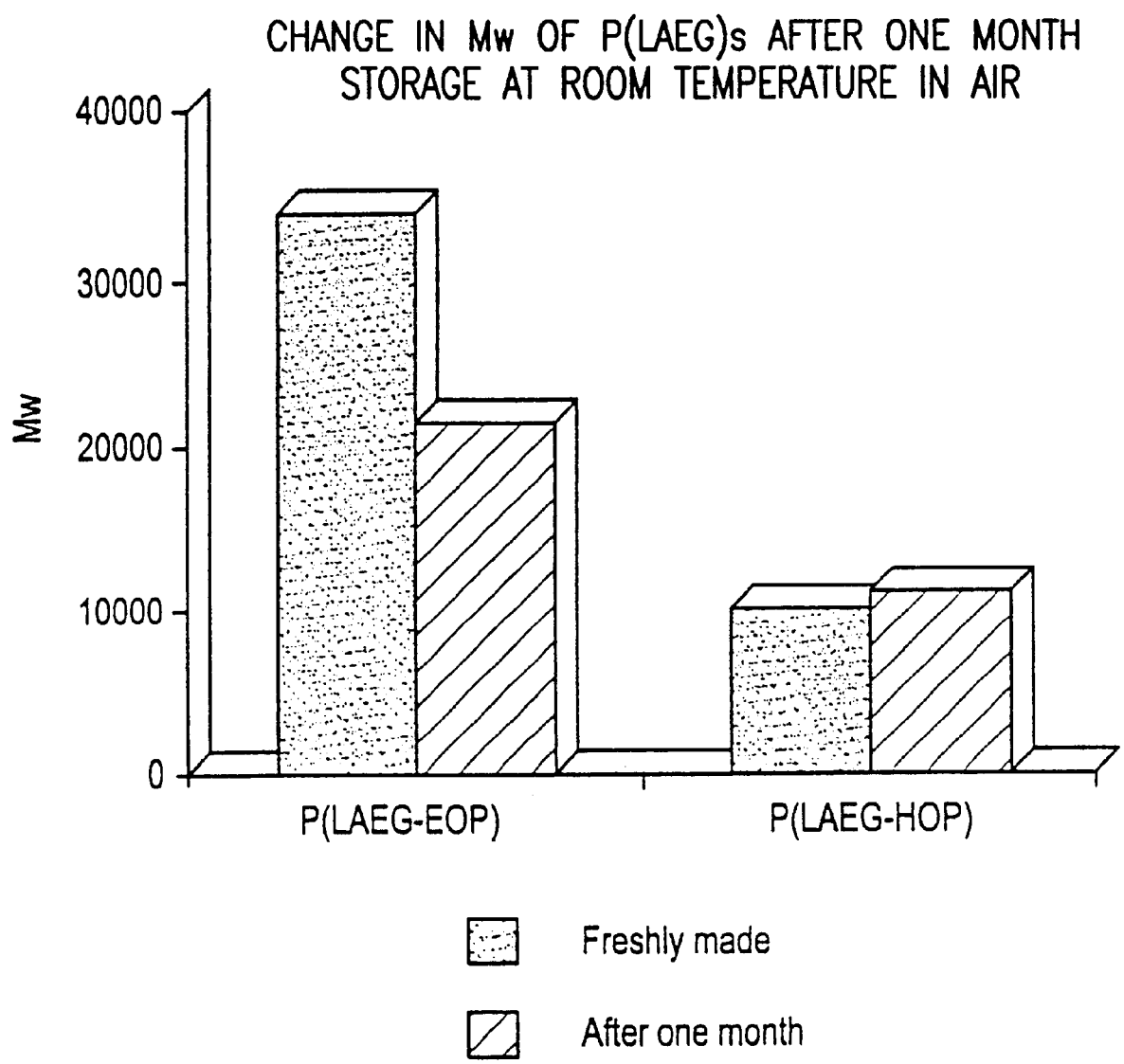
FIG. 18 shows the change in Mw of two polymers of the invention after being exposed to air at room temperature for one month.
Figure 19:
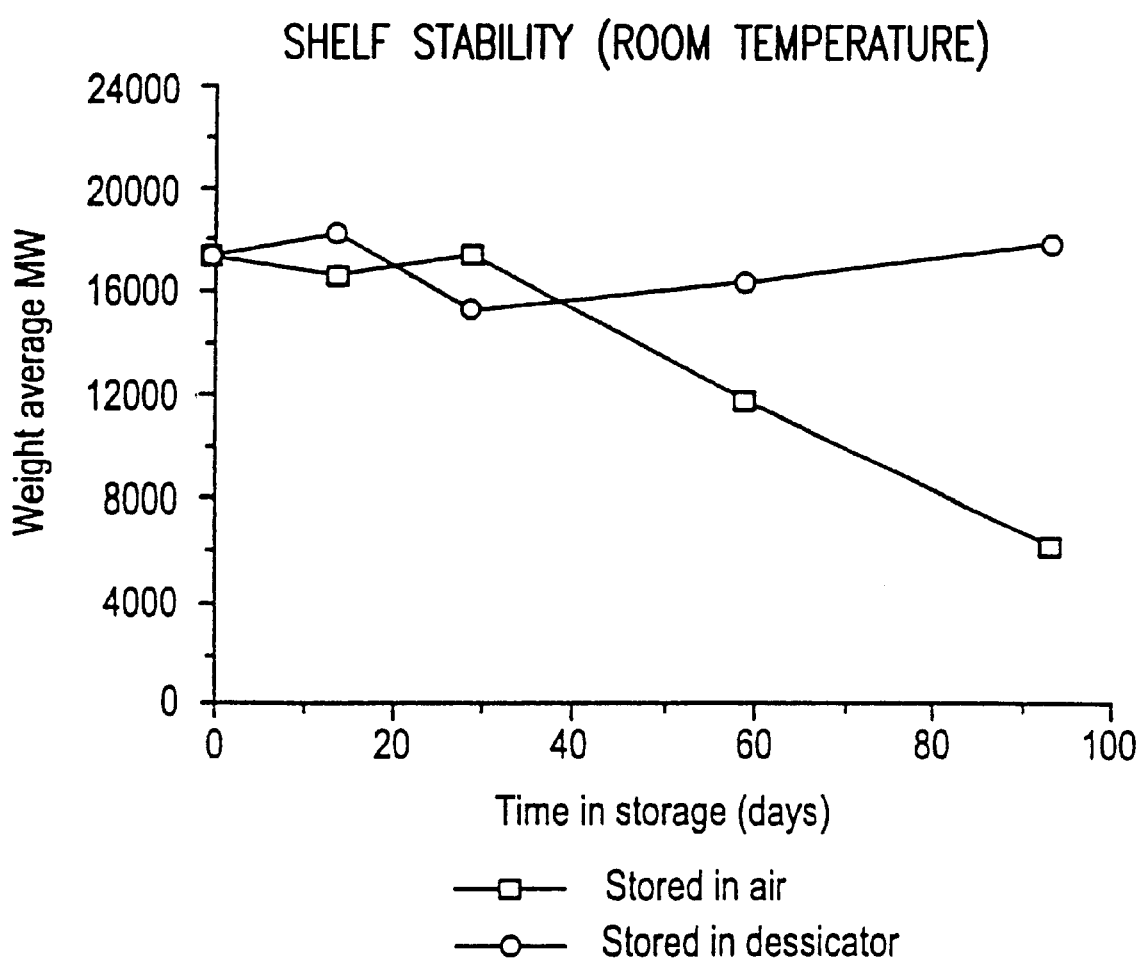
FIG. 19 shows shelf stability data for a polymer of the invention at room temperature.
Figure 20A:
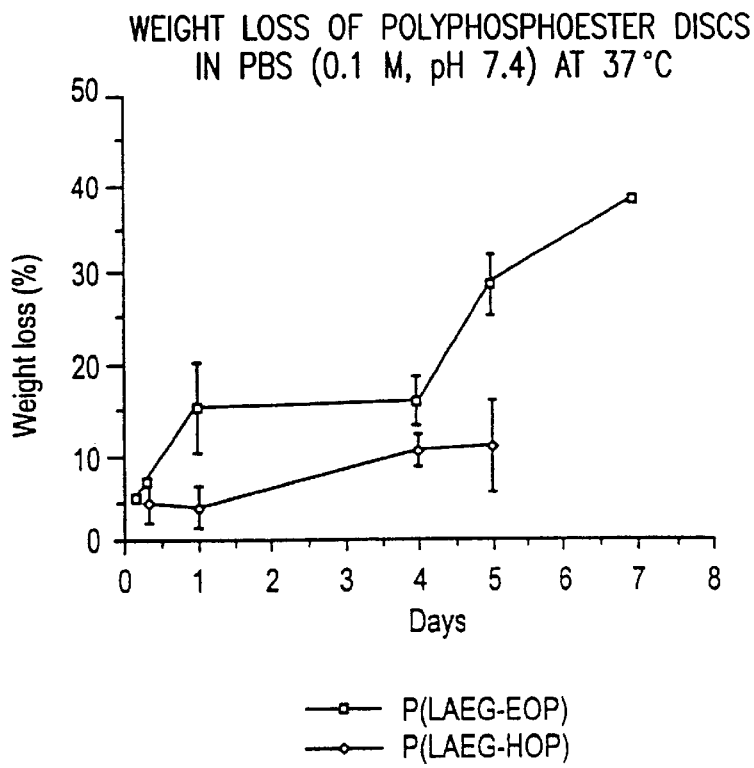
FIGS. 20A and 20B show the weight loss (21A) and the change in Mw (21B) for discs fabricated from two polymers of the invention over a period of eight days in PBS at 37° C.
Figure 20B:
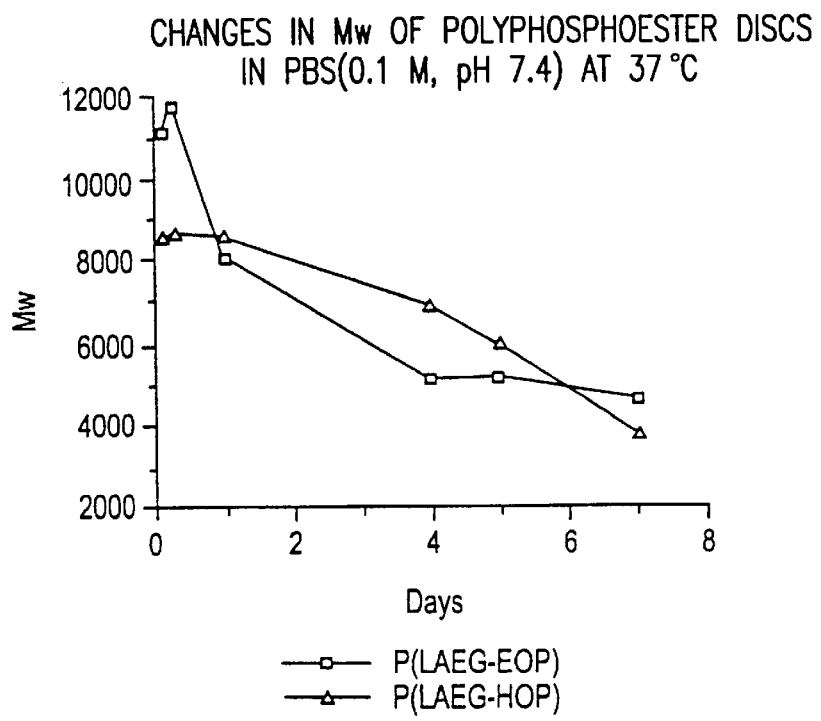
Figure 21A:
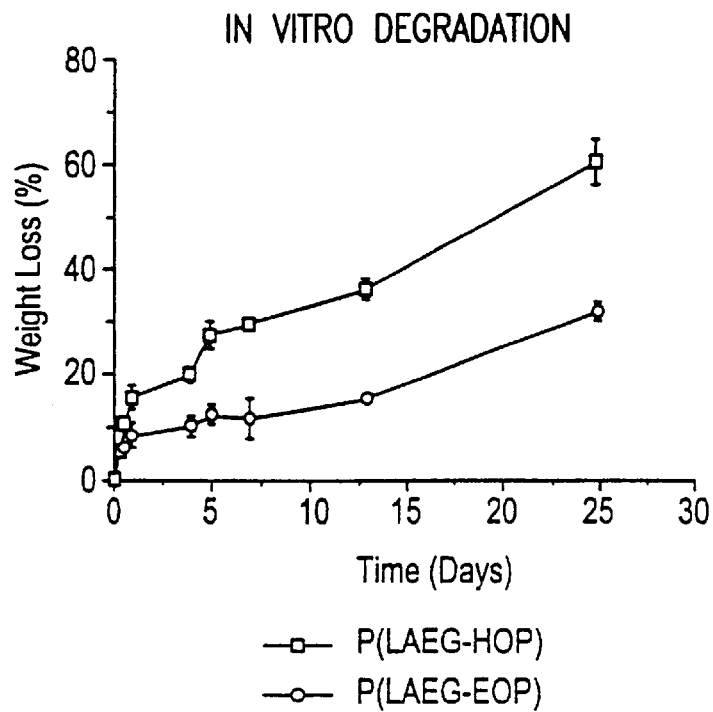
FIGS. 21A and 21B show the weight loss (22A) and the change in Mw (22B) for discs fabricated from two polymers of the invention, in vitro.
Figure 21B:
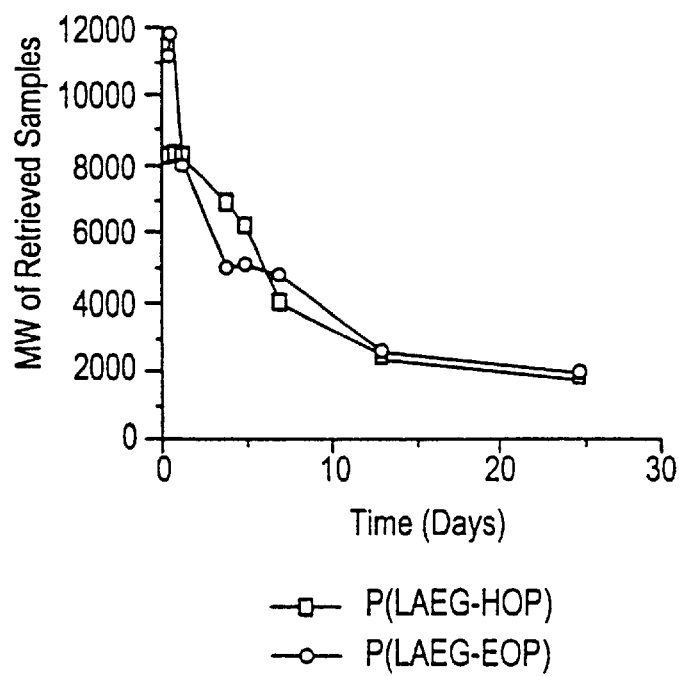

The weight-average molecular weight (Mw) of the phosphoester-co-ester polymer of Example 22, P(LAEG-EOP), and the polymer of Example 24, P(LAEG-HOP), were first determined by gel permeation chromatography (GPC) with polystyrene as the calibration standard, as shown in FIG. 18. Samples of each were then allowed to remain exposed to room temperature air to test for ambient, unprotected storage capability. After one month, the Mw was again determined for each polymer. The results (plotted in FIG. 19) showed that, while the Mw for p(LAEG-EOP) was reduced by about one-third after a month of unprotected ambient conditions, the Mw for p(LAEG-HOP) remained fairly constant, even showing a slight increase. See also FIG. 20.

Discs for degradation studies were then fabricated from each polymer by compression molding at 50° C. and a pressure of 200 MPa. The discs were 4 mm in diameter, 1.5 mm in thickness, and 40 mg in weight. The degradation studies were conducted by placing the discs in 4 mL of 0.1M PBS (pH 7.4) at 37° C. Duplicate samples were removed at different time points up to eight days, washed with distilled water, and dried under vacuum overnight. Samples were analyzed for weight loss and molecular weight change (GPC), and the results are shown in FIGS. 4A, 4B, 10A and 10B. Both polymers, P(LAEG-EOP) and P(LAEG-HOP), demonstrated favorable degradation profiles.

Example 26

In vivo Biocompatibility of P(LAEG-EOP)

A 100 mg polymer wafer was formed from P(LAEG-EOP) and, as a reference, a copolymer of lactic and glycolic acid ["PLGA (RG755)"] known to be biocompatible. These wafers were inserted between muscle layers of the right limb of adult SPF Sprague-Dawley rats under anesthesia. The wafers were retrieved at specific times, and the surrounding tissues were prepared for histopathological analysis by a certified pathologist using the following scoring:

| Score | Level of Irritation |
|---|---|
| 0 | No Irritation |
| 0–200 | Slight Irritation |
| 200–400 | Mild Irritation |
| 400–600 | Moderate Irritation |
| More than 600 | Severe Irritation |

The results of the histopathological analysis are shown below in Table 9.

TABLE 9

| | Inflammatory Response at Site of Implantation (i.m.) | | | | | |
|---|---|---|---|---|---|---|
| Polymer | 3 Days | 7 Days | 14 Days | 1 Mo. | 2 Mos. | 3 Mos. |
| P (LAEG-EOP) | 130 | 123 | 180 | 198 | 106 | 99 |
| PLGA (RG755) | 148 | 98 | 137 | 105 | 94 | 43 |

Figure 23:
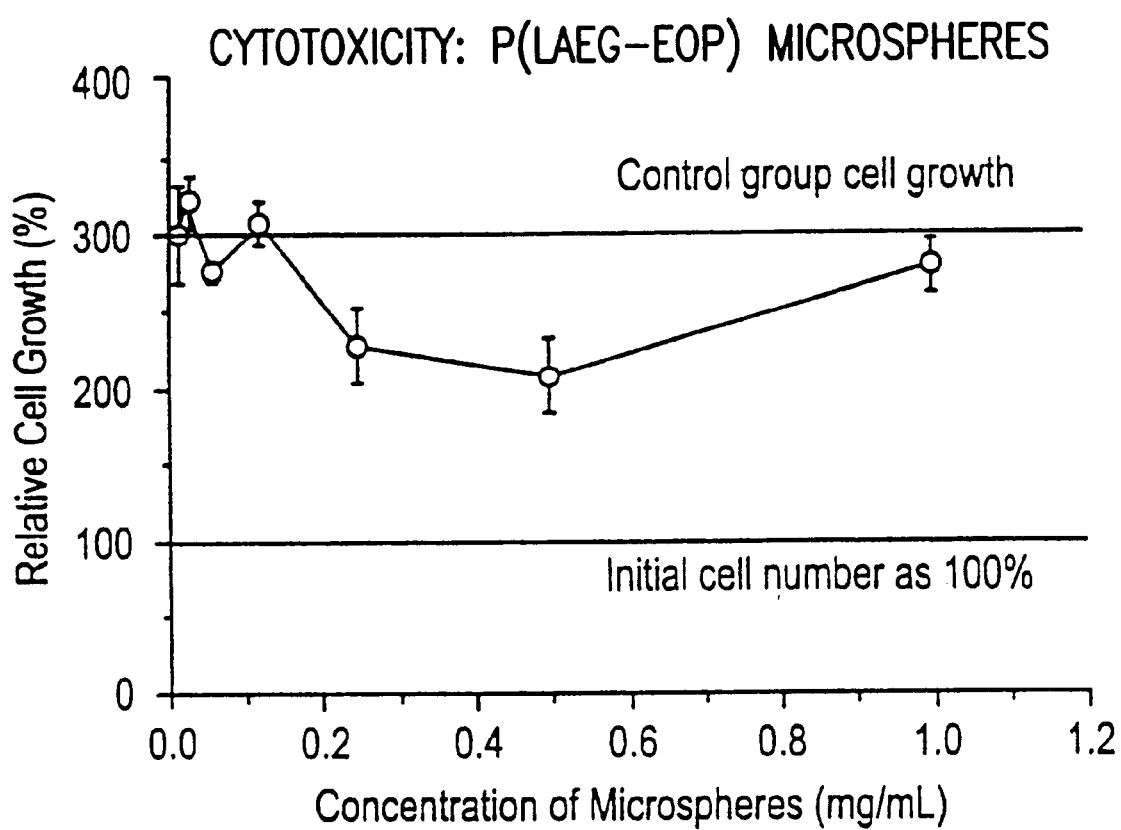
FIG. 23 shows cytotoxicity data for microspheres of a polymer of the invention, P(LAEG-EOP).

See also FIG. 23. The phosphoester copolymer P(LAEG-EOP) was shown to have an acceptable biocompatability similar to that exhibited by the PLGA reference wafer.

Similar tests were done after intramuscular injection of microspheres into male S-D rats, tabulating implant site macrophage counts, as well as irritation scores, as shown below:

| | 3 Day | | 7 Day | | 14 Day | | 31 Day | |
|---|---|---|---|---|---|---|---|---|
| Polymer | # | Irritation | # | Irritation | # | Irritation | # | Irritation |
| p (BHET-EOP/TC) 80/20 | 247 | Mild | 298 | Mild | 196 | Sl. | 32 | Sl. |
| p (BHET-EOP/TC) 82.5/17.5 | 445 | Mod. | 498 | Mod. | 406 | Mod. | 38 | Sl. |
| p (BHET-EOP/TC) 85/15 | 161 | Sl. | 374 | Mild | 586* | Mod. | 274 | Mild |
| p (CHDM-HOP) | 399 | Mild | 169 | Sl. | 762 | Sev. | 607 | Sev. |
| p (BHET-EOP/TC) 90/10 | 206 | Mild | 476 | Mod. | 557 | Mod. | 72 | Sl. |
| p (DAPG-EOP) 1:10 | 360 | Mild | 323 | Mild | 569 | Mod. | 96 | Sl. |
| PLGA (RG755) | 419 | Mod. | 331 | Mod. | 219 | Mild | 150 | Sl. |
| Control (no polymer) | 219 | Mild | — | — | — | — | — | — |

# = Mean count
* Only two animals present in this group.

Still further tests were done after subcutaneous injection into male S-D rats, tabulating implant site macrophage counts, as well as irritation scores, as shown below:

| | 7 Day | | 14 Day | | 31 Day | |
|---|---|---|---|---|---|---|
| Group | # | Irritation | # | Irritation | # | Irritation |
| Vehicle only (0.7 ml) (n = 3) | 0 | — | 0 | — | 0 | — |
| Acetic Acid (0.7 ml) (n = 3) | 208 | Mild | 166 | Sl. | 20 | Sl. |

-continued

| Group | 7 Day # | 7 Day Irritation | 14 Day # | 14 Day Irritation | 31 Day # | 31 Day Irritation |
|---|---|---|---|---|---|---|
| p (dl) Lactic Acid (89 g/kg) (0.7 ml) (n = 3) | 302 | Mild | 37 | Sl. | 0 | — |
| p (DAPG-HOP) (89 mg/kg) (0.7 ml) (n = 6) | 355 | Mild | 192 | Sl. | 101 | Sl. |
| p (CHDM-HOP) (89 mg/kg) (0.7 ml) (n = 6) | 652 | Sev. | 352 | Mild | 633 | Sev. |
| P (BHET-EOP/TC) (89 mg/kg) (0.7 ml) (n = 6) | 325 | Mild | 423 | Mod. | 197 | Sl. |
| Vehicle (2.0 ml) (n = 3) | 65 | Sl. | 0 | — | 0 | — |
| Acetic Acid (2.0 ml) (n = 3) | 267 | Mild | 334 | Mild | 32 | Sl. |
| p (dl) Lactic Acid (267 g/kg) (2.0 ml) (n = 3) | 85 | Sl. | 18 | Sl. | 279 | Mild |
| p (DAPG-HOP) (267 mg/kg) (2.0 ml) (n = 6) | 386 | Mild | 273 | Mild | 279 | Mild |
| p (CHDM-HOP) (267 mg/kg) (2.0 ml) (n = 6) | 471 | Mod. | 599 | Mod. | 618 | Sev. |
| P (BHET-EOP/TC) (267 mg/kg) (2.0 ml) (n = 6) | 292 | Mild | 327 | Mild | 178 | Sl. |

# = Mean count

Example 27

Preparation of Copolymer Microspheres Containing FITC-BSA with 10% Theoretical Loading Level One hundred mL of FITC-BSA solution (100 mg/mL dissolved in water) was added to a solution of 100 mg of P(LAEG-EOP) in 1 mL of methylene chloride, and emulsified via sonication for 15 seconds on ice. The resulting emulsion was immediately poured into 5 mL of vortexing a 1% solution of polyvinyl alcohol (PVA) in 5% NaCl, and vortexing was maintained for one minute. The emulsion thus formed was then poured into 20 mL of a 0.3% PVA solution in 5% NaCl, which was being stirred vigorously. Twenty five mL of a 2% solution of isopropanol was added, and the mixture was kept stirring for one hour to ensure complete extraction. The resulting microspheres were collected via centrifugation at 3000×g, washed 3 times with water, and freeze dried.

Different formulations of microspheres were made by using as the second aqueous phase a 5% NaCl solution or a 5% NaCl solution also containing 1% PEG 8000. Yet another technique was used in evaporating the solvent by stirring the mixture overnight, thus forming microspheres by solvent evaporation.

Example 28

Estimation of Encapsulation Efficiency and Loading Level

The loading level of FITC-BSA was determined by assaying for FITC after hydrolyzing the microspheres with 0.5 N NaOH overnight. The amount of FITC-BSA was compared with a standard curve that had been generated by making a series of FITC-BSA solutions in 0.5 N NaOH. The encapsulation efficiency of the microspheres was determined by comparing the quantity of FITC-BSA entrapped with the initial amount in solution via fluorometry. The encapsulation efficiency (%) and loading level (%) of FITC-BSA are shown in Table 10 below.

TABLE 10

Encapsulation Efficiency and Loading Level of FITC-BSA

| | Loading (%) | |
|---|---|---|
| | High Loading (24.98%) | Low Loading (1.5%) |
| Encapsulation Efficiency (%) | 98.10 | 91.70 |

Example 29

Cytotoxicity of the Copolymer

Figure 24A:
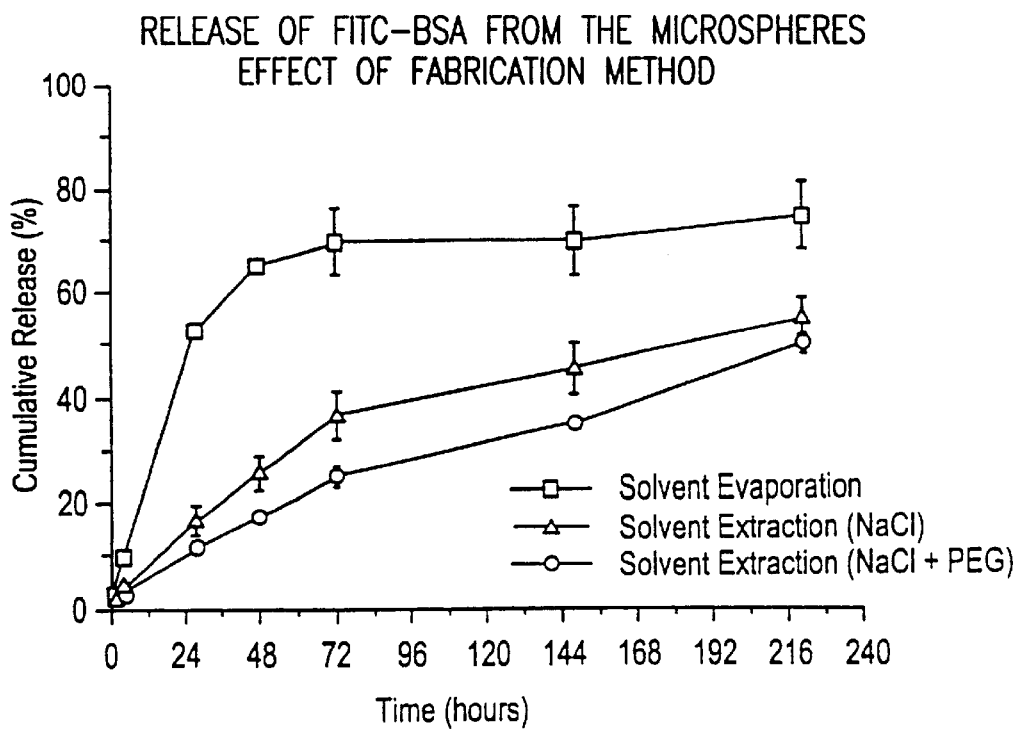
FIG. 24A shows the effect of fabrication method upon the release rate of microspheres of a polymer of the invention.
Figure 24B:
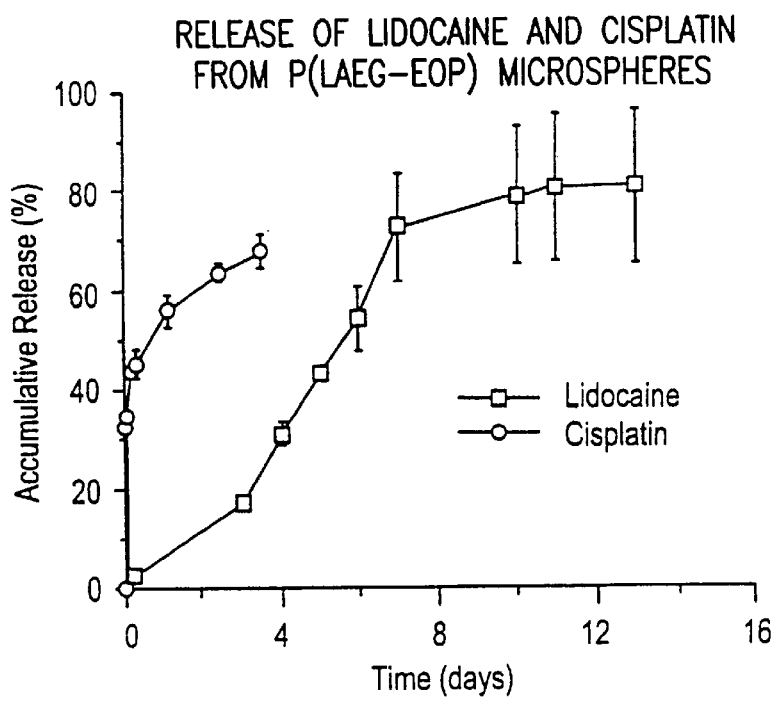
FIG. 24B shows the rate of release of lidocaine from microspheres of a polymer of the invention.
Figure 25A:
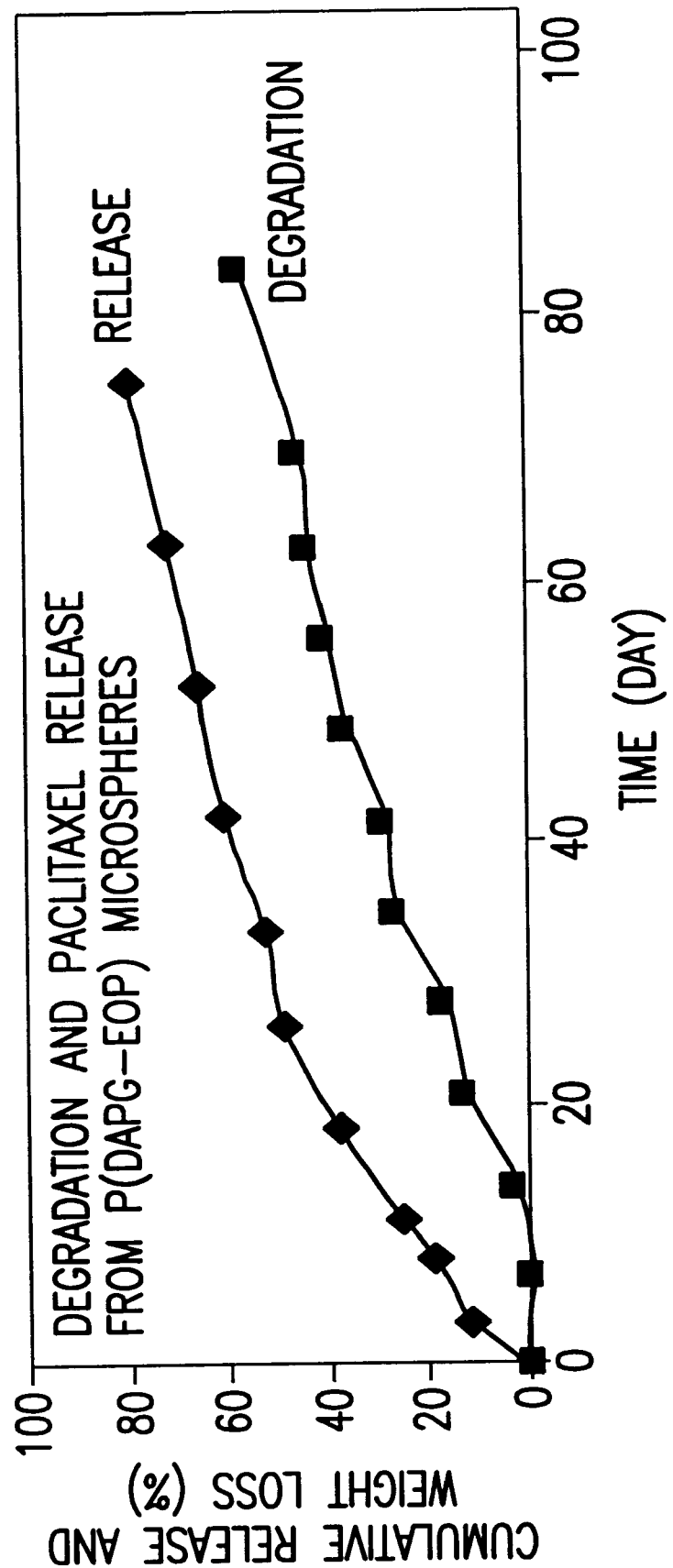
FIGS. 25(A) through 25(E) all show degradation and release data of p(DAPG-EOP) polymers in vitro.
Figure 25B:
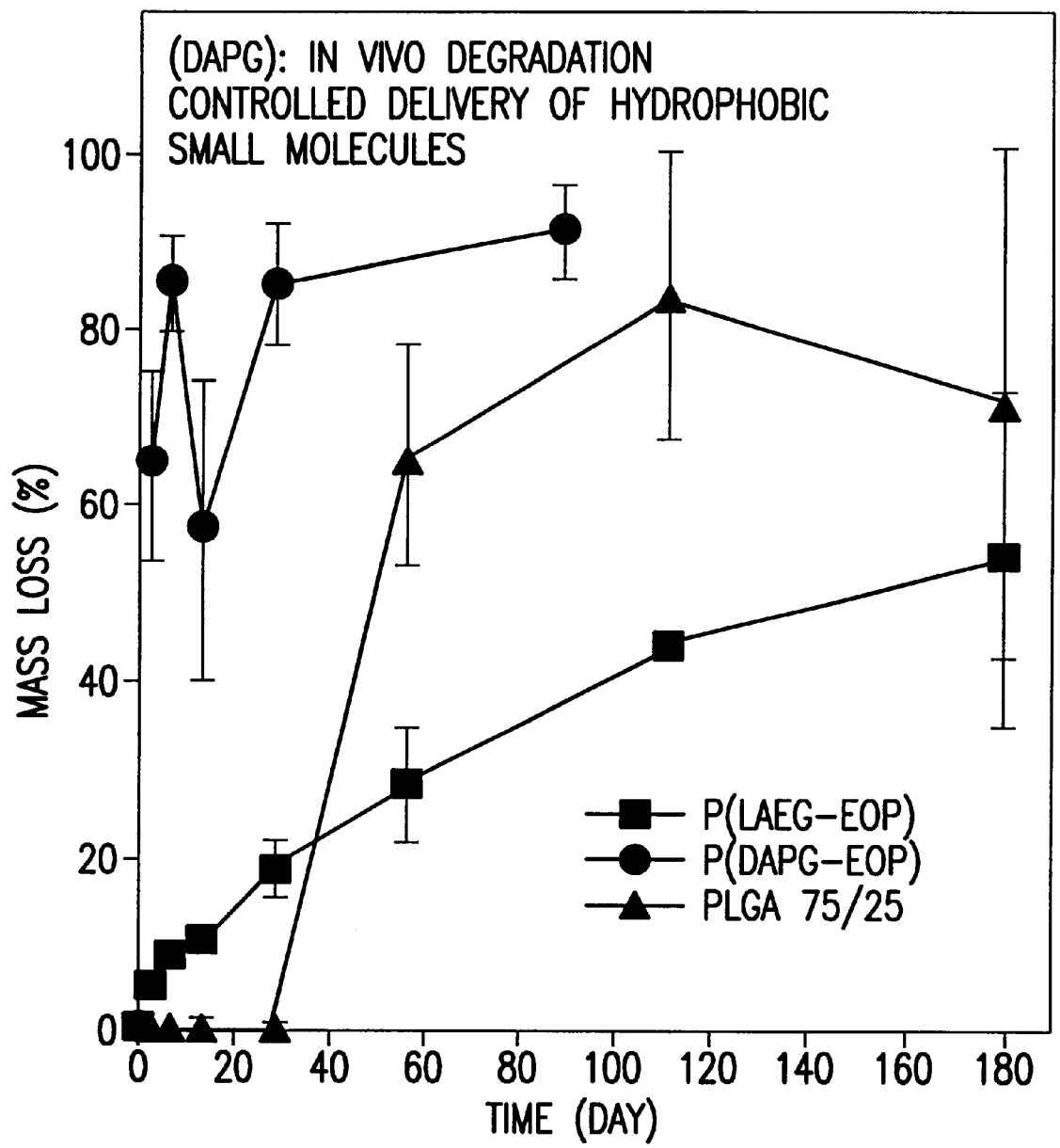
Figure 25C:
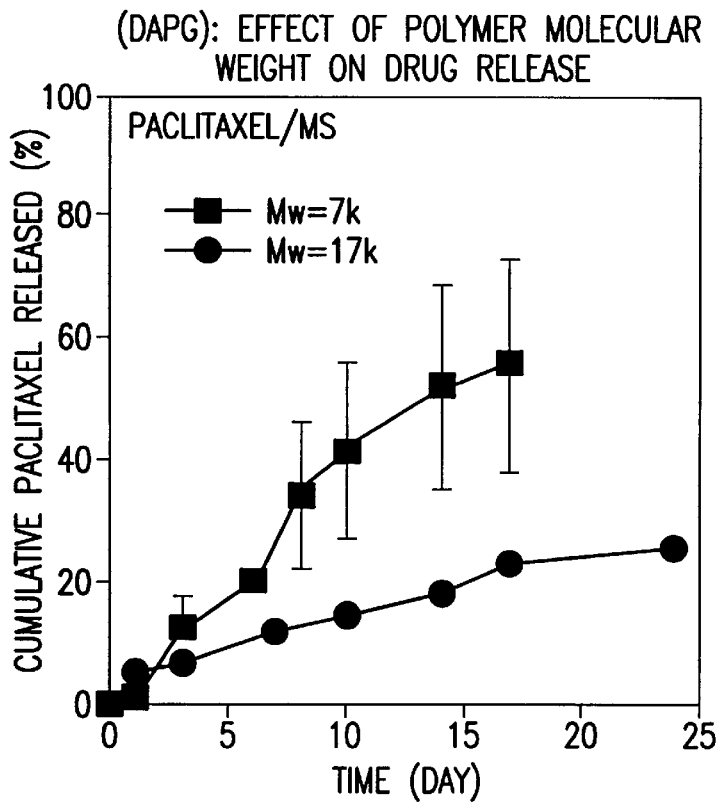
Figure 25D:
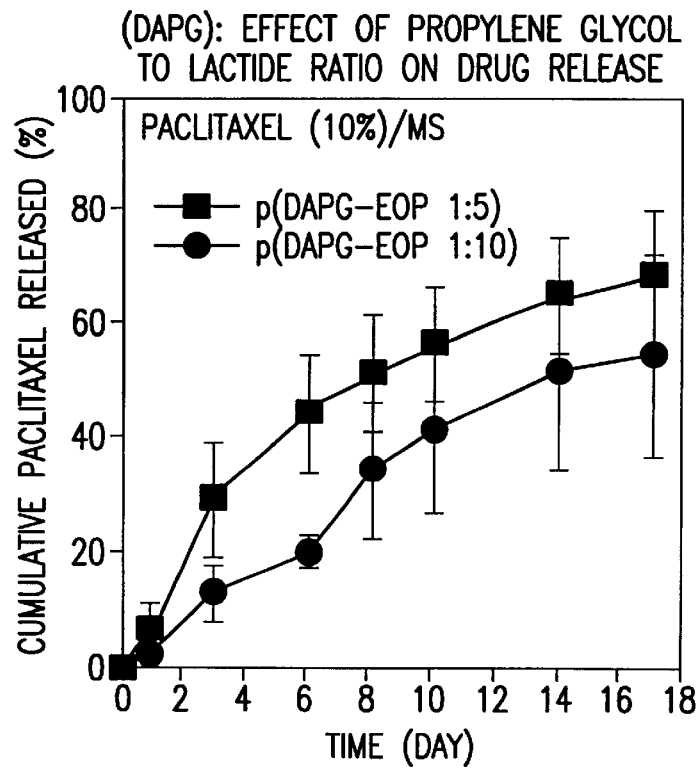
Figure 25E:
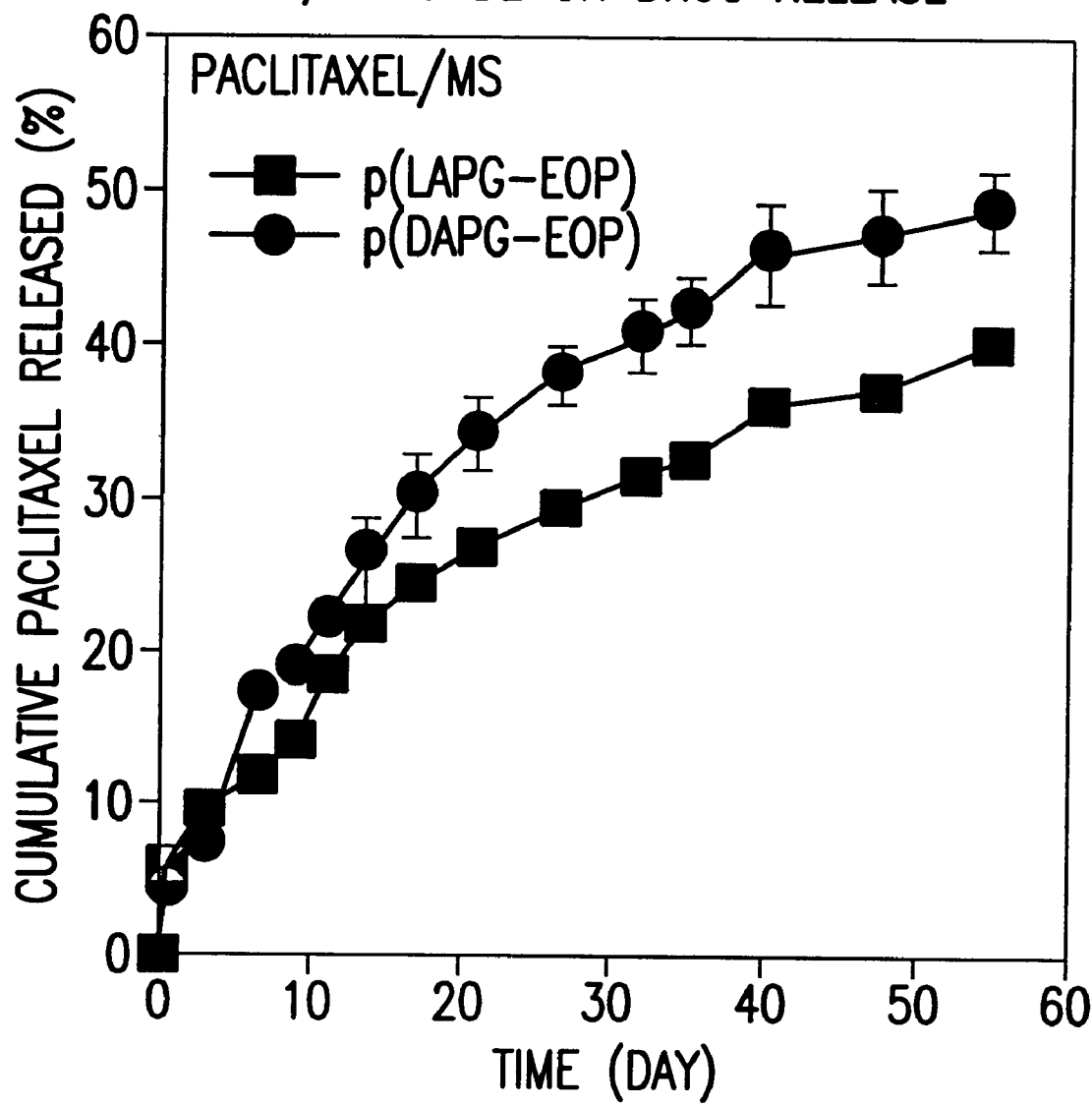
Figure 26A:
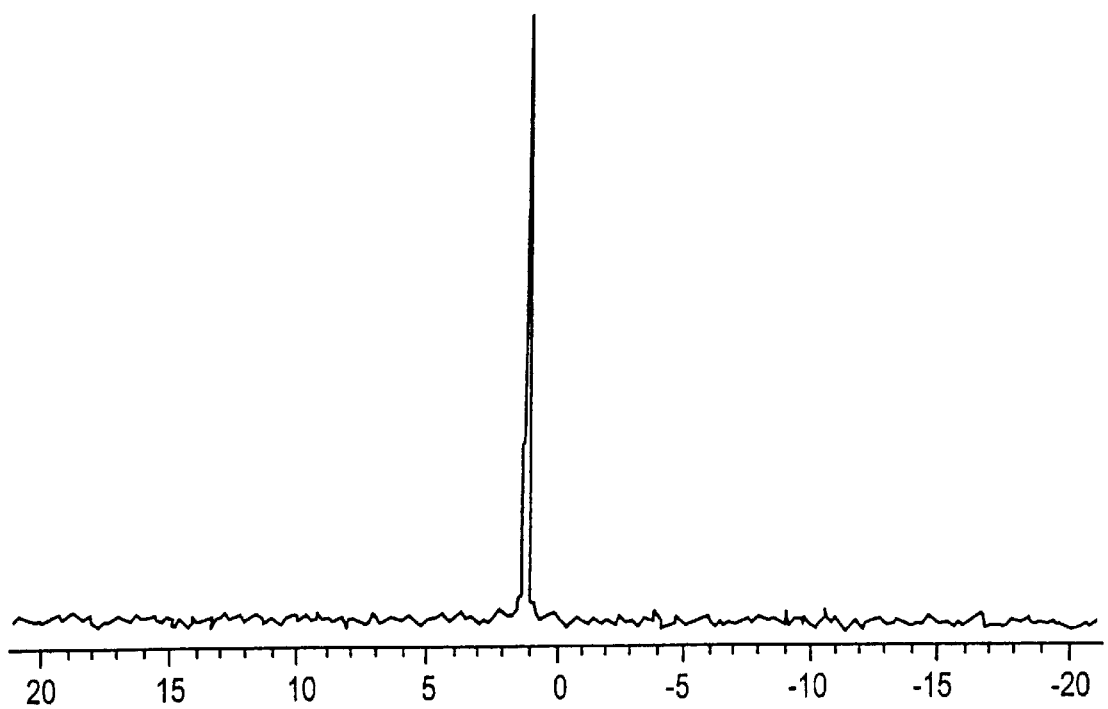
FIG. 26 shows the structure of P(trans-CHDM-HOP) as determined by $^{31}$P-NMR and $^{1}$H-NMR.
Figure 26B:
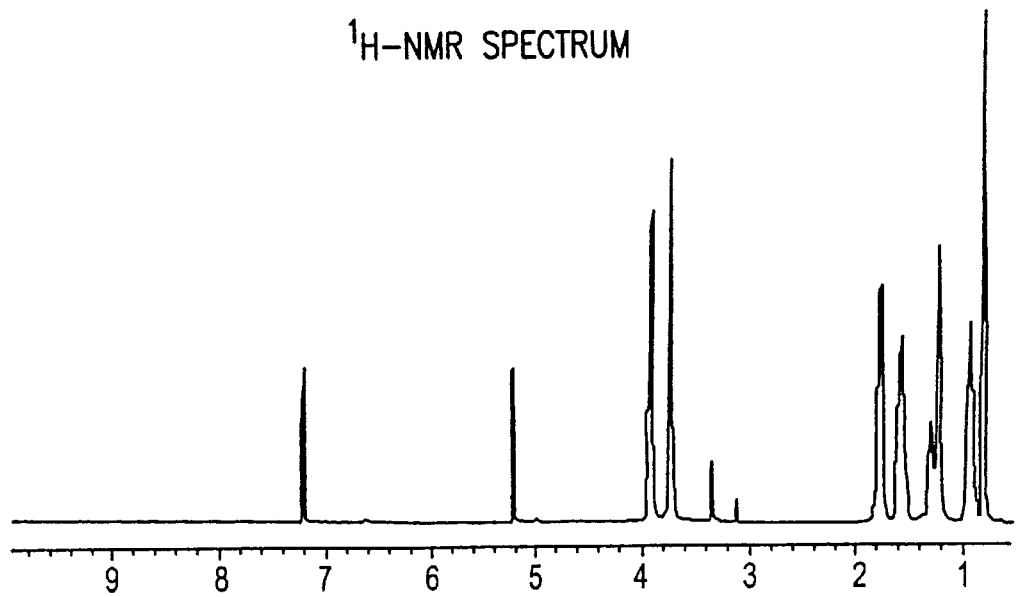

Microspheres containing P(LAEG-EOP) were added to 96-well tissue culture plates at different concentrations. Human gastric carcinoma cells (GT3TKB) were then seeded at a rate of $10^4$ cells/well. The cells were then incubated with the microspheres in the wells for 48 hours at 37° C. The cell proliferation rate was analyzed by MTT assay, and the results were plotted as % relative growth vs. concentration of copolymer microspheres in the tissue culture well, as shown in FIG. 24.

Example 30

Effect of Fabrication Method on the Release of FITC-BSA from Microspheres

Fifty mg of microspheres of a polymer of the invention were suspended in vials containing 10 mL of PBS, and the vials were shaken in an incubator at 37° C. and at a rate of 220 rpm. The supernatant fluid was replaced at various time points, and the amount of FITC-BSA released was analyzed by spectrophotometry at 492 nm. The results were plotted as % cumulative release of FITC-BSA from the microspheres vs. time in hours, as shown in FIG. 25.

Example 31

Preparation of P(LAEG-EOP) Microspheres Containing Lidocaine Using Polyvinyl Alcohol as the Non-Solvent Phase A solution of 0.5% w/v polyvinyl alcohol (PVA) in deionized water solution was prepared in a 600 mL beaker by combining 1.05 g of PVA with 210 mL of deionized water. The solution was stirred for one hour and filtered. A polymer/drug solution was prepared by combining 630 mg of polymer and 70 mg of lidocaine in 7 mL of methylene chloride and mixing by vortex. The PVA solution was mixed at 500 rpm with an overhead mixer, and the polymer/drug solution was added dropwise. After 30 minutes of mixing, 200 mL of cold deionized water was added to the stirring PVA solution. The resulting mixture was stirred for a total of 3.5 hours. The microspheres formed were filtered off, washed with deionized water, and lyophilized overnight.

Microspheres loaded with 4.2% w/w lidocaine were thus obtained. Approximately 10 mg of microspheres were placed in a phosphate buffer saline (0.1M, pH 7.4) at 37° C. on a shaker and sampled regularly. The results were plotted as % lidocaine released vs. time in days, as shown in FIG. 25.

Example 32

Synthesis of P(DAPG-EOP)

The d,l racemic mixture of poly(L-lactide-co-propylphosphate) ["P(DAPG-EOP)"] was prepared as follows:

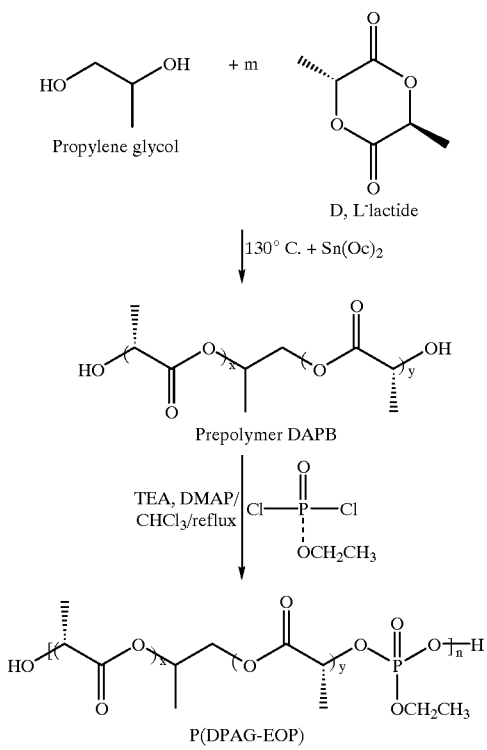

The product was obtained as a white solid soluble in organic solvents. Depending on reaction conditions, different intrinsic viscosities and different molecular weights were obtained, as shown below in summary form:

| Base(s) | Reaction Time/Temp | Eq EOPCl$_2$ | Mw | IV |
|---|---|---|---|---|
| 3.0 eq Reillex | 18 hrs/reflux | 1.05 | — | 0.06 |
| 3.0 eq Reillex | 40 hrs/reflux | 1.05 | — | 0.06 |
| 3.0 eq Reillex & 0.1% (w/w) DMAP | 18 hrs/reflux | 1.05 | — | 0.08 |
| 3.0 eq Reillex | 18 hrs/reflux | 1.00 | — | 0.06 |
| 2.5 eq TEA; 0.5 eq DMAP | 15 mins/ room temp. | 1.05 | — | 0.42 |
| 2.5 eq TEA; 0.5 eq DMAP | 18 hrs/reflux | 1.05 | — | 0.27 |
| 2.5 eq TEA; 0.5 eq DMAP | about 2.5 days/ reflux | 1.05 | — | 0.39 |
| 2.5 eq TEA; 0.1 eq DMAP | 1 h/4° C.; 2 h/room temp. | 1.01 | — | 0.06 |
| 2.5 eq TEA; 0.5 eq DMAP | 1 h/4° C.; 2 h/room temp. | 1.01 | 91,100 | 0.47 |
| 2.5 eq TEA; 0.5 eq DMAP | 1 h/4° C.; 2 h/room temp. | 1.01 | 95,900 (Mn 44,200; Mw/Mn 2.2) | 0.42 |
| 1.1 eq DMAP | 1 h/4° C.; 2 h/room temp. | 1.01 | — | 0.08 |
| 1.5 eq TEA; 0.5 eq DMAP | 1 h/4° C.; 2 h/room temp. | 1.01 | — | 0.23 |
| 2.5 eq TEA; 0.5 eq DMAP | 1 h/4° C.; 17 h/room temp. | 1.00 | 28,400 | 0.25 |
| 2.5 eq TEA; 0.5 eq DMAP | 1 h/4° C.; 2 h/room temp. | 1.00 | 26,800 (Mn 12,900; Mw/Mn 2.1) | 0.23 |
| 2.5 eq TEA; 0.5 eq DMAP | 1 h/4° C.; 2 h/room temp. | 1.01 | 14,700 | 0.16 |
| 2.5 eq TEA; 0.5 eq DMAP | 1 h/4° C.; 2 h/room temp. | 1.01 | 32,200 (Mn 13,000; Mw/Mn 2.5) | 0.32 |
| 3.0 eq DMAP | 1 h/4° C.; 2 h/room temp. | 1.00 | — | 0.20 |
| 2.5 eq TEA; 0.5 eq DMAP | 1 h/4° C.; 2 h/room temp. | 1.00 | — | 0.22 |

Example 33

Preparation of P(DAEG-EOP) Microspheres With Lidocaine Using Silicon Oil as the Non-solvent Phase Two percent sorbitan-trioleate, which is commercially available from Aldrich under the tradename Span-85, in silicon oil was prepared in a 400 mL beaker by combining 3 mL of Span-85 with 150 mL of silicone oil and mixing with an overhead stirrer set at 500 rpm. A d,l racemic mixture of poly(L-lactide-co-ethyl-phosphate) P(DAEG-EOP) polymer/drug solution was prepared by dissolving 400 mg of the polymer prepared above in Example 33, and 100 mg of lidocaine in 4.5 mL of methylene chloride. The resulting polymer/drug solution was added dropwise to the silicone oil/span mixture with stirring. The mixture was stirred for an hour and 15 minutes. The microspheres thus formed were filtered off and washed with petroleum ether to remove the silicone oil/span mixture, and lyophilized overnight.

450 mg of microspheres loaded with 7.6% w/w lidocaine were thus obtained. Approximately 10 mg of microspheres were placed in phosphate buffer saline (0.1M, pH 7.4) at 37° C. on a shaker and sampled regularly. The results were plotted as % lidocaine released vs. time in days.

Similar data for P(DAPG-EOP) microspheres containing paclitaxel was obtained, as shown in FIGS. 26A, 26B, 26C, 26D, 26E and 26F.

Example 34

Biocompatibility of Poly(phosphoester) Microspheres in Mouse Peritoneal Cavity

The biocompatibility of biodegradable poly (phosphoester) microspheres of the invention was tested as follows:

Three 30 mg/mL samples of lyophilized poly(L-lactide-co-ethyl-phosphate) microspheres were prepared, the first having diameters greater than 75 microns, the second having diameters within the range of 75–125 microns, and the third having diameters within the range of 125–250 microns. Each sample was injected intra-peritoneally into a group of 18 female CD-1 mice having a starting body weight of 25 g. Animals in each group were weighed, sacrificed, and necropsied at 2, 7 and 14 days, and at 1, 2 and 3 months. Any lesions detected during the necropsy were graded on a scale of 0 to 4, with 0 indicating no response to treatment and 4 indicating a severe response to treatment.

Inflammatory lesions were observed to be restricted to an association with the microspheres on peritoneal surfaces or within fat tissue, and were compatible with foreign body isolation and encapsulation. Focal to multifocal supportive peritoneal steatitis with mesothelial hyperplasia was observed at 2–7 days, but gradually resolved by macrophage infiltration, the formation of inflammatory giant cells, and fibrous encapsulation of the microspheres at later sacrifices. Occasional adherence of microspheres to the liver and diaphragm, with associated inflammatory reaction, was also seen. Lesions related to microspheres were not seen within abdominal or thoracic organs. Microspheres, which were detected throughout the duration of the study, appeared transparent at early sacrifices but, at later times, developed crystalline material internally. No effects on body growth were observed. The peritoneal reaction was observed to be limited to areas directly adjacent to the microspheres with no apparent deleterious effects on major thoracic or abdominal organs.

Similar intraperitoneal injection of DAPG-EOP into male and female S-D rats gave the following results:

| Dose Level | Test | Initial No. in Test | | Cumulative Mortality[a] | |
|---|---|---|---|---|---|
| (mg/kg) | Material | M | F | M | F |
| 0 | 10% Dextran 40 in 0.9% Saline | 25 | 25 | 0 | 0 |
| 30 | DAPG-EOP | 25 | 25 | 1 | 0 |
| 100 | DAPG-EOP | 25 | 25 | 0 | 0 |
| 300 | DAPG-EOP | 25 | 25 | 0 | 0 |

[a]Represents animals found dead or sacrificed in moribund condition during study period. M = Male; F = Female Example 35

Synthesis of the Poly(phosphoester) p(trans-CHDM-HOP)

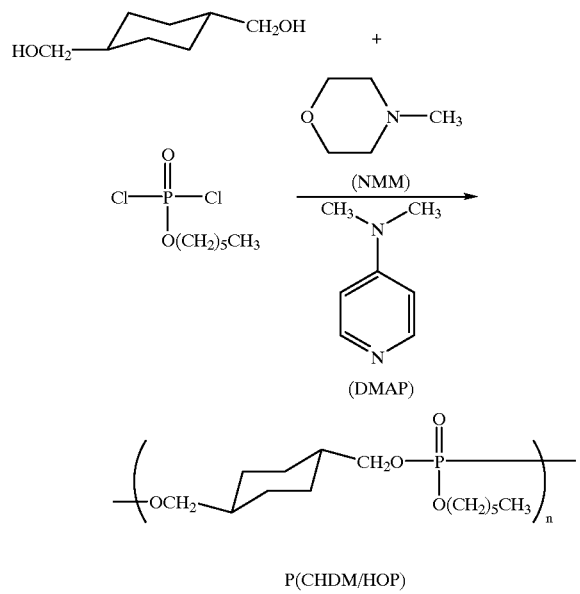

P(CHDM/HOP)

Under an argon stream, 10 g of trans-1,4-cyclohexane dimethanol (CHDM), 1.794 g of 4-dimethylaminopyridine (DMAP), 15.25 ml (14.03 g) of N-methyl morpholine (NMM), and 50 ml of methylene chloride, were transferred into a 250 ml flask equipped with a funnel. The solution in the flask was cooled down to −15° C. with stirring, and a solution of 15.19 g of hexyl phosphorodichloridate (HOP) in 30 ml of methylene chloride was added through the funnel. The temperature of the reaction mixture was raised to the boiling point gradually and maintained at reflux temperature overnight.

Figure 27A:
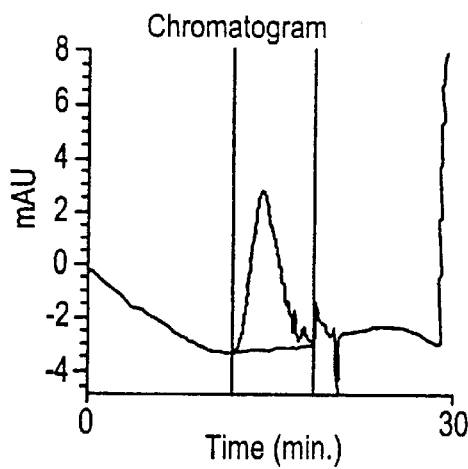
FIG. 27 shows the chromatogram and molecular weight distribution for P(cis-/trans-CHDM-HOP).
Figure 27B:
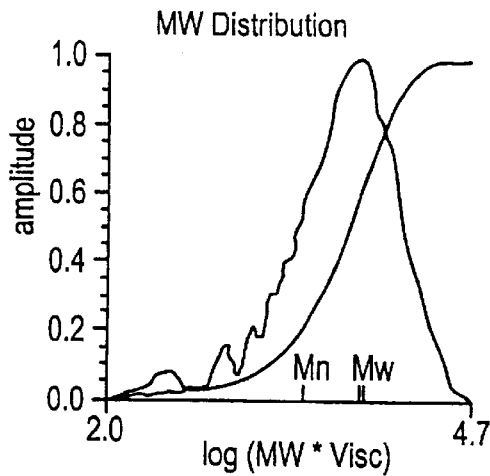
Figure 27C:
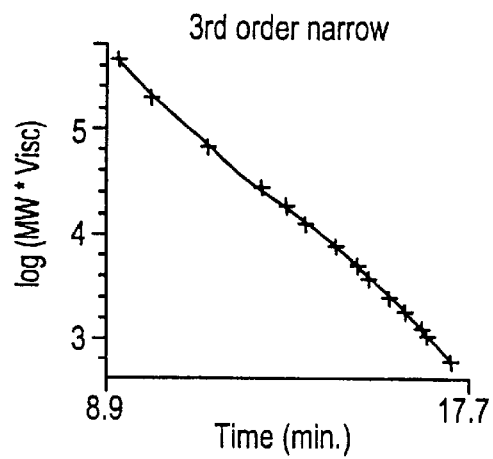
Figure 28A:
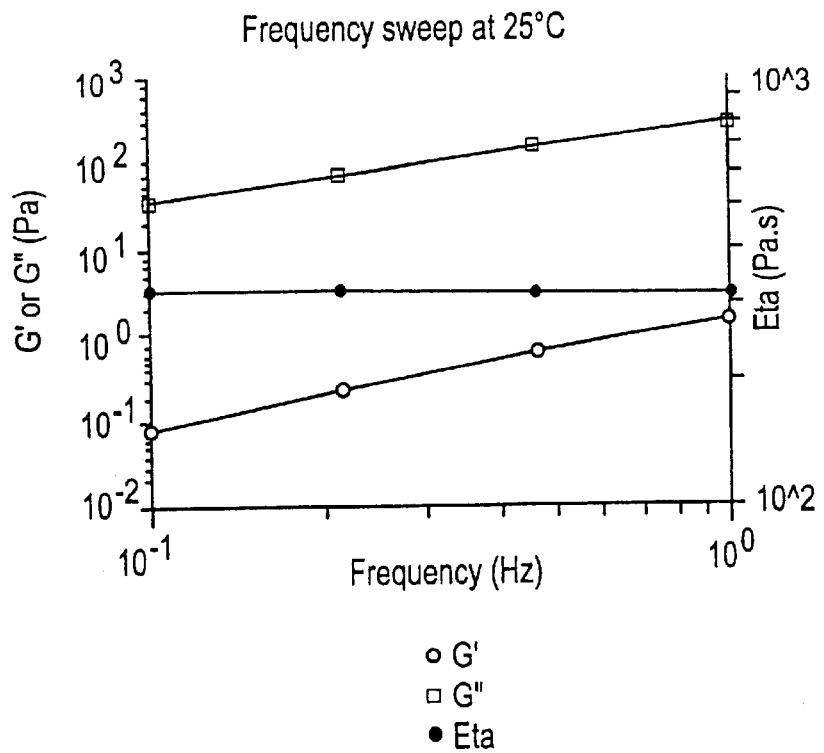
FIG. 28A graphically represents the active energy as a function of frequency of P(trans- CHDM-HOP)
Figure 28B:
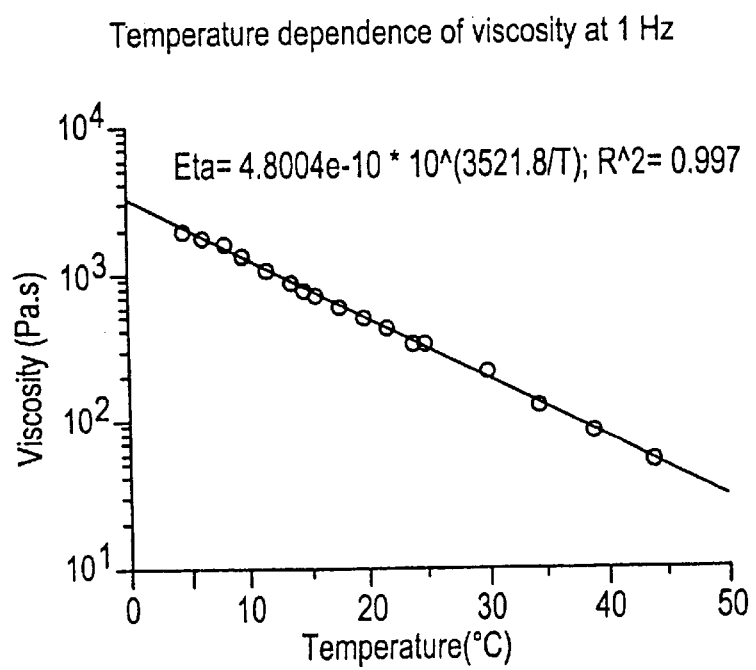
FIG. 28B shows the corresponding viscosity.

The reaction mixture was filtered, and the filtrate was evaporated to dryness. The residue was re-dissolved in 100 ml of chloroform. This solution was washed with 0.1 M solution of a mixture of HCl and NaCl, dried over anhydrous $Na_2SO_4$, and quenched into 500 ml of ether. The resulting flowable precipitate was collected and dried under vacuum to form a clear pale yellow gelatinous polymer with the flow characteristics of a viscous syrup. The yield for this polymer was 70–80%. The structure of P(trans-CHDM-HOP) was ascertained by $^{31}$P-NMR and $^1$H-NMR spectra, as shown in FIG. 27, and by FT-IR spectra. The molecular weights (Mw=8584; Mn=3076) were determined by gel permeation chromatography (GPC), as shown in FIG. 28, using polystyrene as a calibration standard.

Example 36

Synthesis of the Poly(Phosphoester) P(cis & trans-CHDM-HOP)

Poly(phosphoester) P(cis/trans-1,4-cyclohexane-dimethanol hexyl phosphate) was prepared by following the procedure described above in Example 34 except that a mixture of cis- and trans-1,4-cyclohexanedimethanol was used as the starting material. As expected, the product cis-/trans-P(CHDM-HOP) was less viscous than the trans isomer obtained in Example 34.

Example 37

Synthesis of Low Molecular Weight P(CHDM-HOP)

Under an argon stream, 10 g of trans-1,4-cyclohexane dimethanol (CHDM), 15.25 mL (14.03 g) of N-methyl morpholine (NMM), and 50 mL of methylene chloride were transferred into a 250 mL flash equipped with a funnel. The solution in the flask was cooled down to −40° C. with stirring. A solution of 15.19 g of hexyl phosphoro-dichloridate (HOP) in 20 mL of methylene chloride was added through the funnel, and an additional 10 mL of methylene chloride was used to flush through the funnel. The mixture was then brought up to room temperature gradually and kept stirring for four hours.

The reaction mixture was filtered, and the filtrate was evaporated to dryness. The residue was re-dissolved in 100 ml of chloroform. This solution was washed with 0.5 M mixture of HCl-NaCl solution, washed with saturated NaCl solution, dried over anhydrous $Na_2SO_4$, and quenched into a 1:5 ether-petroleum mixture. The resulting oily precipitate was collected and dried under vacuum to form a clear, pale yellow viscous material. The structure of the product was confirmed by $^1$H-NMR, $^{31}$P-NMR and FT-IR spectra.

Example 38

Synthesis of the Poly(phosphoester) P(trans-CHDM-BOP)

-continued

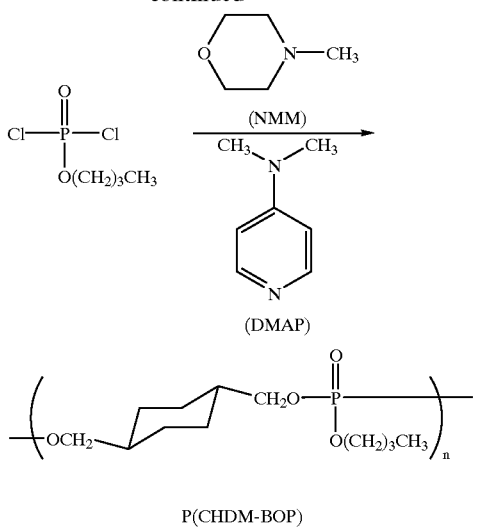

P(CHDM-BOP)

Under an argon stream, 10 g of trans-1,4-cyclohexane dimethanol (CHDM), 0.424 g (5%) of 4-dimethylaminopyridine (DMAP), 15.25 mL (14.03 g) of N-methyl morpholine (NMM) and 50 mL of methylene chloride were transferred into a 250 mL flask equipped with a funnel. The solution in the flask was cooled down to −40° C. with stirring. A solution of 13.24 g of butyl phosphorodichloridate (BOP) in 20 mL of methylene chloride was added through the funnel, with an additional 10 mL of methylene chloride being used to flush through the funnel. The mixture was heated to the boiling point gradually, and kept refluxing for four hours. The reaction mixture was filtered, and the filtrate was evaporated to dryness, taking care to keep the temperature below 60° C. The residue was redissolved in 100 mL of chloroform. The solution formed was washed with 0.5 M of HCl-NaCl solution and saturated NaCl solution, dried over anhydrous $Na_2SO_4$, and quenched into a 1:5 ether-petroleum mixture. The resulting oily precipitate was collected and dried under vacuum to produce a clear, pale yellow viscous material.

Example 39

Rheological Properties of P(trans-CHDM-HOP)

Figure 29A:
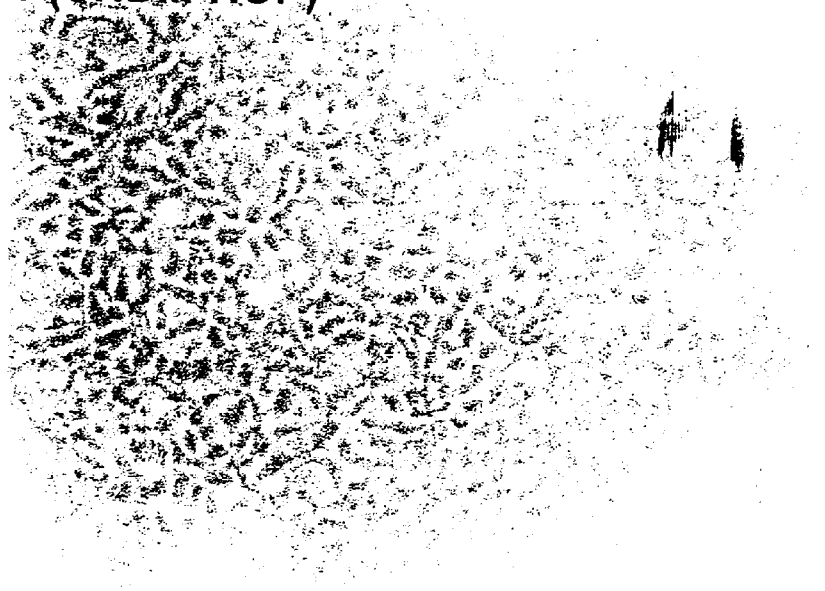
FIG. 29A shows HEK293 cells grown on a P(CHDM-HOP) surface after 72 hours of incubation.
Figure 29B:
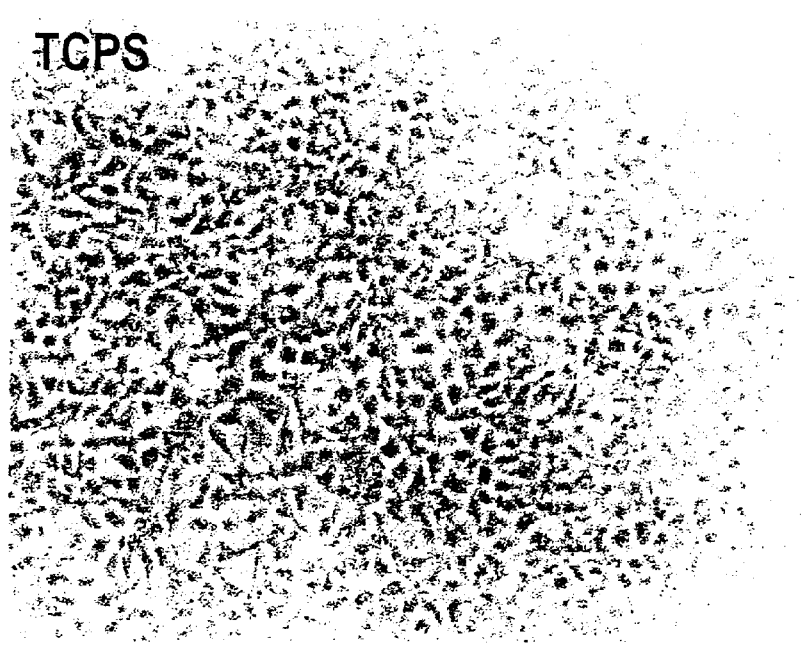
FIG. 29B shows HEK293 cells grown on a TCPS surface after 72 hours' incubation.

P(trans-CHDM-HOP) remained in a flowable gel-like state at room temperature. The polymer exhibited a steady viscosity of 327Pa·s at 25° C. (shown in FIG. 29B), and a flowing active energy of 67.5 KJ/mol (shown in FIG. 29A).

Example 40

In Vitro Cytotoxicity of P(trans-CHDM-HOP)

Figure 30:
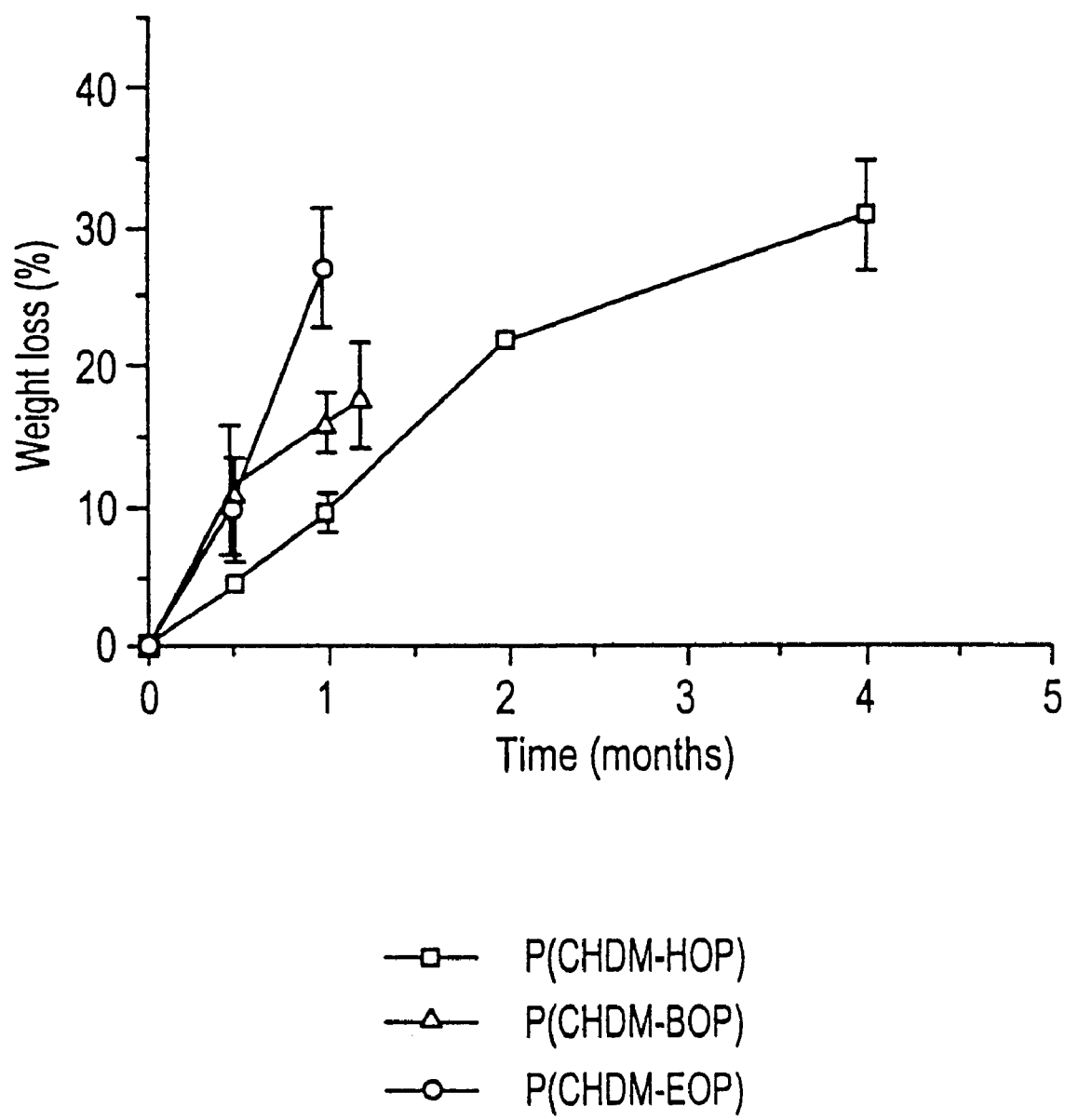
FIG. 30 graphically represents the effect of the side chain structure on the in vitro degradation rate of three poly (phosphoesters) of the invention in phosphate buffer solution.

Cover slips were coated with P(trans-CHDM-HOP) by a spin coating method. The coated coverslips were then dried and sterilized by UV irradiation overnight under a hood. A P(trans-CHDM-HOP)-coated cover slip was placed at the bottom of each well of a 6-well plate. $5 \times 10^5$ HEK293 (human embryonic kidney) cells were plated into each well and cultured for 72 hours at 37° C. The resulting cell morphology was examined, using tissue culture polystyrene (TCPS) as a positive control. The cells growing on the P(CHDM-HOP) surface proliferated at a slightly slower rate, as shown by FIG. 30. However, the morphology of cells grown on the polymer surface was similar to the morphology of cells grown on the TCPS surface.

Example 41

In Vitro Degradation of P(CHDM-Alkyl Phosphates)

Each of the following poly(phosphate)s was prepared as described above:

TABLE 11

| Polymer | Side Chain |
|---------|------------|
| P (CHDM-HOP) | -O-hexyl group |
| P (CHDM-BOP) | -O-butyl group |
| P (CHDM-EOP) | -O-ethyl group |

Figure 31:
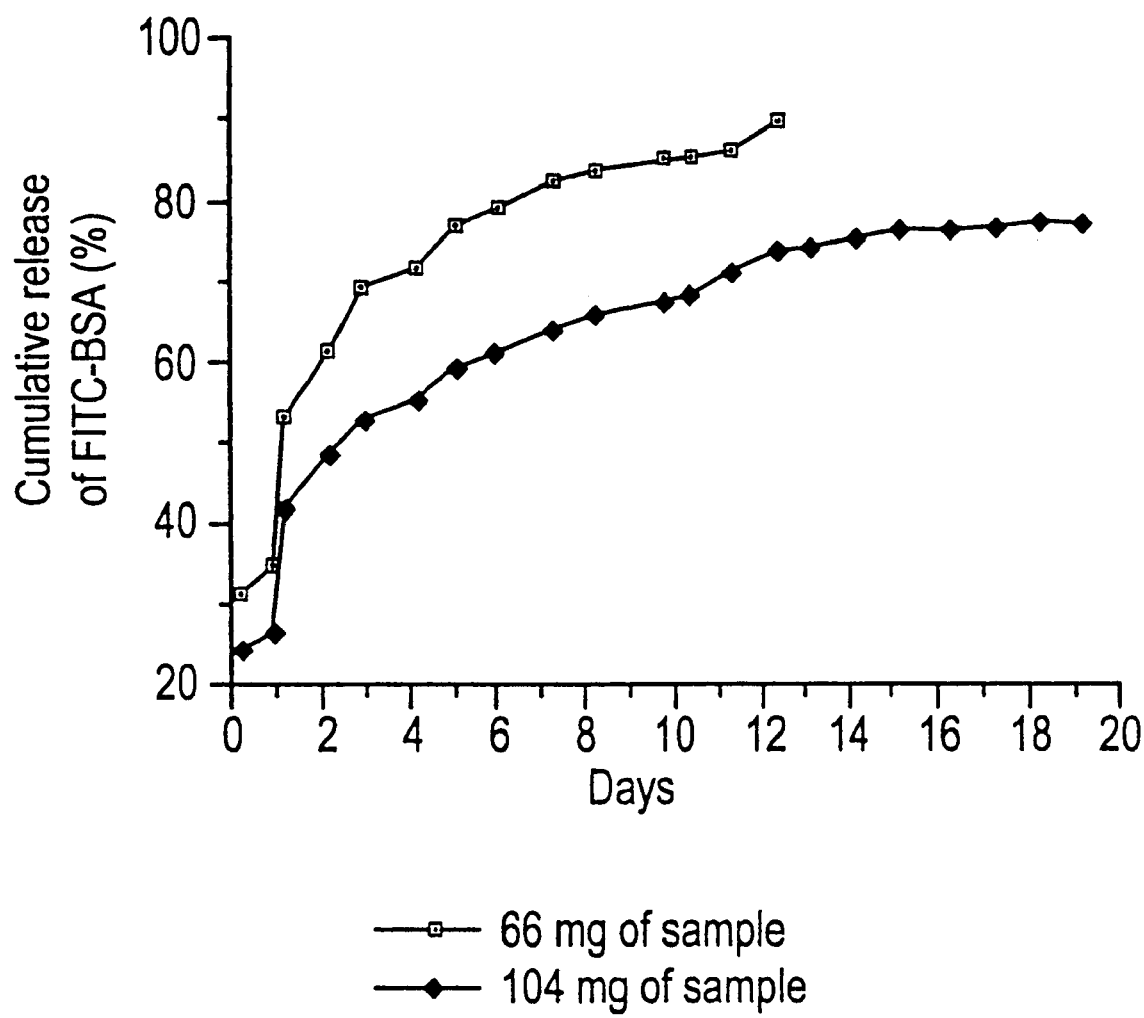
FIG. 31 shows the release curves of the bio-macromolecule FITC-BSA from the polymer P(CHDM-HOP) at 33% loading.

A sample of 50 mg of each polymer was incubated in 5 mL of 0.1 M, pH 7.4 phosphate buffer saline (PBS) at 37° C. At various points in time, the supernatant was poured out, and the polymer samples were washed three times with distilled water. The polymer samples were then extracted with chloroform, and the chloroform solution was evaporated to dryness. The residue was analyzed for weight loss by comparing with the original 50 mg sample. FIG. 31 graphically represents the effect of the side chain structure on the in vitro degradation rate of poly(phosphates) in PBS.

Example 42

In Vitro Release Profile of Protein by P(CHDM-HOP)

Figure 32:
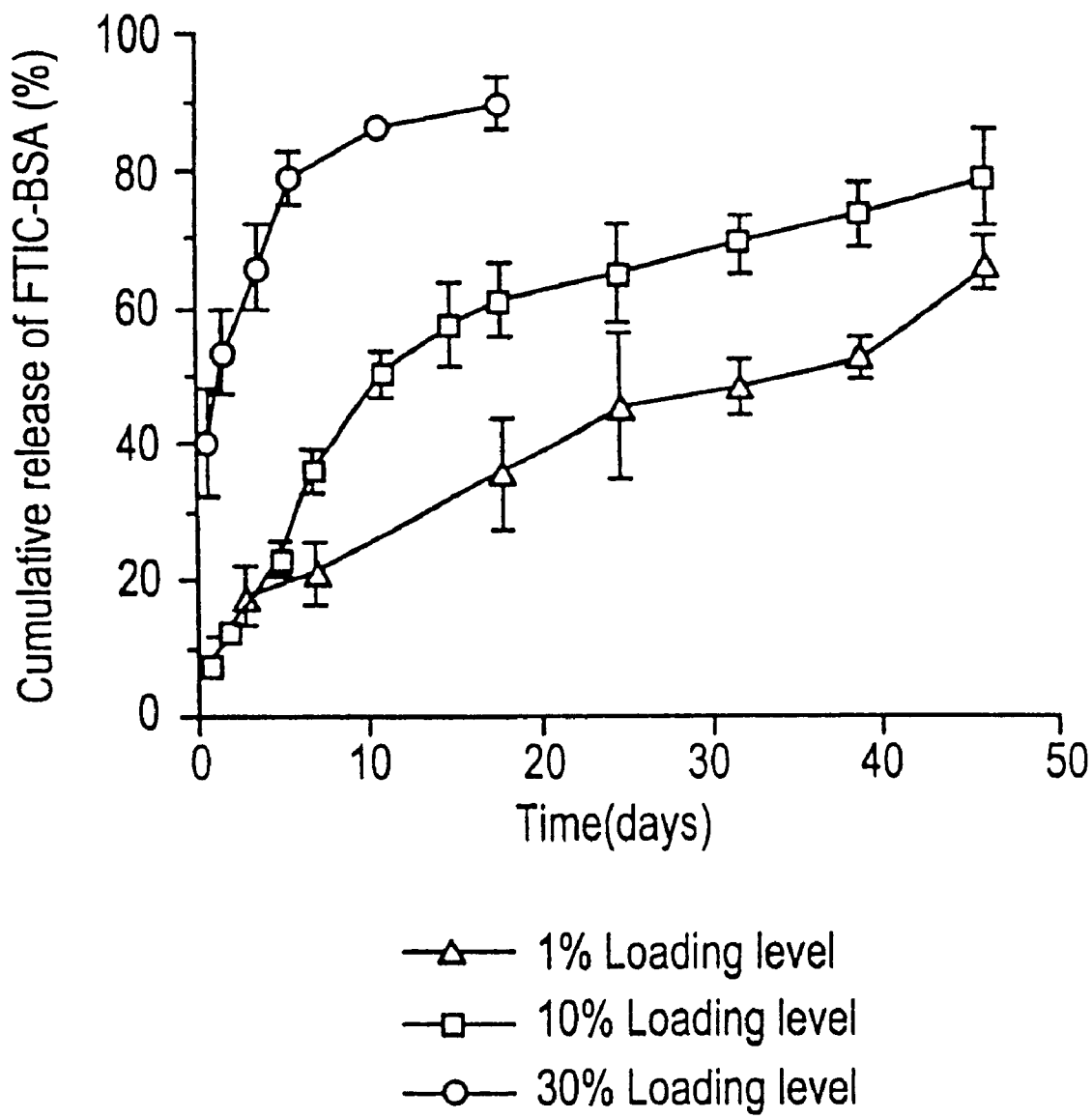
FIG. 32 graphically represents the in vitro release kinetics of FITC-BSA as a function of a loading levels of 30%, 10% and 1%.
Figure 33:
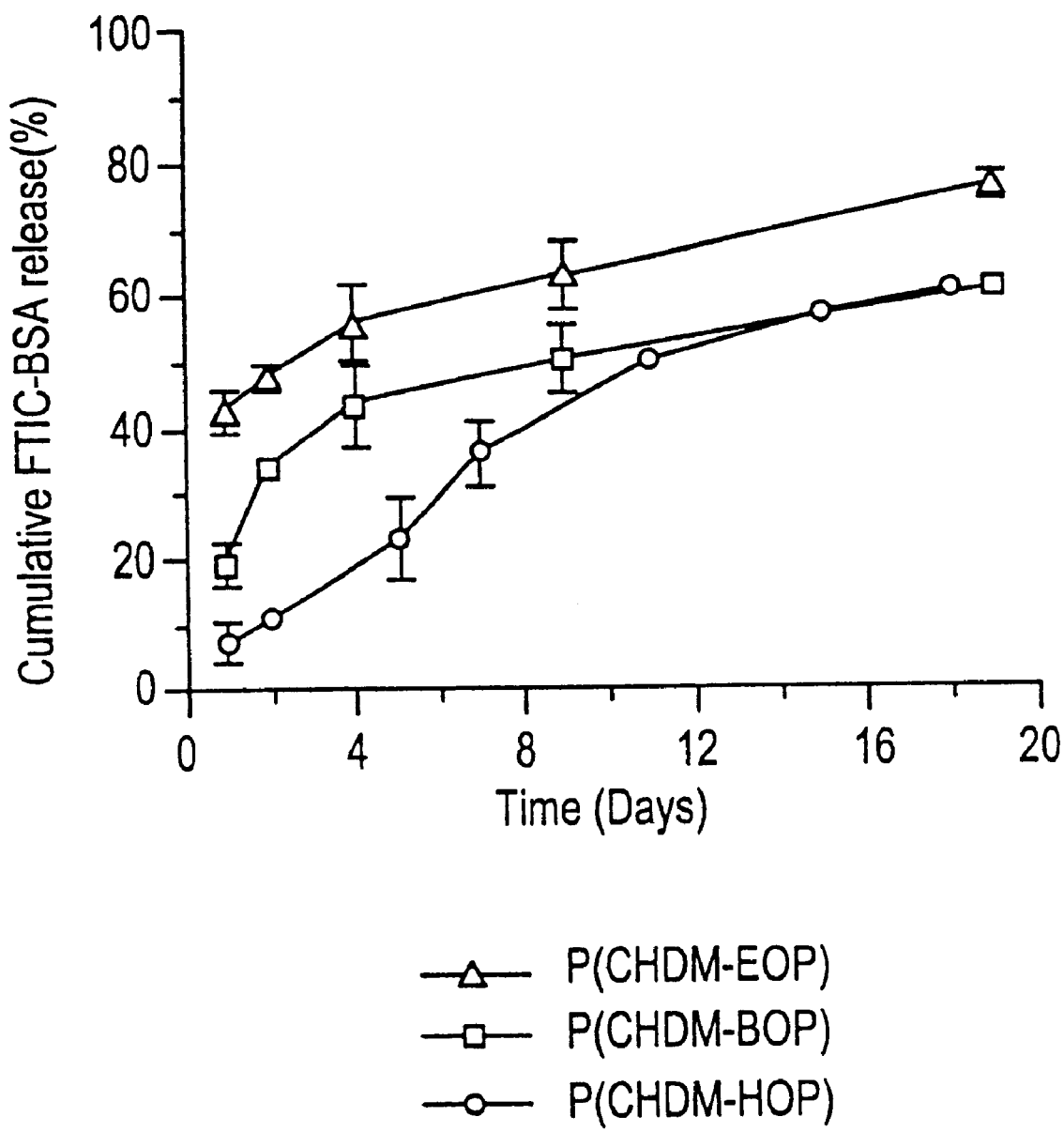
FIG. 33 graphically represents the in vitro effect of side chain structure on the protein release kinetics of FITC-BSA with a 10% loading level.

The polymer P(CHDM-HOP) was blended with the protein FITC-BSA (bovine serum albumin, a protein, tagged with the fluorescent label FITC; "FITC-BSA") at a 2:1 (w/w) ratio (33% loading). Measured amounts (66 mg or 104 mg) of the polymer-protein blend were placed into 10 ml of PBS (0.1M, pH 7.4), a phosphate buffer. At regular intervals (roughly every day), the samples were centrifuged, the supernatant buffer was removed and subjected to absorption spectroscopy (501 nm), and fresh amounts of buffer were added to the samples. The resulting release curve, plotting the cumulative percentage of FITC-BSA released versus time, is graphically represented in FIG. 32. The loading level of the protein in both cases was 33 weight %.

Example 43

In Vitro Protein Release Profile At Various Loading Levels

FITC-BSA was blended with P) (CHDM-HOP) at different loading levels (1%, 10% and 30%) at room temperature until the mixture formed a homogenous paste. 60 mg of the protein-loaded polymer paste was placed in 6 mL of 0.1 M phosphate buffer and constantly shaken at 37° C. At various time points, samples were centrifuged, and the supernatant was replaced with fresh buffer. The released FITC-BSA in the supernatant was measured by UV spectrophotometry at 501 nm. FIG. 7 graphically represents the in vitro release kinetics of FITC-BSA as a function of loading level.

Example 44

Effect of Side Chain Structure on In Vitro Protein Release Kinetics of FITC-BSA

The following three polymers were prepared as described above:

P(CHDM-EOP)
P(CHDM-BOP) and
P(CHDM-HOP)

Figure 34:
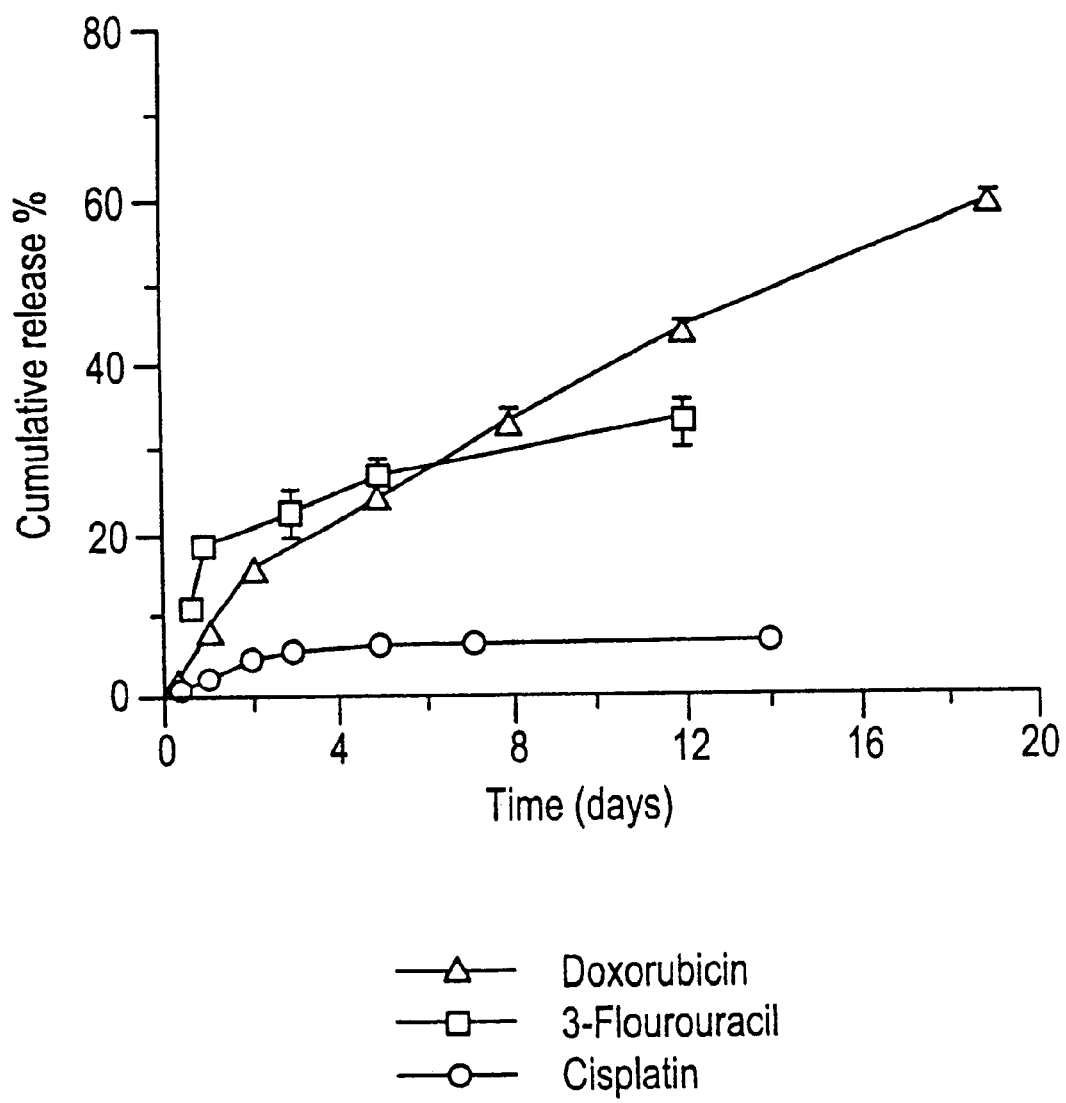
FIG. 34 shows the release of low molecular weight drugs (doxorubicin, cisplatin, and 5-fluorouracil) from P(CHDM-HOP).
Figure 35:
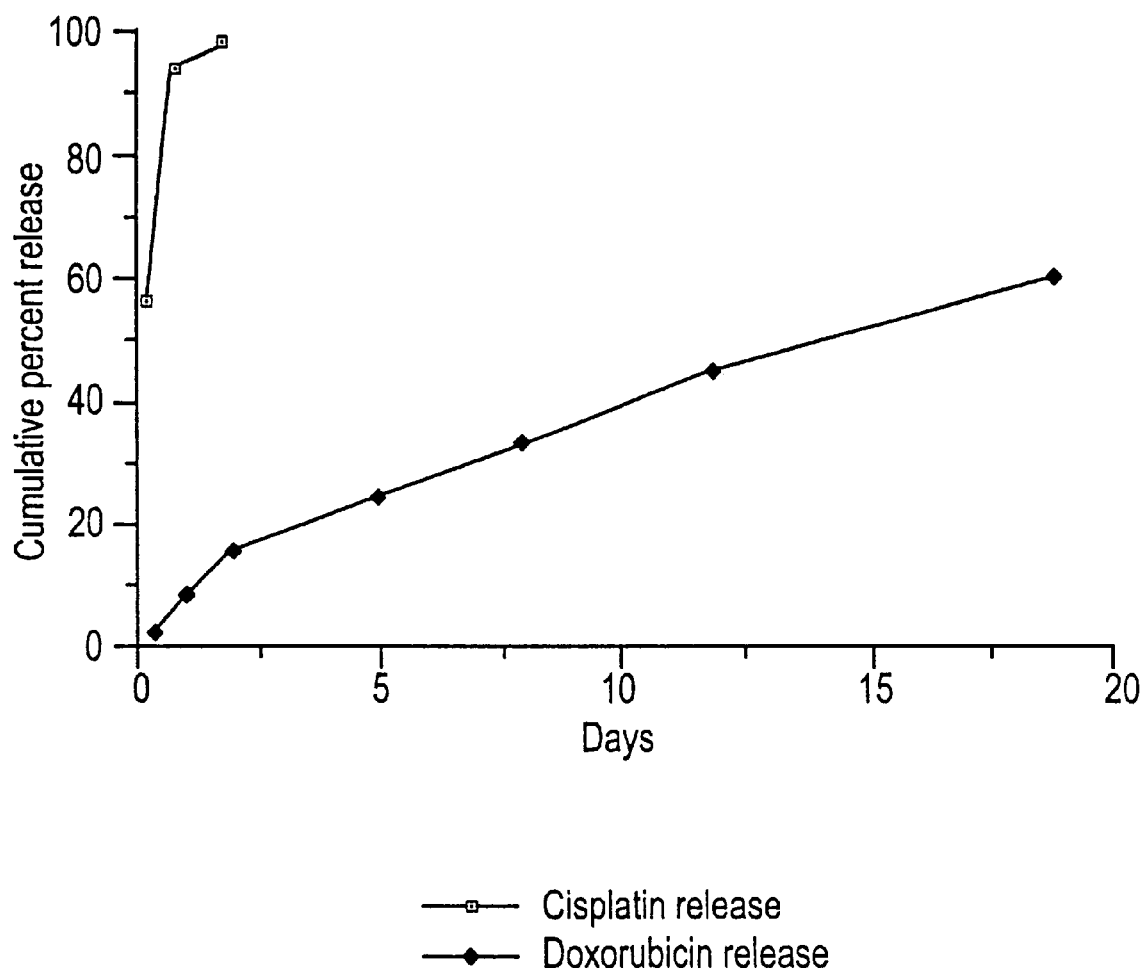
FIG. 35 shows the calibration curves for the release of IL-2 from a P(CHDM-HOP) matrix in tissue culture medium.

FITC-BSA was blended with each polymer at a 10% loading level at room temperature to form a homogenous paste. 60 mg of the protein-loaded polymer paste was placed in 6 mL of 0.1 M phosphate buffer with constant shaking at 37° C. At various time points, samples were centrifuged, and the supernatant was replaced with fresh buffer. The released FITC-BSA in the supernatant was measured by UV spectrophotometry at 501 nm. FIG. 34 graphically represents the in vitro effect of side chain variations on the protein release kinetics of FITC-BSA at 10% loading level.

Example 45

In Vitro Small Molecular Weight Drug Release from P(CHDM-HOP)

Figure 9A:
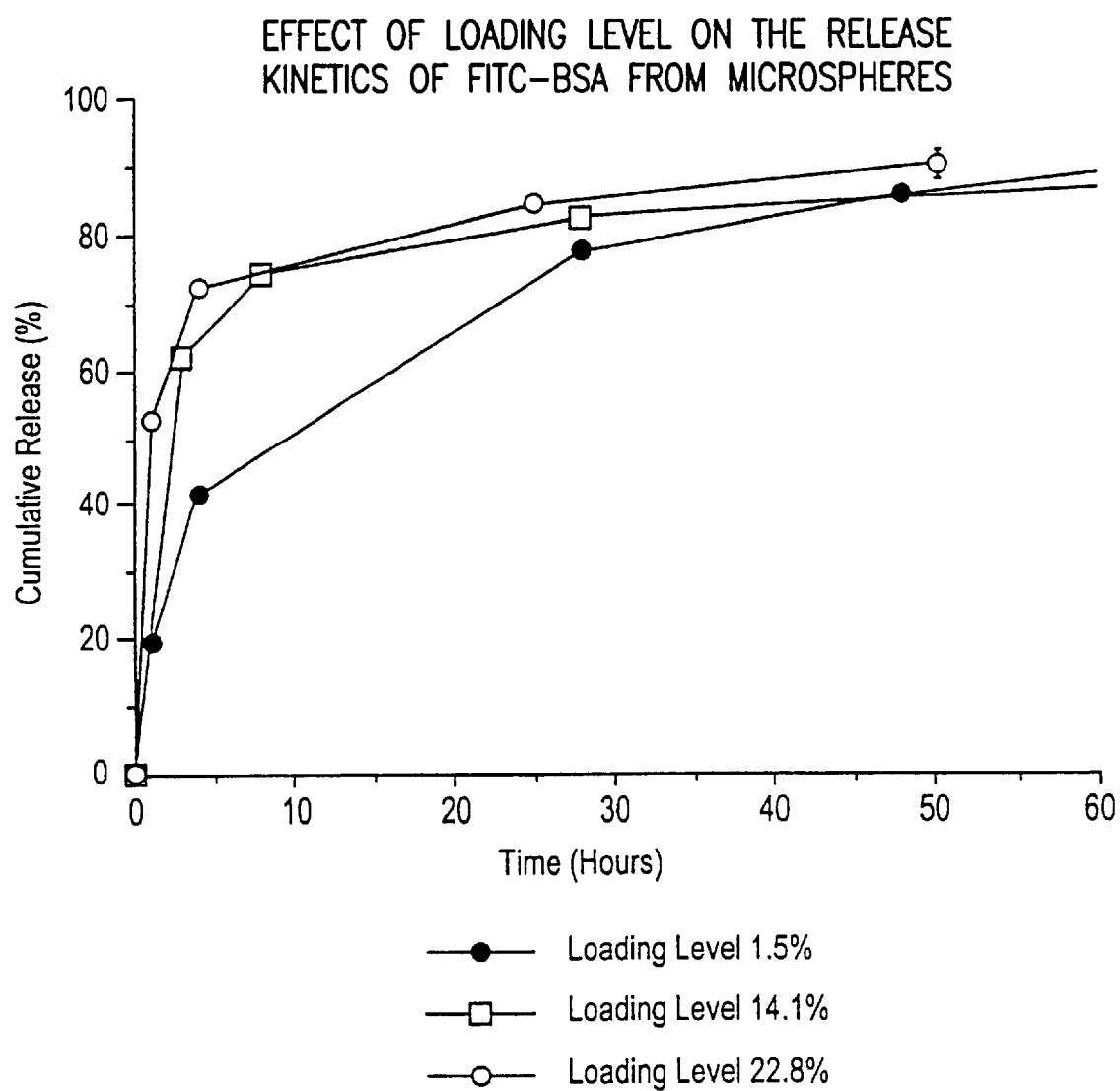
FIG. 9A shows the effect of loading level on the release kinetics of FITC-BSA from microspheres.

A P(CHDM-HOP) paste containing doxorubicin, cisplatin, or 5-fluorouracil, was prepared by blending 100 mg of P(CHDM-HOP) with 1 mg of the desired drug at room temperature, respectively. An aliquot of 60 mg of the drug-loaded paste was placed in 6 mL of 0.1 M phosphate buffer at 37° C. with constant shaking, with three samples being done for each drug being tested. At various time points, the supernatant was replaced with fresh buffer solution. The levels of doxorubicin and 5-fluorouracil in the supernatant were quantified by UV spectrophotometry at 484 nm and 280 nm, respectively. The cisplatin level was measured with an atomic absorbance spectrophotometer. FIG. 9A shows the release of these low molecular weight drugs from P(CHDM-HOP).

Figure 9B:
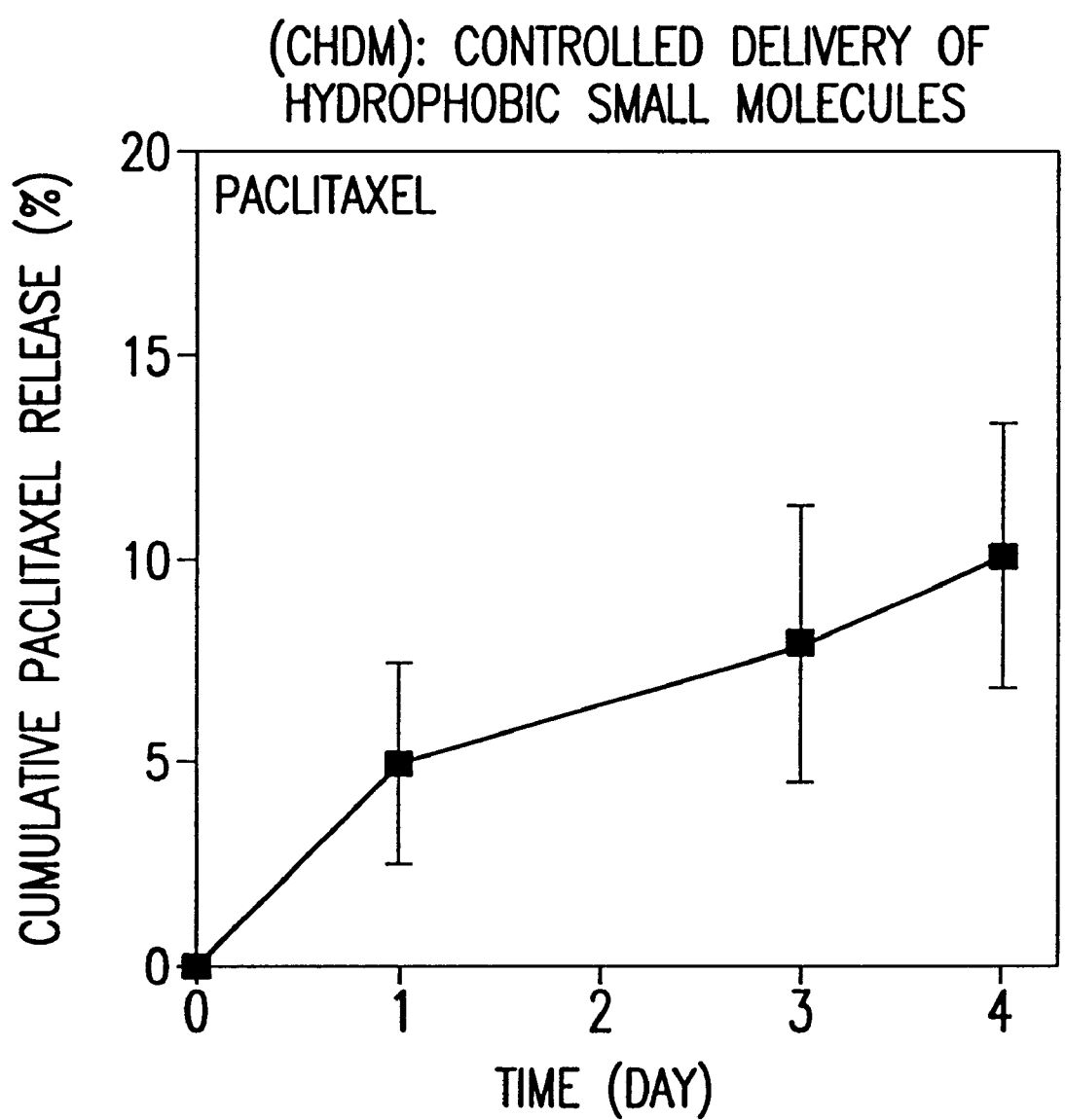
FIG. 9B shows the controlled delivery of hydrophobic small molecules, such as paclitaxel from a CHDM polymer.

FIG. 9B shows the release of hydrophobic small molecules, such as paclitaxel, from p(CHDM-HOP).

Example 46

In Vitro Release Profile of Doxorubicin and Cisplatin from P(CHDM-HOP)

Figure 36:
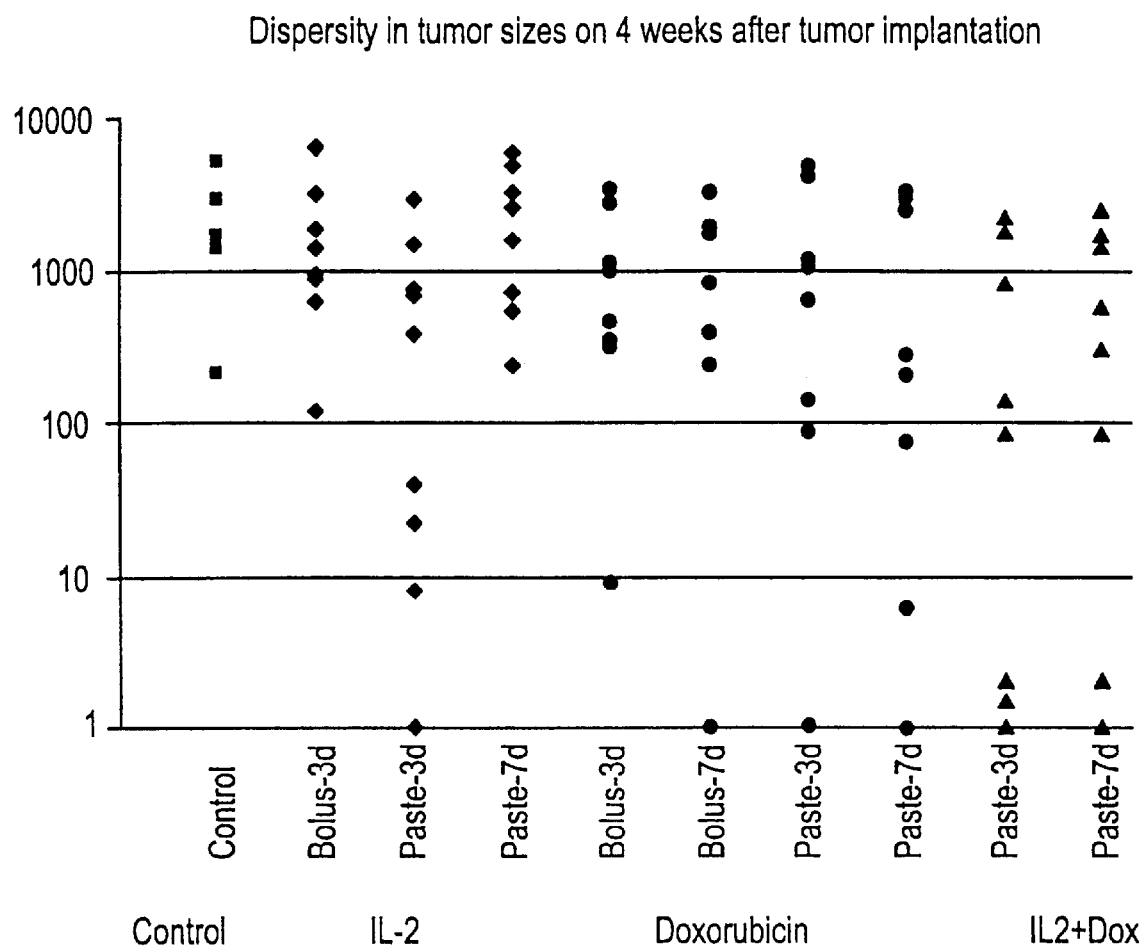
FIG. 36 shows the distribution of tumor sizes in mice four weeks after tumor implantation in an in vivo melanoma tumor model.

A paste was made by blending 300 mg of P(CHDM-HOP) with 6 mg of doxorubicin and 6 mg of cisplatin at room temperature to form a uniform dispersion. A sample of 100 mg of the paste was incubated in 10 mL of phosphate buffer (pH 7.4) at 37° C. with shaking. At different time points, samples were centrifuged, 9 mL of the supernatant were withdrawn and replaced with fresh buffer. The withdrawn supernatant was assayed spectrophotometrically at 484 nm to determine the amount of doxorubicin released into the withdrawn supernatant, and the cisplatin release was measured by atomic absorbance spectrophotometer. FIG. 36 graphically represents the simultaneous release of cisplatin and doxorubicin from P(CHDM-HOP).

Example 47

In Vivo Biocompatibility of P(trans-CHDM-HOP)

The polymer P(trans-CHDM-HOP) was synthesized as described in Example 1. To facilitate injection, ethyl alcohol was added to the polymer at levels of 10% and 20% by volume to reduce the viscosity. Samples of 25 µL of the polymer alone, 25 µL of the polymer containing 10% alcohol, and 25 µL of the polymer containing 20% alcohol, were injected into the back muscles of Sprague Dawley rats. Tissues at the injection sites were harvested at either three or thirteen days post-injection, processed for paraffin histology, stained with hematoxylin, eosin dye and analyzed. Medical-grade silicon oil was injected into the control group rats.

Histological examination of the back muscle sections of the rats injected with the polymer diluted with ethanol showed no acute inflammatory response. The level of macrophage presence was comparable to that of the control group, which had been injected with medical-grade silicon oil, and neutrophils were not present in any of the samples taken on either the third or thirteenth day.

Example 48

Controlled Delivery of Interleukin-2 and Doxorubicin from P(CHDM-HOP) in an In Vivo Tumor Model Lyophilized interleukin-2 ("IL-2") was purchased from Chiron, mouse Interferon-γ ("mIFN-γ") was obtained from Boehringer Mannheim, and doxorubicin hydrochloride ("DOX") was obtained from Sigma. C57BL/6 mice, 6–8 weeks of age, were obtained from Charles River. The aggressive melanoma cell line B16/F10 was used to cause tumors in the mice, and the cells were maintained by weekly passages. The polymer P(CHDM-HOP) was synthesized as described in Example 35.

Mice were randomly allocated into groups as shown below in Table 12. The day of tumor injection with cells of the melanoma cell line was denoted as Day 0. Each mouse received a subcutaneous injection of 50 µl ($10^5$) tumor cells in phosphate buffer saline (PBS) in the left flank. On Day 3 or Day 7, the tumor-bearing mice were selectively injected in the right flank with one of the following formulations: (1) a bolus of IL-2, (2) a bolus of DOX, (3) a polymer paste of IL-2, (4) a polymer paste of DOX, (5) a polymer paste containing both IL-2 and DOX, or (6) a polymer paste containing both IL-2 and mIFN-γ). A control group and negative control group received no further injections on Day 3 or Day 7.

The bolus preparation of either IL-2 or DOX was prepared by dissolving an appropriate amount of IL-2 or DOX in 50 µl of isotonic solution just prior to the injection. The polymer paste formulations of either IL-2, DOX, a mixture of both IL-2 and DOX, or a mixture of IL-2 and mIFN-γ, were prepared by blending 50 µl of sterilized P(CHDM-HOP) with the drug(s) until homogeneous.

TABLE 12

Allocation of Groups of Mice for In Vivo Tumor Model

| Group | Number of Mice | Day of Injection | Formulation |
| --- | --- | --- | --- |
| Control | 5 | — | Nothing |
| Negative Control | 5 | — | Nothing |
| Bolus IL-2 | 8 | 3 | $0.8 \times 10^6$ IU |
| Bolus DOX | 8 | 3 | 0.5 mg |
| Bolus DOX | 8 | 7 | 0.5 mg |
| Paste IL-2 | 10 | 3 | $0.8 \times 10^6$ IU |
| Paste IL-2 | 10 | 7 | $0.8 \times 10^6$ IU |
| Paste DOX | 10 | 3 | 0.5 mg |
| Paste DOX | 10 | 7 | 0.5 mg |
| Paste (IL-2 + DOX) | 10 | 3 | $0.8 \times 10^6$ IU + 0.5 mg |
| Paste (IL-2 + DOX) | 10 | 7 | $0.8 \times 10^6$ IU + 0.5 mg |
| Paste (IL-2 + mIFN-γ) | 10 | 3 | $10^6$ IU |

On Day 28 and Day 42 of tumor growth, the tumor sizes of the various mice were measured. The results are shown below in Table 13, which shows the numerical data for the growth of tumor volumes on Day 28 and Day 42 and the number of mice who survived the experiment per drug grouping. Tumor volume was calculated as half the product of the length and the square of the width, in accordance with the procedure of Osieka et al., 1981.

TABLE 13

CHDM-HOP Polymer as Carrier for Cytokine and Drug Delivery in Melanoma Model

| Group | Initial Number of Mice | Tumor Volume (mm³ ± SEM*) After Tumor Injection | |
|---|---|---|---|
| | | 28 days | 42 days |
| | | Number of Mice Survived | |
| Control | 5 | No tumor | No tumor |
| Negative Control | 5 | 2458 ± 1070.7<br>4 | 5656<br>1 |
| Bolus IL-2 (3d) | 8 | 1946 ± 505.6<br>8 | 3282 ± 1403.3<br>4 |
| Bolus Dox (3d) | 8 | 1218.9 ± 304.1<br>8 | 3942.5 ± 1818<br>5 |
| Bolus Dox (7d) | 8 | 1661.2 ± 301.8<br>8 | 4394.3 ± 741.3<br>3 |
| Paste IL-2 (3d) | 10 | 934.1 ± 230<br>10 | 3183 ± 1223.4<br>5 |
| Paste IL-2 (7d) | 10 | 2709.8 ± 397.3<br>10 | 10491 ± 2485.5<br>3 |
| Paste Dox (3d) | 10 | 1410 ± 475.3<br>8 | 4648.9 ± 1202.2<br>7 |
| Paste Dox (7d) | 10 | 1480 ± 287<br>9 | 3915 ± 1739.7<br>4 |
| Paste (IL-2 + DOX) (3d) | 10 | 657.3 ± 248.9<br>8 | 3362.8 ± 1120.1<br>7 |
| Paste (IL-2 + DOX) (7d) | 10 | 857.2 ± 243.6<br>8 | 3449.8 ± 1285.9<br>5 |
| Paste (IL-2 + mIFN-γ) (3d) | 10 | 1217.9 ± 168.4<br>9 | 4469.8 ± 2018.7<br>4 |

*Standard Error of the Mean

Figure 37:
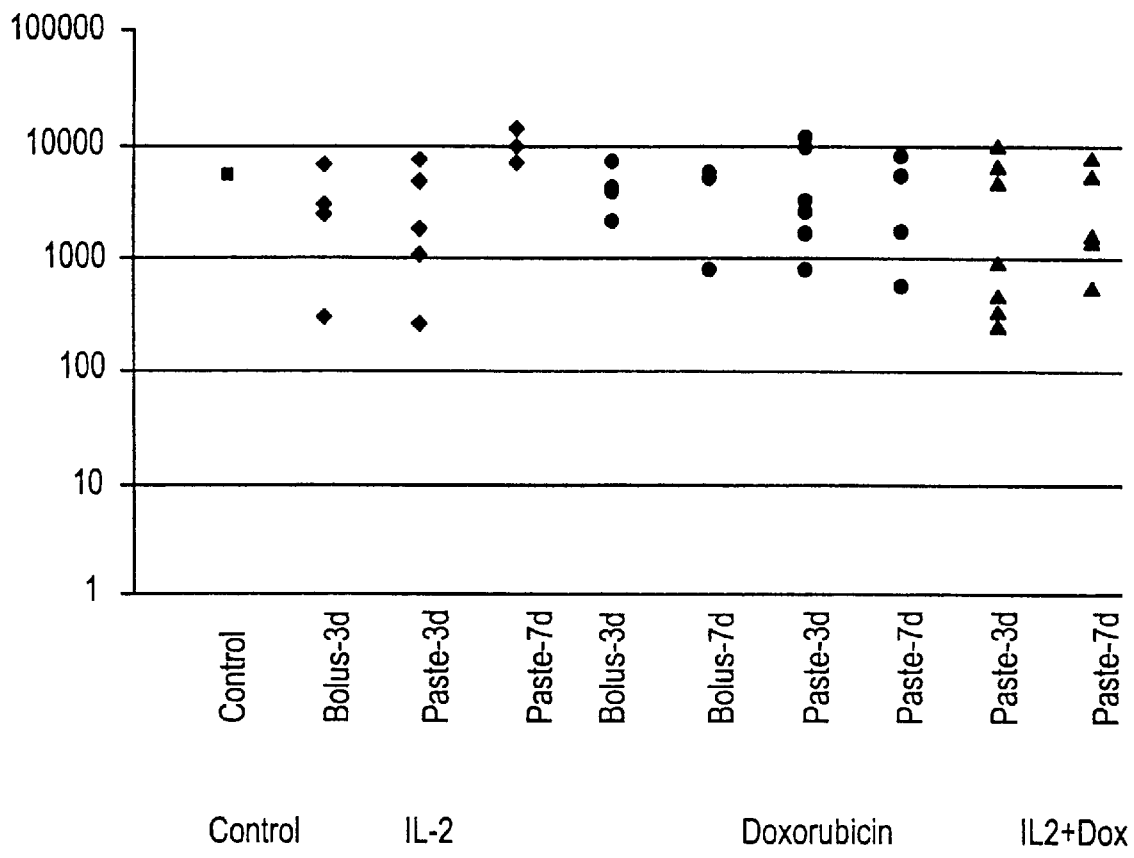
FIG. 37 shows the distribution of tumor sizes in mice six weeks after tumor implantation in an in vivo melanoma tumor model.
Figure 38:
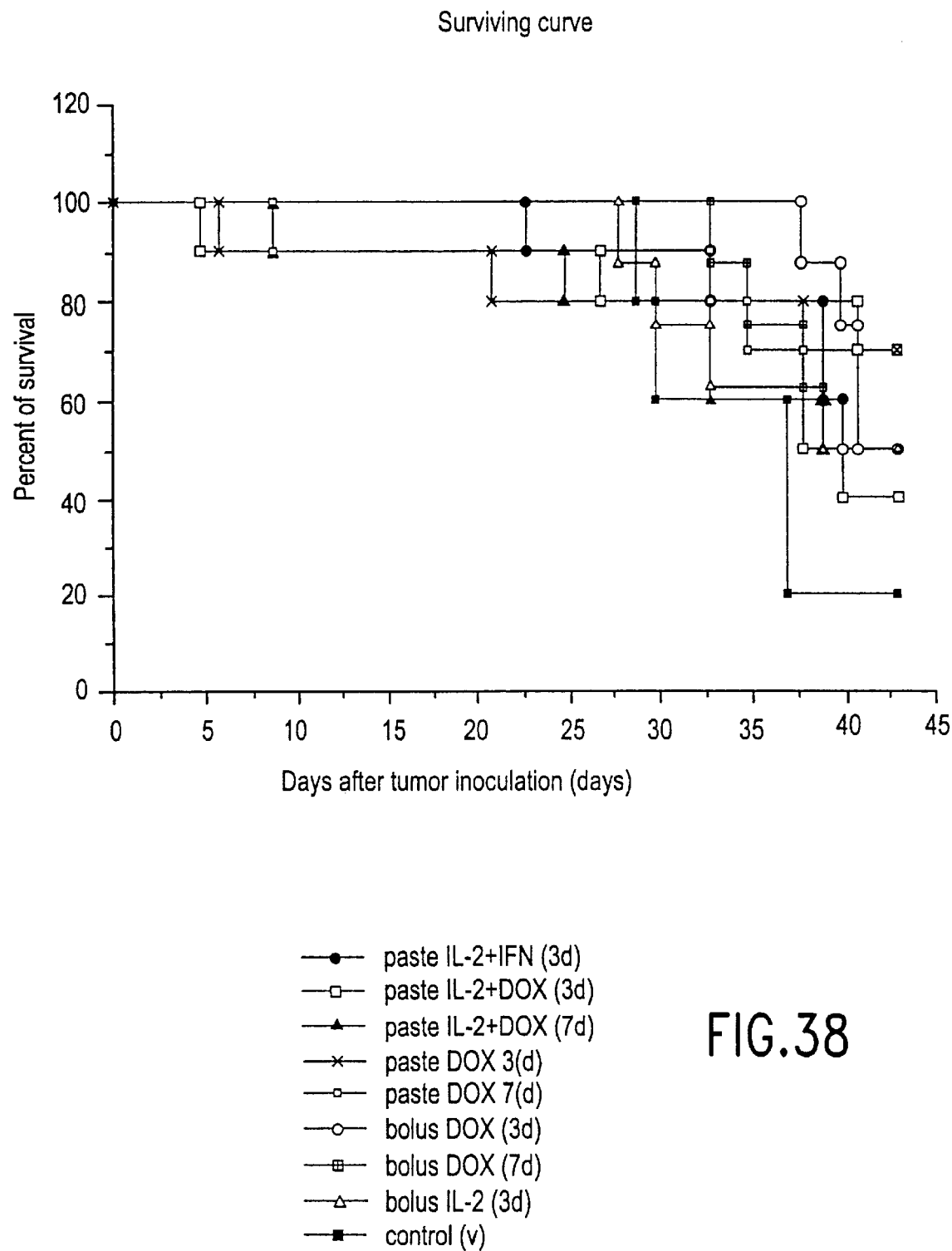
FIG. 38 shows the percentage of survival as a function of time for four different treatment groups in an in vivo melanoma tumor model.

Based on these measurements, the distribution of tumors sizes were graphically represented in FIG. 37 for Day 28 (four weeks after tumor implantation) and in FIG. 38 for Day 42 (six weeks after tumor implantation). The graphs were subdivided into plots according to the different treatments given to the tumor-bearing mice.

The results on Day 28 showed that, in comparison with the control group (tumor without treatment) and the bolus injection of IL-2, the group of mice receiving a polymer/IL-2 paste injection successfully delayed the tumor's growth. However, for the group of mice not receiving a polymer/IL-2 paste injection until Day 7, the tumor had already become of substantial size by Day 7 and, accordingly, a significant reduction in tumor size was not observed.

Excellent tumor reduction was obtained with the combination of IL-2 and DOX. The average size of a tumor treated with an injection of a polymer paste containing both IL-2 and DOX was significantly smaller than the tumor in the control group. Specifically, the average tumor size for mice receiving the IL-2 and DOX/polymer paste on Day 3 was 657.3 mm³, as opposed to 2458 mm³ for the control group. Even when treatment was delayed until Day 7 of tumor growth, a therapeutic effect could still be seen with the polymer paste formulation containing both IL-2 and DOX.

Figure 15:
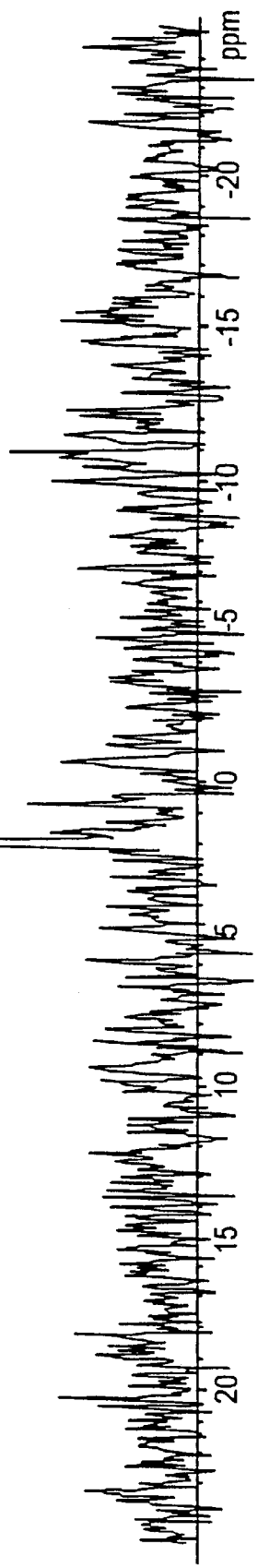
FIG. 15 shows the $^{31}$P-NMR spectrum of a polymer of the invention, P(LAEG-EOP).

The results on Day 42 of tumor growth also confirmed that the Day 3 injection of polymer paste containing both IL-2 and DOX gave the best result in delaying tumor growth. The combined therapy of IL-2 and DOX in a polymer paste of the invention resulted in the occurrence of smaller sized tumors in more of the test animals. According to the distribution data shown in FIG. 15, there were four mice bearing tumors of less than 1000 mm³ in the case of the combined IL-2 and DOX polymer paste therapy, as compared with only one mouse inside that range for the polymer paste injection of DOX alone. It was also clear that IL-2 alone did not provide the most desirable effect, as evaluated on the 42nd day of tumor growth. Despite the good distribution of small tumor sizes on the 28th day, the long-time survival data appeared to be adversely affected, not only by the progression of tumor growth at that point, but also by the lack of continued, controlled delivery of IL-2 over a longer time period. With the polymer paste formulation of both IL-2 and DOX, the polymer degraded slowly, allowing a gradual decrease in the diffusion rate of the therapeutic agent over time.

Figure 39:
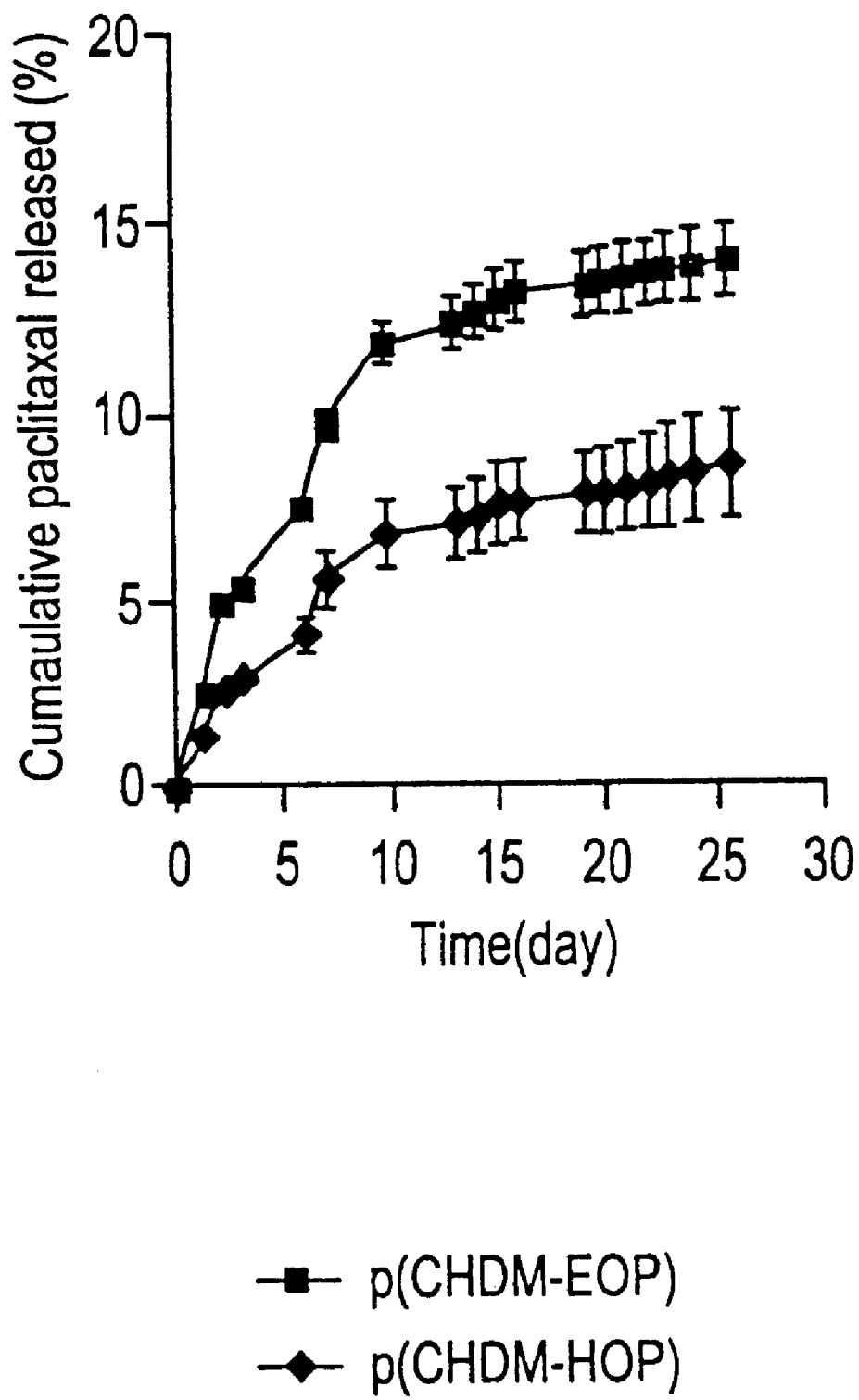
FIG. 39 shows the release curves of two polymer compositions of the invention, one comprising the chemotherapeutic agent paclitaxel in the polymer P(CHDM-EOP) and the other comprising paclitaxel in the polymer P(CHDM-HOP).
Figure 40:
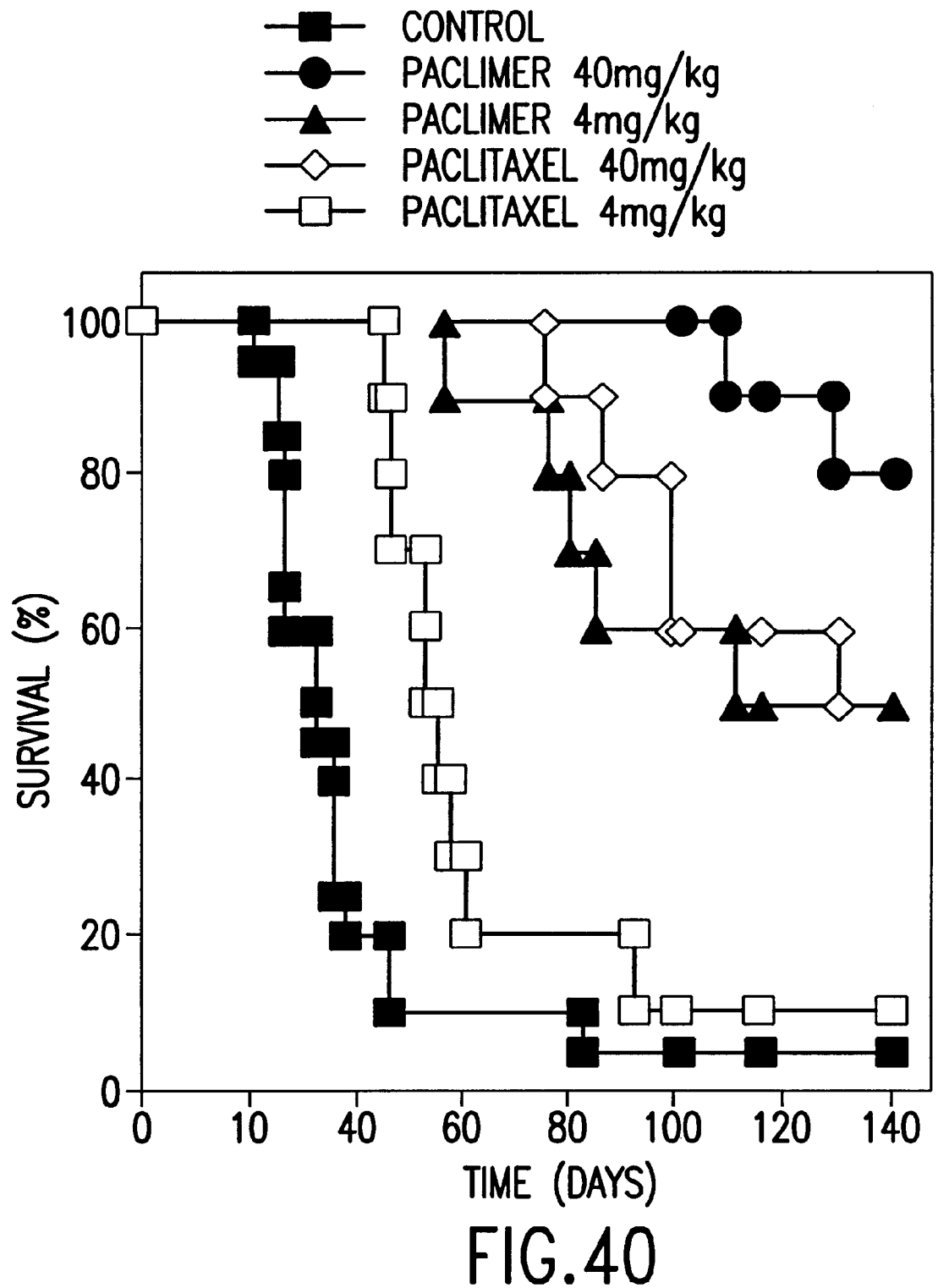
FIG. 40 shows the efficacy of paclitaxel in a solvent and paclitaxel in a p(DAPG-EOP) polymer in an ovarian cancer animal model (OVCAR3).

However, because of the significant difference of the distribution in tumor sizes inside each group, the average tumor size as seen in Table 13 did not provide a complete picture. A fuller appreciation of the significance of the treatments of the invention can be gained by comparing data from the distribution graph of FIG. 38 which shows the dispersity in tumor sizes six weeks after tumor implantation, with the survival curve shown in FIG. 39, which shows the massive death of mice in all groups before the Day 42 measurement, except for the groups of animals that had received the 3rd day injection of paste containing either DOX alone or the combination of IL-2 and DOX. Thus, the data, taken as a whole, shows that the combined therapy of IL-2 and DOX in the paste both significantly delayed tumor growth and extended life.

Early deaths about 3–4 days after the injections of the DOX-containing polymer paste were thought to be due, at least in part, to the toxic effect of DOX causing the deaths of the weaker animals. Corresponding injections of bolus DOX did not produce early death, probably because of the rapid distribution and clearance from the body of the bolus-injected DOX.

Example 49

Incorporating Paclitaxel into P(CHDM-HOP) or P(CHDM-EOP)

100 mg of each of the polymers p(CHDM-HOP) and p(CHDM-EOP) was dissolved in ethanol at a concentration of about 50%. After the polymer was completely dissolved, 5 mg of paclitaxel powder (a chemotherapeutic drug) was added to the solution and stirred until the powder was completely dissolved. This solution was then poured into ice water to precipitate the polymer composition. The resulting suspension was centrifuged, decanted, and lyophilized overnight, to obtain a viscous gelatinous product.

Example 50

In Vitro Release of Paclitaxel from P(CHDM-HOP) and P(CHDM-EOP)

In a 1.7 mL plastic micro centrifuge tube, 5 mg of both of the paclitaxel polymer formulations of Example 20 to be tested was incubated with 1 mL of a buffer mixture of 80% PBS and 20% PEG 400 at 37° C. Four samples of each formulation to be tested were prepared. At specific time points, approximately every day, the PBS:PEG buffer was poured off for paclitaxel analysis by HPLC, and fresh buffer was added to the microcentrifuge tube. The release study was terminated at day 26, at which point the remaining paclitaxel in the polymer was extracted with a solvent to do a mass balance on paclitaxel.

The resulting release curves for the release of paclitaxel from both polymers are shown in FIG. 18. The total paclitaxel recovery was 65% for the P(CHDM-HOP) formulation and 75% for the P(CHDM-EOP) formulation.

Example 51

In Vitro Release of Paclitaxel from P(DAPG-EOP)

P(DAPG-EOP) microspheres were prepared by a solvent evaporation method, using ethyl acetate as the solvent and 0.5% PVA in water as a non-solvent. The resulting microspheres are spherical in shape with particle sizes ranging from about 20–150 µm, most preferably 20–50 µm.

Figure 41:
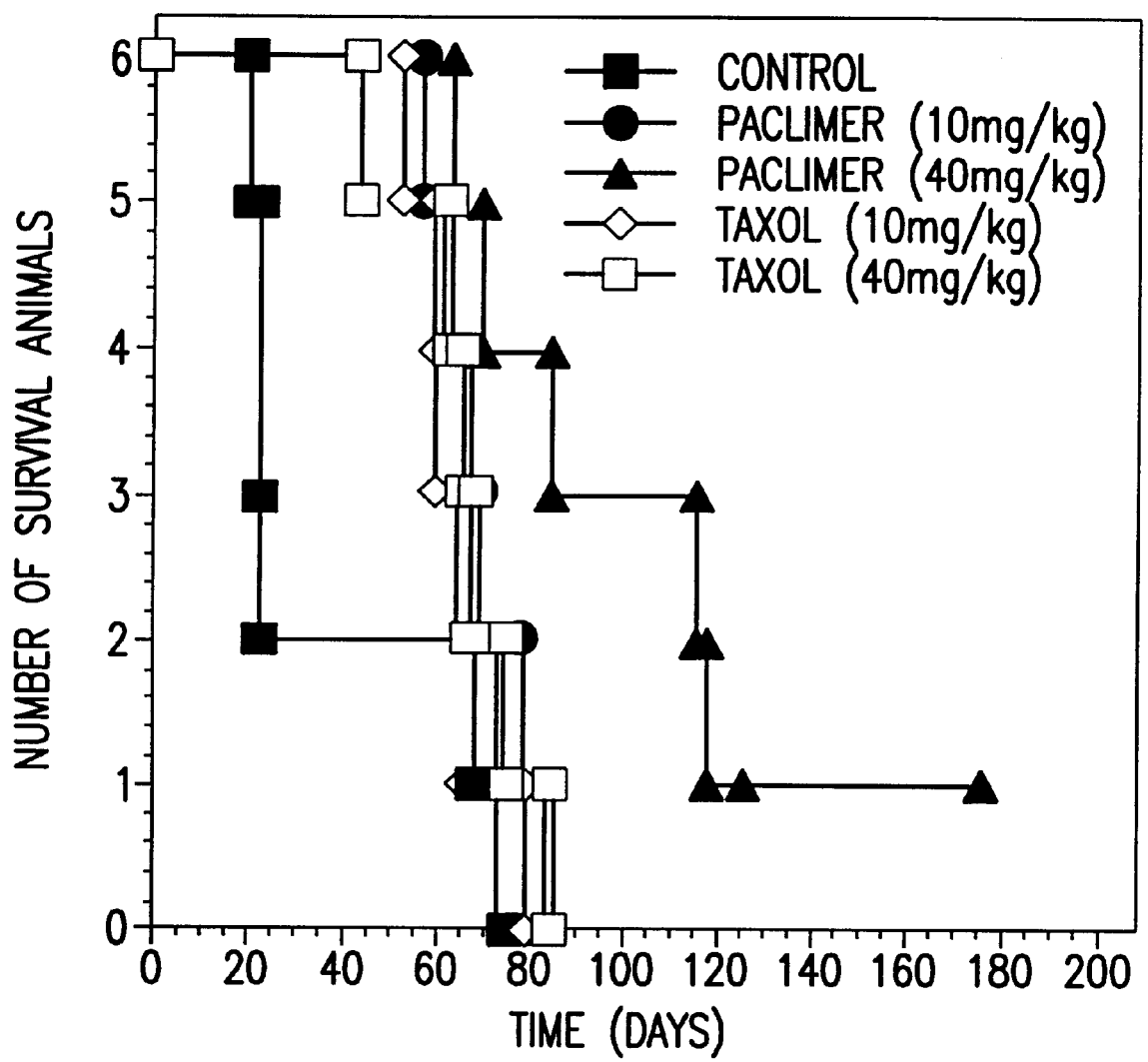
FIG. 41 shows the efficacy of p(DAPG-EOP) containing paclitaxel in an OVCAR3 ovarian cancer animal model.

The in vitro release of paclitaxel from the microspheres was carried out in PBS (pH 7.4) at 37° C. To maintain a sink condition, an octanol layer was placed on top of the PBS to continuously extract the released paclitaxel. The released paclitaxel was quantified using an HPLC method, and the in vitro mass loss of the polymer was obtained by a gravimetric method. The in vitro release of paclitaxel from the microspheres was slow and continuous with concomitant polymer mass loss, as shown in FIG. 41.

Example 52

In Vivo Release of Paclitaxel from P(DAPG-EOP)

P(DAPG-EOP) microspheres were prepared as described above in Example 52, and the In vivo release of paclitaxel from the microspheres was studied on nude mice. Plasma was collected from each of the test animals at 1, 14 and 28 days after injection, and paclitaxel concentration was analyzed by HPLC with MS-MS detection. For efficacy studies, test animals received intraperitoneal injections of a human ovarian cancer cell line OVCAR3 obtained from carrier animals. P(DAPG-EOP) microspheres incorporating paclitaxel or paclitaxel without the biodegradable polymer were also given intraperitoneally at one day post cell injection. The survival of the animals was also monitored.

Following a single intraperitoneal administration of the microspheres, a sustained level of paclitaxel in plasma was obtained for at least 28 days, as shown below in Table 14:

TABLE 14

Paclitaxel Plasma Concentration

| | Paclitaxel Concentration (ng/ml) | |
|---|---|---|
| | Paclitaxel in Microspheres (125 mg/kg) | Paclitaxel w/o polymer (120 mg/kg) |
| 1 day | 38.98 ± 7.53 | 357.67 ± 136.39 |
| 14 days | 4.50 ± 1.21 | Animal died |
| 28 days | 3.98 ± 0.99 | Animal died |

When a comparable dose of paclitaxel was given intraperitoneally, the nude mice could not tolerate the dose due to the toxicity.

Figure 42:
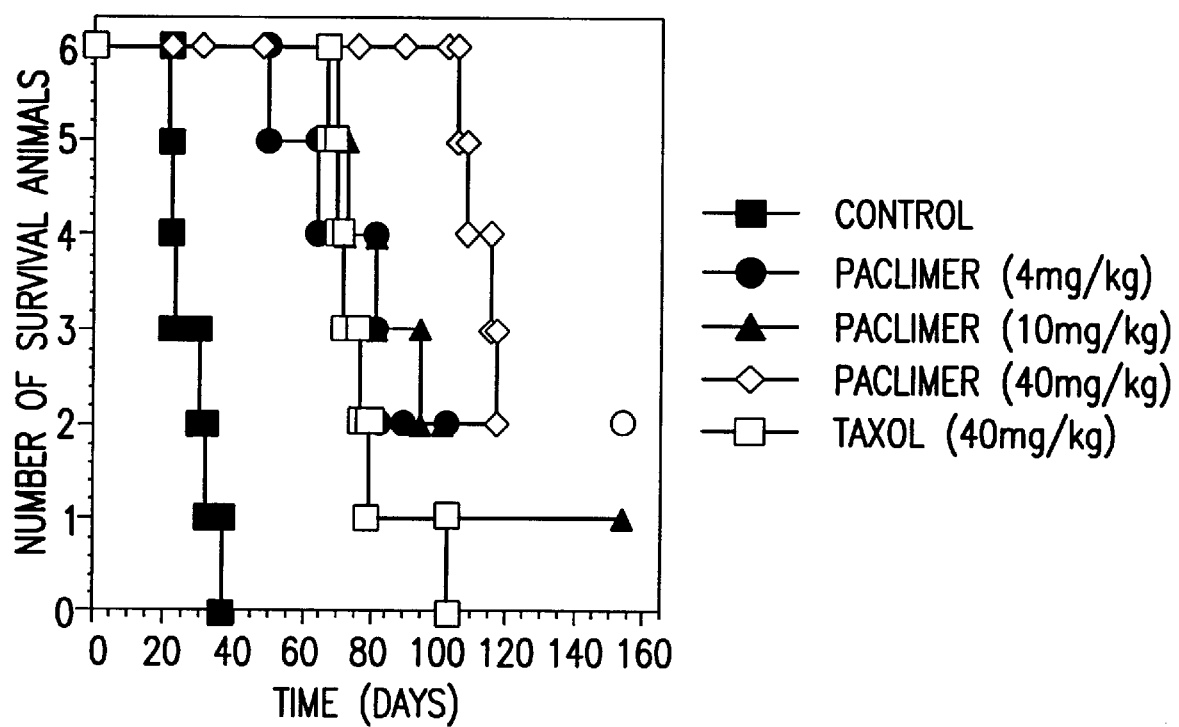
FIG. 42 shows the efficacy of p(DAPG-EOP) containing paclitaxel in an OVCAR3 ovarian cancer animal model.

The biodegradable polymer microsphere delivery system was surprisingly effective in treating ovarian cancer in the animal model OVCAR3. As shown in FIG. 42, superior efficacy was obtained, as compared with paclitaxel without the biodegradable polymer.

Example 53

Median Survival Data for P(DAPG-EOP) Paclitaxel

P(DAPG-EOP) microspheres containing 10 mg/kg or 40 mg/kg paclitaxel were injected into the peritoneums of test animals having ovarian cancer. Other test animals were injected with paclitaxel in an organic solvent, commercially available under the trade name Taxol, at the same dosage levels. The test animals were monitored, and median survival times were noted. The results are summarized below:

| Material Administered | Median Survival |
|---|---|
| Control | 23 days |
| Taxol, 10 mg/kg | 64 days |
| Taxol, 40 mg/kg | 67 days |
| Paclitaxel in microspheres, 40 mg/kg | 69 days |
| Paclitaxel in microspheres, 40 mg/kg | 115 days |

Figure 43:
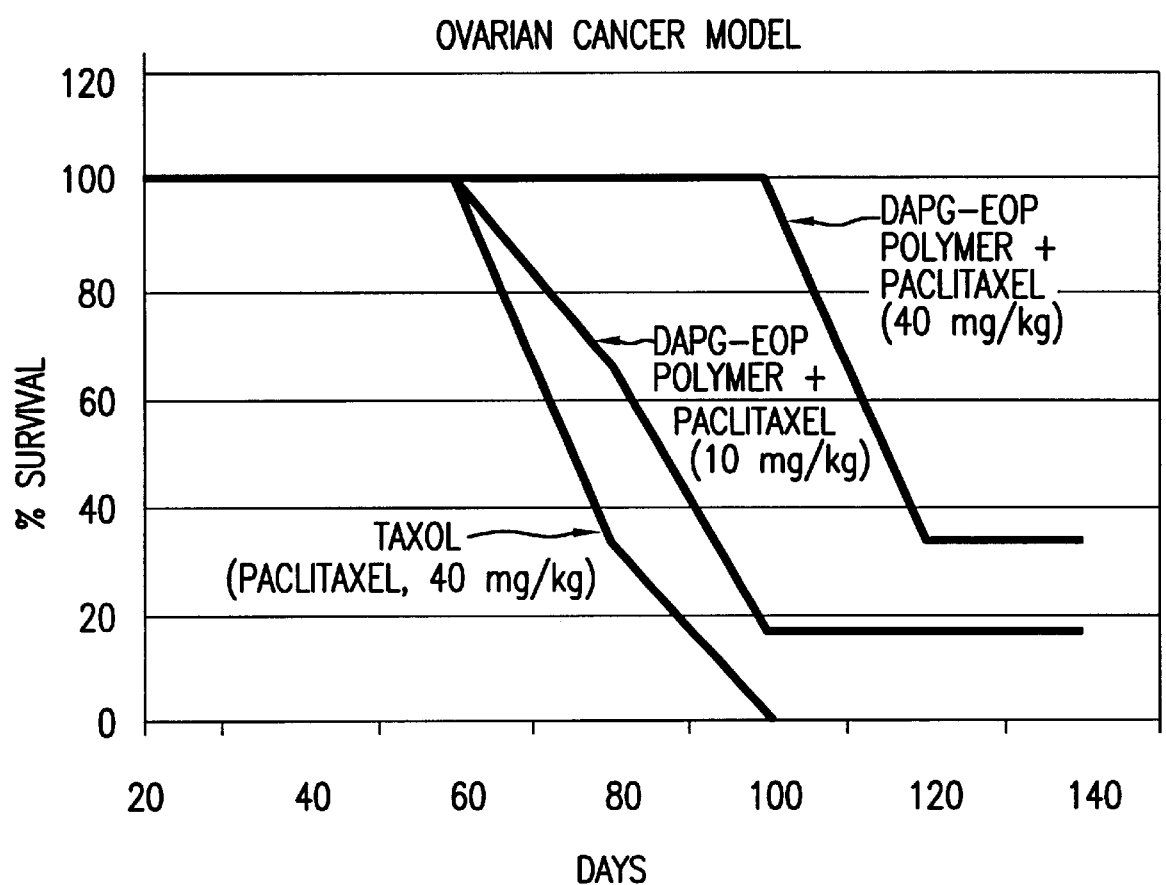
FIG. 43 shows further efficacy data for p(DAPG-EOP) containing paclitaxel in an OVCAR3 ovarian cancer animal model.

These results are represented graphically in FIG. 43 and indicate an unexpectedly large increase in median survival for the test animals given the paclitaxel in the form of biodegradable microspheres.

A comparison of a different set of dosage levels gave the following similar data:

| Material Administered | Median Survival |
|---|---|
| Control | 30 days |
| Taxol, 40 mg/kg | 77 days |
| Paclitaxel in microspheres, 4 mg/kg | 83 days |
| Paclitaxel in microspheres, 10 mg/kg | 95 days |
| Paclitaxel in microspheres, 40 mg/kg | >110 days |

Figure 44:
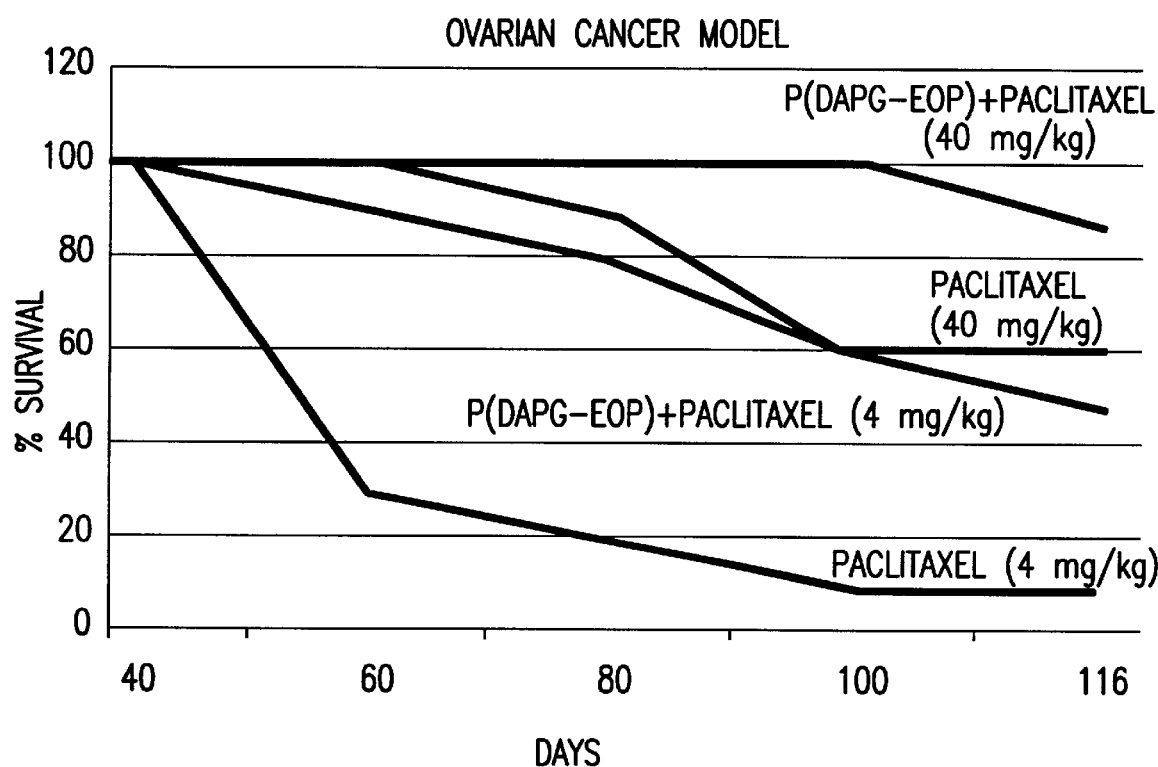
FIG. 44 shows still further efficacy data for p(DAPG-EOP) containing paclitaxel in an OVCAR3 ovarian cancer animal model.

These results are represented graphically in FIG. 44 and confirm the unexpectedly large increase in median survival for the test animals given the paclitaxel in the form of biodegradable microspheres. Additional graphical representations of this data are provided by FIGS. 45 and 46.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A biodegradable polymer composition suitable for intraperitoneal administration to treat a mammalian subject having ovarian cancer, said composition comprising:

(a) at least one antineoplastic agent and (b) a biodegradable polymer comprising the recurring monomeric units shown in formula III $$\left[ \left( X \diagdown_{M^1} \diagup^O_C \right)_x Y \diagdown_L \diagup Y \left( \diagdown^O_C \diagup_{M^1} \diagdown X \right)_y \overset{R_3}{\underset{\overset{\|}{O}}{P}} \right]_n \quad \text{III}$$

wherein

X is —O— or —NR$^4$—, where R$^4$ is H or alkyl;

Y is —O—, —S— or —NR$^4$—;

M$^1$ is (1) a branched or straight chain aliphatic group having from 1–20 carbon atoms; or (2) a branched or straight chain, oxy-, carboxy- or amino-aliphatic group having from 1–20 carbon atoms;

L is a divalent, branched or straight chain aliphatic group having 1–20 carbon atom;

$R^3$ is selected from the group consisting of H, alkyl, alkoxy, aryl, aryloxy, heterocyclic or heterocycloxy;

the molar ratio of x:y is about 1;

the molar ratio n:(x or y) is between about 200:1 and 1:200; and n is about 5–5,000;

wherein said polymer composition provides extended release of said antineoplastic agent into the peritoneum of said subject; and wherein said composition increases the median survival rate from said cancer by at least about 10%, as compared with the median survival rate obtained by administration of a composition comprising the same dosage of said antineoplastic agent without said biodegradable polymer.

2. The composition of claim 1, wherein said polymer composition increases the median survival rate from said cancer by at least about 20%, as compared with the median survival rate obtained by administration of a composition comprising the same dosage of said antineoplastic agent without said biodegradable polymer.

3. The polymer composition of claim 1, wherein said composition increases the median survival rate from said cancer by at least about 30%, as compared with the median survival rate obtained by administration of a composition comprising the same dosage of said antineoplastic agent without said biodegradable polymer.

4. The polymer composition of claim 1 wherein a single dose of said polymer composition provides extended release of said antineoplastic agent over a time of at least 28 days.

5. The composition of claim 1 wherein each of $M^1$ and L is a branched or straight chain alkylene group.

6. The composition of claim 1 wherein each of $M^1$ and L has from 1 to 7 carbon atoms.

7. The composition of claim 1 wherein $M^1$ is an ethylene group or a methyl-substituted methylene group, and L is an ethylene group.

8. The composition of claim 1 wherein $R^3$ is an alkyl group, an alkoxy group, a phenyl group, a phenoxy group, or a heterocycloxy group.

9. The composition of claim 1 wherein $R^3$ is an alkoxy group having from 1 to 7 carbon atoms.

10. The composition of claim 1 wherein $R^3$ is an ethoxy group.

11. The composition of claim 1 wherein $M^1$ is a branched or straight chain alkylene group.

12. The composition of claim 1 wherein $M^1$ is an alkylene or alkoxylene group having a formula selected from the group consisting of —$(CH_2)_a$—, —$(CH_2)_a$—O—, and —$(CH_2)_a$—O—$(CH_2)_b$—, wherein each of a and b an integer from 1 to 7.

13. The composition of claim 1 wherein $M^1$ has the formula: —CHR'—CO—O—CHR"—, wherein R' and R" are each independently H, alkyl, alkoxy, aryl, aryloxy, heterocyclic or heterocycloxy.

14. The composition of claim 1 wherein $M^1$ has from 1 to 7 carbon atoms.

15. The composition of claim 1 wherein X is —O—.

16. The composition of claim 1 wherein X is —$NR^4$—.

17. The composition of claim 1 wherein:

$M^1$ and $M^2$ are each an alkylene or alkoxylene group;

L is an alkylene group;

X is —O—; and $R^3$ is an alkoxy group.

18. The composition of claim 1 wherein the molar ratio x:y is about 1.

19. The composition of claim 1 wherein each of x and y is about 1 to 1,000.

20. The composition of claim 1 wherein the molar ratio n:(x or y) is between about 100:1 and 1:100.

21. The composition of claim 1, wherein said polymer is prepared by solution polymerization.

22. The composition of claim 1, wherein said polymer is prepared by melt polymerization.

23. The composition of claim 1, wherein said polymer comprises additional biocompatible monomeric units or is blended with other biocompatible polymers.

24. The composition of claim 1, wherein said polymer is soluble in at least one of the solvents selected from the group consisting of acetone, dimethylene chloride, chloroform, ethyl acetate, DMAC, N-methyl pyrrolidone, dimethylformamide and dimethylsulfoxide.

25. The composition of claim 1, wherein said antineoplastic agent comprises paclitaxel.

26. The composition of claim 1, wherein the molecular weight (Mw) of said polymer is from about 2,000 to 400,000 daltons.

27. The composition of claim 1, wherein said antineoplastic agent and said polymer form an amorphous, monolithic matrix.

28. The composition of claim 1, in the form of microparticles, a flexible film, a viscous liquid, wafers or rods.

29. The composition of claim 1, in the form of spray-dried microspheres.

30. A solid article comprising a biodegradable polymer composition comprising:

(a) at least one antineoplastic agent and (b) a biodegradable polymer comprising the recurring monomeric units shown in Formula III:

wherein

X is —O— or —$NR^4$—, where $R^4$ is H or alkyl;

Y is —O—, —S— or —$NR^4$—;

each of $R^1$ and $R^2$ is a divalent organic moiety;

L is a divalent, branched or straight chain aliphatic group having 1–20 carbon atom, a cycloaliphatic group, or a group having the formula:

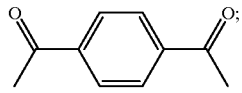

$R^3$ is selected from the group consisting of H, alkyl, alkoxy, aryl, aryloxy, heterocyclic or heterocycloxy; and n is about 5–5000;

$M^1$ is (1) a branched or straight chain aliphatic group having from 1–20 carbon atoms; or (2) a branched or straight chain oxy-, carboxy- or amino-aliphatic group having from 1–20 carbon atoms;

the molar ratio of x:y is about 1; and the molar ratio of n:(x or y) is between about 200:1 and 1:200;

wherein the article is suitable for insertion into a mammal, and wherein the article is in at least partial contact with an ovarian cancer tumor or the tissue surrounding the site of an ovarian cancer tumor.

31. A solid article suitable for insertion into the peritoneum to treat a mammalian subject having ovarian cancer, said article comprising a biodegradable polymer composition suitable for intraperitoneal administration to treat a mammalian subject having ovarian cancer, said composition comprising:

(a) at least one antineoplastic agent and
(b) a biodegradable polymer comprising the recurring monomeric units shown in formula III:

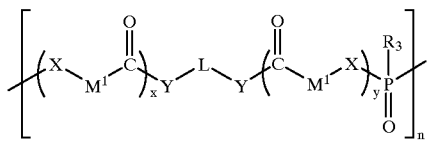

wherein
X is —O— or —NR$^4$—, where R$^4$ is H or alkyl;
Y is —O—, —S— or —NR$^4$—;
M$^1$ is (1) a branched or straight chain aliphatic group having from 1–20 carbon atoms; or (2) a branched or straight chain, oxy-, carboxy- or amino-aliphatic group having from 1–20 carbon atoms;
L is a divalent, branched or straight chain aliphatic group having 1–20 carbon atom;
R$^3$ is selected from the group consisting of H, alkyl, alkoxy, aryl, aryloxy, heterocyclic or heterocycloxy;
the molar ratio of x:y is about 1;
the molar ratio n:(x or y) is between about 200:1 and 1:200; and
n is about 5–5,000;
wherein said polymer composition provides extended release of said antineoplastic agent into the peritoneum of said subject; and
wherein said composition increases the median survival rate from said cancer by at least about 10%, as compared with the median survival rate obtained by administration of a composition comprising the same dosage of said antineoplastic agent without said biodegradable polymer.

32. The article of claim 31, wherein said composition increases the median survival rate from said cancer by at least about 20%, as compared with the median survival rate obtained by administration of a composition comprising the same dosage of said antineoplastic agent without said biodegradable polymer.

33. The article of claim 31, wherein said composition increases the median survival rate from said cancer by at least about 30%, as compared with the median survival rate obtained by administration of a composition comprising the same dosage of said antineoplastic agent without said biodegradable polymer.

34. The article of claim 31 wherein a single dose of said polymer composition provides extended release of said antineoplastic agent over a time of at least 28 days.

35. The article of claim 31 wherein each of M$^1$ and L is a branched or straight chain alkylene group.

36. The article of claim 31 wherein each of M$^1$ and L has from 1 to 7 carbon atoms.

37. The article of claim 31 wherein M$^1$ is an ethylene group or a methyl-substituted methylene group, and L is an ethylene group.

38. The article of claim 31 wherein R$^3$ is an alkyl group, an alkoxy group, a phenyl group, a phenoxy group, or a heterocycloxy group.

39. The article of claim 31 wherein R$^3$ is an alkoxy group having from 1 to 7 carbon atoms.

40. The article of claim 31 wherein R$^3$ is an ethoxy group.

41. The article of claim 31 wherein each of M$^1$ and M$^2$ is a branched or straight chain alkylene group.

42. The article of claim 31 wherein at least one of M$^1$ and M$^2$ is an alkylene or alkoxylene group having a formula selected from the group consisting of —(CH$_2$)$_a$—, —(CH$_2$)$_a$—O—, and —(CH$_2$)$_a$—O—(CH$_2$)$_b$—, wherein each of a and b is 1–7.

43. The article of claim 31 wherein at least one of M$^1$ and M$^2$ has the formula: —CHR'—CO—O—CHR"—, wherein R' and R" are each independently H, alkyl, alkoxy, aryl, aryloxy, heterocyclic or heterocycloxy.

44. The article of claim 31 wherein M$^1$ has from 1 to 7 carbon atoms.

45. The article of claim 31 wherein X is —O—.

46. The article of claim 31 wherein X is —NR$^4$—.

47. The article of claim 31 wherein:
M$^1$ is an alkylene or alkoxylene group;
L is an alkylene group;
X is —O—; and
R$^3$ is an alkoxy group.

48. The article of claim 31 wherein the molar ratio x:y is about 1.

49. The article of claim 31 wherein each of x and y is about 1 to 1,000.

50. The article of claim 31 wherein the molar ratio n:(x or y) is between about 100:1 and 1:100.

51. The article of claim 31, wherein said polymer is prepared by melt polymerization.

52. The article of claim 31, wherein said polymer comprises additional biocompatible monomeric units or is blended with other biocompatible polymers.

53. The article of claim 31, wherein said polymer is soluble in at least one of the solvents selected from the group consisting of acetone, dimethylene chloride, chloroform, ethyl acetate, DMAC, N-methyl pyrrolidone, dimethylformamide and dimethylsulfoxide.

54. The article of claim 31, wherein said antineoplastic agent comprises paclitaxel.

55. The article of claim 31, wherein the molecular weight (Mw) of said polymer is from about 2,000 to 400,000 daltons.

56. The article of claim 31, wherein said antineoplastic agent and said polymer form an amorphous, monolithic matrix.

57. The article of claim 31, wherein said antineoplastic agent is encapsulated within said polymer.

58. The article of claim 31, wherein said article results in minimal irritation to non-neoplastic tissues when implanted or injected into vasculated tissue.

59. The article of claim 31, wherein said article is in the form of a flexible film, a wafer or a rod.

60. The article of claim 31, wherein said article is in the form of one or more injectable microparticles.

61. The article of claim 31, in the form of spray-dried microspheres.

62. The article of claim 31, wherein the composition comprises about 5–15% by weight of the antineoplastic agent.

63. A method for treating a mammalian subject having ovarian cancer, by the extended release of an antineoplastic agent, said method comprising the steps of:

(a) combining the antineoplastic agent with a biodegradable polymer having the recurring monomeric units shown in formula III:

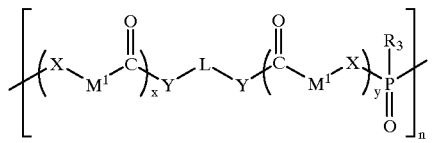

wherein
X is —O— or —NR$^4$—, where R$^4$ is H or alkyl;
Y is —O—, —S— or —NR$^4$—;
M$^1$ is (1) a branched or straight chain aliphatic group having from 1–20 carbon atoms; or (2) a branched or straight chain, oxy-, carboxy- or amino-aliphatic group having from 1–20 carbon atoms;
L is a divalent, branched or straight chain aliphatic group having 1–20 carbon atom;
R$^3$ is selected from the group consisting of H, alkyl, alkoxy, aryl, aryloxy, heterocyclic or heterocycloxy;
the molar ratio of x:y is about 1;
the molar ratio n:(x or y) is between about 200:1 and 1:200; and
n is about 5–5,000; and
(b) inserting said composition in vivo into the peritoneum of said subject, such that the inserted composition is in at least partial contact with an ovarian cancer tumor, wherein the median survival rate from said cancer is increased by at least about 10%, as compared with the median survival rate obtained by administration of a composition comprising the same dosage of said antineoplastic agent without said biodegradable polymer.

64. The method of claim 63, wherein said composition increases the median survival rate from said cancer by at least about 20%, as compared with the median survival rate obtained by administration of a composition comprising the same dosage of said antineoplastic agent without said biodegradable polymer.

65. The method of claim 63, wherein said composition increases the median survival rate from said cancer by at least about 30%, as compared with the median survival rate obtained by administration of a composition comprising the same dosage of said antineoplastic agent without said biodegradable polymer.

66. The method of claim 63 wherein a single dose of said polymer composition provides extended release of said antineoplastic agent over a time of at least 28 days.

67. The method of claim 63 wherein each of M$^1$ and L is a branched or straight chain alkylene group.

68. The method of claim 63 wherein each of M$^1$ and L has from 1 to 7 carbon atoms.

69. The method of claim 63 wherein M$^1$ is an ethylene group or a methyl-substituted methylene group, and L is an ethylene group.

70. The method of claim 63 wherein R$^3$ is an alkyl group, an alkoxy group, a phenyl group, a phenoxy group, or a heterocycloxy group.

71. The method of claim 63 wherein R$^3$ is an alkoxy group having from 1 to 7 carbon atoms.

72. The method of claim 63 wherein R$^3$ is an ethoxy group.

73. The method of claim 63 wherein M$^1$ is a branched or straight chain alkylene group.

74. The method of claim 63 wherein M$^1$ is an alkylene or alkoxylene group having a formula selected from the group consisting of —(CH$_2$)$_a$—, —(CH$_2$)$_a$—O—, and —(CH$_2$)$_a$—O—(CH$_2$)$_b$—, wherein each of a and b is an integer in the range of 1 to 7.

75. The method of claim 63 wherein M$^1$ has the formula: —CHR'—CO—O—CHR"—, wherein R' and R" are each independently H, alkyl, alkoxy, aryl, aryloxy, heterocyclic or heterocycloxy.

76. The method of claim 63 wherein M$^1$ has from 1 to 7 carbon atoms.

77. The method of claim 63 wherein X is —O—.

78. The method of claim 63 wherein X is —NR$^4$—.

79. The method of claim 63 wherein:
M$^1$ is an alkylene or alkoxylene group;
L is an alkylene group;
X is —O—; and
R$^3$ is an alkoxy group.

80. The method of claim 63 wherein the molar ratio x:y is about 1.

81. The method of claim 63 wherein each of x and y is about 1 to 1,000.

82. The method of claim 63 wherein the molar ratio n:(x or y) is between about 100:1 and 1:100.

83. The method of claim 63, wherein said polymer is prepared by solution polymerization.

84. The method of claim 63, wherein said polymer is prepared by melt polymerization.

85. The method of claim 63, wherein said polymer comprises additional biocompatible monomeric units or is blended with other biocompatible polymers.

86. The method of claim 63, wherein said polymer is soluble in at least one of the solvents selected from the group consisting of acetone, dimethylene chloride, chloroform, ethyl acetate, DMAC, N-methyl pyrrolidone, dimethylformamide and dimethylsulfoxide.

87. The method of claim 63, wherein said antineoplastic agent comprises paclitaxel.

88. The method of claim 63, wherein the molecular weight (Mw) of said polymer is from about 2,000 to 400,000 daltons.

89. The method of claim 63, wherein said antineoplastic agent and said polymer form an amorphous, monolithic matrix.

90. The method of claim 63, wherein said antineoplastic agent is encapsulated within said polymer.

91. The method of claim 63, wherein said article results in minimal irritation to non-neoplastic tissues when implanted or injected into vasculated tissue.

92. The method of claim 63, wherein said composition is a viscous liquid.

93. The method of claim 63, wherein said composition is formed into a shaped, solid article.

94. The method of claim 63, wherein said article is in the form of a flexible film, a wafer or a rod.

95. The method of claim 63, wherein said article is in the form of one or more injectable microparticles.

96. The method of claim 63, wherein the composition comprises about 5–15% by weight of the antineoplastic agent.

97. The biodegradable polymer composition of claim 1, wherein the mammalian subject is a rat or mouse.

98. The solid article of claim 31, wherein the mammalian subject is a rat or mouse.

99. The method of claim 63, wherein the mammalian subject is a rat or mouse.

100. A polymer composition comprising:
(a) at least one antineoplastic agent, and
(b) a biodegradable polymer comprising the recurring monomeric units shown in Formula III:
wherein
X is —O— or —NR$^4$—, where R$^4$ is H or alkyl;
Y is —O—, —S— or —NR$^4$—;
each of R$^1$ and R$^2$ is a divalent organic moiety;
L is a divalent, branched or straight chain aliphatic group having 1–20 carbon atom, a cycloaliphatic group, or a group having the formula:

R$^3$ is selected from the group consisting of H, alkyl, alkoxy, aryl, aryloxy, heterocyclic or heterocycloxy; and
n is about 5–5,000;
M$^1$ is (1) a branched or straight chain aliphatic group having from 1–20 carbon atoms; or (2) a branched or straight chain oxy-, carboxy- or amino-aliphatic group having from 1–20 carbon atoms;
the molar ratio of x:y is about 1; and
the molar ratio of n:(x or y) is between about 200:1 and 1:200;
wherein the polymer composition is suitable for administration to a mammal, and
wherein the polymer composition is in at least partial contact with an ovarian cancer tumor or the tissue surrounding the site of an ovarian cancer tumor.

101. The polymer composition of claim 100, wherein the polymer composition provides extended release of at least one antineoplastic agent for at least about four weeks.

102. The polymer composition of claim 101, wherein at least one antineoplastic agent comprises paclitaxel.

103. The polymer composition of claim 100, wherein at least one antineoplastic agent comprises paclitaxel.

104. The polymer composition of claim 100, wherein the polymer composition provides extended release of at least one antineoplastic agent for at least about four weeks.

105. The polymer composition of claim 104, wherein at least one antineoplastic agent comprises paclitaxel.

106. The polymer composition of claim 100, wherein the cancer tumor has been removed from the site of an ovarian cancer tumor.

107. The article of claim 30, wherein the cancer tumor has been removed from the site of an ovarian cancer tumor.

108. The article of claim 107, wherein the polymer composition provides extended release of at least one antineoplastic agent for at least about four weeks.

109. The article of claim 108, wherein at least one antineoplastic agent comprises paclitaxel.

110. The composition of claim 1, wherein the composition comprises about 5–15% by weight of the antineoplastic agent.

111. The article of claim 30, wherein at least one antineoplastic agent comprises paclitaxel.

112. The article of claim 30, wherein the polymer composition provides extended release of at least one antineoplastic agent for at least about four weeks.

113. The article of claim 112, wherein at least one antineoplastic agent comprises paclitaxel.

* * * * *